United States Patent
Lai et al.

(10) Patent No.: US 8,252,267 B2
(45) Date of Patent: *Aug. 28, 2012

(54) DKKL-1 SPLICE PRODUCT MODULATORS FOR CANCER DIAGNOSIS AND THERAPY

(75) Inventors: Albert Lai, Davis, CA (US); Robert Booher, Davis, CA (US)

(73) Assignee: Sagres Discovery, Inc., Emeryville, CA (US)

(*) Notice: Subject to any disclaimer, the term of this patent is extended or adjusted under 35 U.S.C. 154(b) by 862 days.

This patent is subject to a terminal disclaimer.

(21) Appl. No.: 11/887,692

(22) PCT Filed: Mar. 30, 2006

(86) PCT No.: PCT/US2006/011761
§ 371 (c)(1),
(2), (4) Date: Jan. 13, 2009

(87) PCT Pub. No.: WO2006/105343
PCT Pub. Date: Oct. 5, 2006

(65) Prior Publication Data
US 2009/0155276 A1 Jun. 18, 2009

Related U.S. Application Data

(60) Provisional application No. 60/666,431, filed on Mar. 30, 2005.

(51) Int. Cl.
*A61K 49/16* (2006.01)
*A61K 39/395* (2006.01)

(52) U.S. Cl. .............. 424/9.341; 424/1.49; 424/9.34; 424/9.6; 424/130.1; 424/139.1; 424/155.1; 424/156.1; 530/387.9; 530/391.1; 530/391.3

(58) Field of Classification Search .......... 424/1.49, 424/9.34, 9.341, 9.6, 130.1, 139.1, 155.1, 424/156.1; 530/387.9, 391.1, 391.3
See application file for complete search history.

(56) References Cited

U.S. PATENT DOCUMENTS

| | | | | |
|---|---|---|---|---|
| 5,736,120 A | * | 4/1998 | Srinivasan | 424/1.69 |
| 7,057,017 B2 | * | 6/2006 | McCarthy | 530/350 |
| 2007/0282015 A1 | * | 12/2007 | Albert | 514/789 |

FOREIGN PATENT DOCUMENTS

| WO | WO 99/31236 | 6/1999 |
|---|---|---|
| WO | WO 99/66041 | 12/1999 |
| WO | WO 00/52047 | 9/2000 |
| WO | WO 03/050245 | 6/2003 |
| WO | WO 2004/007527 | 1/2004 |
| WO | WO 2005/033343 | 4/2005 |

OTHER PUBLICATIONS

Krupnik Valery E et al "Functional and structural diversity of the human Dickkopf gene family" Gene 238:301-313 (1999).
Database Geneseq "Extended human secreted protein sequence, SEQ ID No. 219" XP002410889, Accession No. AAY35970, abstract (Sep. 1999).
Database UniProt "Dickkopf-like protein 1 precursor (Soggy-1 protein) (SGY-1)" XP002410892, abstract (Feb. 2001).
Database EBI "Human SGY-1 PCR primer SEQ ID No. 72" XP002410984, Accession No. ADD13159, abstract (Jan. 2004).

* cited by examiner

*Primary Examiner* — Alana Harris Dent
*Assistant Examiner* — Anne Holleran
(74) *Attorney, Agent, or Firm* — David A. Carpenter

(57) ABSTRACT

The present invention relates to novel sequences for use in detection, diagnosis and treatment of diseases, including cancer. The invention provides novel splice products of human DKKL-1 gene. The present invention provides methods of using polynucleotides having the novel splice products of the human DKKL-1 sequences, their corresponding gene products and modulators of the DKKL-1 splice products for the detection, diagnosis, prevention and/or treatment of associated cancers.

9 Claims, 25 Drawing Sheets

```
                        1                                                              64
    hCT7238_ORF     (1)----ATGGGAGAAGCCTCCCCACCTGCCCCCGCAAGGCGGCATCTGCTGGTCCTGCTGCTGCTC
    sgrs0379-stop   (1)CACCATGGGAGAAGCCTCCCCACCTGCCCCCGCAAGGCGGCATCTGCTGGTCCTGCTGCTGCTC
    clone-379-R6    (1)CACCATGGGAGAAGCCTCCCCACCTGCCCCCGCAAGGCGGCATCTGCTGGTCCTGCTGCTGCTC
    clone 379-R7    (1)CACCATGGGAGAAGCCTCCCCACCTGCCCCCGCAAGGCGGCATCTGCTGGTCCTGCTGCTGCTC
    clone-379-R3    (1)CACCATGGGAGAAGCCTCCCCACCTGCCCCCGCAAGGCGGCATCTGCTGGTCCTGCTGCTGCTC
    clone-379-RS2   (1)CACCATGGGAGAAGCCTCCCCACCTGCCCCCGCAAGGCGGCATCTGCTGGTCCTGCTGCTGCTC
    clone 379-R8    (1)CACCATGGGAGAAGCCTCCCCACCTGCCCCCGCAAGGCGGCATCTGCTGGTCCTGCTGCTGCTC
    clone-379-RS3   (1)CACCATGGGAGAAGCCTCCCCACCTGCCCCCGCAAGGCGGCATCTGCTGGTCCTGCTGCTGCTC
    clone-379 R4    (1)CACCATGGGAGAAGCCTCCCCACCTGCCCCCGCAAGGCGGCATCTGCTGGTCCTGCTGCTGCTC
    clone-379-R5    (1)CACCATGGGAGAAGCCTCCCCACCTGCCCCCGCAAGGCGGCATCTGCTGGTCCTGCTGCTGCTC
    clone-379-R2    (1)CACCATGGGAGAAGCCTCCCCACCTGCCCCCGCAAGGCGGCATCTGCTGGTCCTGCTGCTGCTC
    clone-379-RS7   (1)CACCATGGGAGAAGCCTCCCCACCTGCCCCCGCAAGGCGGCATCTGCTGGTCCTGCTGCTGCTC
    clone-379-RS4   (1)CACCATGGGAGAAGCCTCCCCACCTGCCCCCGCAAGGCGGCATCTGCTGGTCCTGCTGCTGCTC
                        65                                                             128
    hCT7238_ORF    (61)CTCTCTACCCTGGTGATCCCCTCCGCTGCAGCTCCTATCCATGATGCTGACGCCCAAGAGAGCT
    sgrs0379-stop  (65)CTCTCTACCCTGGTGATCCCCTCCGCTGCAGCTCCTATCCATGATGCTGACGCCCAAGAGAGCT
    clone-379-R6   (65)CTCTCTACCCTGGTGATCCCCTCCACTGCAGCTCCTATCCATGATGCTGACGCCCAAGAGAGCT
    clone 379-R7   (65)CTCTCTACCCTGGTGATCCCCTCCACTGCAGCTCCTATCCATGATGCTGACGCCCAAGAGAGCT
    clone-379-R3   (65)CTCTCTACCCTGGTGATCCCCTCCACTGCAGCTCCTATCCATGATGCTGACGCCCAAGAGAGCT
    clone-379-RS2  (65)CTCTCTACCCTGGTGATCCCCTCCACTGCAGCTCCTATCCATGATGCTGACGCCCAAGAGAGCT
    clone 379-R8   (65)CTCTCTACCCTGGTGATCCCCTCCGCTGCAGCTCCTATCCATGATGCTGACGCCCAAGAGAGCT
    clone-379-RS3  (65)CTCTCTACCCTGGTGATCCCCTCCGCTGCAGCTCCTATCCATGATGCTGACGCCCAAGAGAGCT
    clone-379 R4   (65)CTCTCTACCCTGGTGATCCCCTCCGCTGCAGCTCCTATCCATGATGCTGACGCCCAAGAGAGCT
    clone-379-R5   (65)CTCTCTACCCTGGTGATCCCCTCCGCTGCAGCTCCTATCCATGATGCTGACGCCCAAGAGAGCT
    clone-379-R2   (65)CTCTCTACCCTGGTGATCCCCTCCGCTGCAGCTCCTATCCATGATGCTGACGCCCAAGAGAGCT
    clone-379-RS7  (65)CTCTCTACCCTGGTGATCCCCTCCGCTGCAGCTCCTATCCATGATGCTGACGCCCAAGAGAGCT
    clone-379-RS4  (65)CTCTCTACCCTGGTGATCCCCTCCACTGCAGCTCCTATCCATGATGCTGACGCCCAAGAGAGCT
                        129                                                            192
    hCT7238_ORF   (125)CCTTGGGTCTCACAGGCCTCCAGAGCCTACTCCAAGGCTTCAGCCGACTTTTCCTGAAAGGTAA
    sgrs0379-stop (129)CCTTGGGTCTCACAGGCCTCCAGAGCCTACTCCAAGGCTTCAGCCGACTTTTCCTGAAAGGTAA
    clone-379-R6  (129)CCTTGGGTCTCACAGGCCTCCAGAGCCTACTCCAAGGCTTCAGCCGACTTTTCCTGAAAGGTAA
    clone 379-R7  (129)CCTTGGGTCTCACAGGCCTCCAGAGCCTACTCCAAGGCTTCAGCCGACTTTTCCTGAAAGGTAA
    clone-379-R3  (129)CCTTGGGTCTCACAGGCCTCCAGAGCCTACTCCAAGGCTTCAGCCGACTTTTCCTGAAAGGTAA
    clone-379-RS2 (129)CCTTGGGTCTCACAGGCCTCCAGAGCCTACTCCAAGGCTTCAGCCGACTTTTCCTGAAAGGTAA
    clone 379-R8  (129)CCTTGGGTCTCACAGGCCTCCAGAGCCTACTCCAAGGCTTCAGCCGACTTTTCCTGAAAGGTAA
    clone-379-RS3 (129)CCTTGGGTCTCACAGGCCTCCAGAGCCTACTCCAAGGCTTCAGCCGACTTTTCCTGAAAGGTAA
    clone-379 R4  (129)CCTTGGGTCTCACAGGCCTCCAGAGCCTACTCCAAGGCTTCAGCCGACTTTTCCTGAAAG----
    clone-379-R5  (129)CCTTGGGTCTCACAGGCCTCCAGAGCCTACTCCAAGGCTTCAGCCGACTTTTCCTGAAAG----
    clone-379-R2  (129)CCTTGGGTCTCACAGGCCTCCAGAGCCTACTCCAAGGCTTCAGCCGACTTTTCCTGAAAG----
    clone-379-RS7 (129)CCTTGGGTCTCACAGGCCTCCAGAGCCTACTCCAAGGCTTCAGCCGACTTTTCCTGAAAG----
    clone-379-RS4 (129)CCTTGGGTCTCACAGGCCTCCAGAGCCTACTCCAAGGCTTCAGCCGACTTTTCCTGAAAG----
```

FIG. 3A

```
                        193                                                          256
   hCT7238_ORF  (189) CCTGCTTCGGGGCATAGACAGCTTATTCTCTGCCCCCATGGACTTCCGGGGCCTCCCTGGGAAC
  sgrs0379-stop (193) CCTGCTTCGGGGCATAGACAGCTTATTCTCTGCCCCCATGGACTTCCGGGGCCTCCCTGGGAAC
   clone-379-R6 (193) CCTGCTTCGGGGCATAGACAGCTTATTCTCTGCCCCCATGGACTTCCGGGGCCTCCCTGGGAAC
    clone 379-R7 (193) CCTGCTTCGGGGCATAGACAGCTTATTCTCTGCCCCCATGGACTTCCGGGGCCTCCCTGGGAAC
   clone-379-R3 (193) CCTGCTTCGGGGCATAGACAGCTTATTCTCTGCCCCCATGGACTTCCGGGGCCTCCCTGGGAAC
  clone-379-RS2 (193) CCTGCTTCGGGGCATAGACAGCTTATTCTCTGCCCCCATGGACTTCCGGGGCCTCCCTGGGAAC
    clone 379-R8 (193) CCTGCTTCGGGGCATAGACAGCTTATTCTCTGCCCCCATGGACTTCCGGGGCCTCCCTGGGAAC
  clone-379-RS3 (193) CCTGCTTCGGGGCATAGACAGCTTATTCTCTGCCCCCATGGACTTCCGGGGCCTCCCTGGGAAC
    clone-379 R4 (189) ----------------------------------------------------------------
   clone-379-R5 (189) ----------------------------------------------------------------
   clone-379-R2 (189) ----------------------------------------------------------------
  clone-379-RS7 (189) ----------------------------------------------------------------
  clone-379-RS4 (189) ----------------------------------------------------------------
                        257                                                          320
   hCT7238_ORF  (253) TACCACAAAGAGGAGAACCAGGAGCACCAGCTGGGGAACAACACCCTCTCCAGCCACCTCCAGA
  sgrs0379-stop (257) TACCACAAAGAGGAGAACCAGGAGCACCAGCTGGGGAACAACACCCTCTCCAGCCACCTCCAGA
   clone-379-R6 (257) TACCACAAAGAGGAGAACCAGGAGCACCAGCTGGGGAACAACACCCTCTCCAGCCACCTCCAGA
    clone 379-R7 (257) TACCACAAAGAGGAGAACCAGGAGCACCAGCTGGGGAACAACACCCTCTCCAGCCACCTCCAGA
   clone-379-R3 (257) TACCACAAAGAGGAGAACCAGGAGCACCAGCTGGGGAACAACACCCTCTCCAGCCACCTCCAGA
  clone-379-RS2 (257) TACCACAAAGAGGAGAACCAGGAGCACCAGCTGGGGAACAACACCCTCTCCAGCCACCTCCAGA
    clone 379-R8 (257) TACCACAAAGAGGAGAACCAGGAGCACCAGCTGGGGAACAACACCCTCTCCAGCCACCTCCAGA
  clone-379-RS3 (257) TACCACAAAGAGGAGAACCAGGAGCACCAGCTGGGGAACAACACCCTCTCCAGCCACCTCCAGA
    clone-379 R4 (189) ----------------------------------------------------------------
   clone-379-R5 (189) ----------------------------------------------------------------
   clone-379-R2 (189) ----------------------------------------------------------------
  clone-379-RS7 (189) ----------------------------------------------------------------
  clone-379-RS4 (189) ----------------------------------------------------------------
                        321                                                          384
   hCT7238_ORF  (317) TCGACAAGAGGACCGACAACAAGACAGGAGAGGTGCTGATCTCCGAGAATGTGGTGGCATCCAT
  sgrs0379-stop (321) TCGACAAGATGACCGACAACAAGACAGGAGAGGTGCTGATCTCCGAGAATGTGGTGGCATCCAT
   clone-379-R6 (321) TCGACAAGATGACCGACAACAAGACAGGAGAGGTGCTGATCTCCGAGAATGTGGTGGCATCCAT
    clone 379-R7 (321) TCGACAAGATGACCGACAACAAGACAGGAGAGGTGCTGATCTCCGAGAATGTGGTGGCATCCAT
   clone-379-R3 (321) TCGACAAGATGACCGACAACAAGACAGGAGAGGTGCTGATCTCCGAGAATGTGGTGGCATCCAT
  clone-379-RS2 (321) TCGACAAGATGACCGACAACAAGACAGGAGAGGTGCTGATCTCCGAGAATGTGGTGGCATCCAT
    clone 379-R8 (321) TCGACAAGG-------------------------------------------------------
  clone-379-RS3 (321) TCGACAAGG-------------------------------------------------------
    clone-379 R4 (189) ----------------------------------------------------------------
   clone-379-R5 (189) ----------------------------------------------------------------
   clone-379-R2 (189) ----------------------------------------------------------------
  clone-379-RS7 (189) ----------------------------------------------------------------
  clone-379-RS4 (189) ----------------------------------------------------------------
```

FIG. 3B

```
                          385                                                           448
hCT7238_ORF    (381) TCAACCAGCGGAGGGGAGCTTCGAGGGTGATTTGAAGGTACCCAGGATGGAGGAGAAGGAGGCC
sgrs0379-stop  (385) TCAACCAGCGGAGGGGAGCTTCGAGGGTGATTTGAAGGTACCCAGGATGGAGGAGAAGGAGGCC
clone-379-R6   (385) TCAACCAGCGGAGGGGAGCTTCGAGGGTGATTTGAAGGTACCCAGGATGGAGGAGAAGGAGGCC
clone 379-R7   (385) TCAACCAGCGGAGGGGAGCTTCGAGGGTGATTTGAAGGTACCCAGGATGGAGGAGAAGGAGGCC
clone-379-R3   (385) TCAACCAGCGGAGGGGAGCTTCGAGGGTGATTTGAAGGTACCCAGGATGGAGGAGAAGGAGGCC
clone-379-RS2  (385) TCAACCAGCGGAGGGGAGCTTCGAGGGTGATTTGAAGGTACCCAGGATGGAGGAGAAGGAGGCC
clone 379-R8   (330) --------------------------------------TACCCAGGATGGAGGAGAAGGAGGCC
clone-379-RS3  (330) --------------------------------------TACCCAGGATGGAGGAGAAGGAGGCC
clone-379 R4   (189) --------------------------------------TACCCAGGATGGAGGAGAAGGAGGCC
clone-379-R5   (189) --------------------------------------TACCCAGGATGGAGGAGAAGGAGGCC
clone-379-R2   (189) --------------------------------------TACCCAGGATGGAGGAGAAGGAGGCC
clone-379-RS7  (189) --------------------------------------TACCCAGGATGGAGGAGAAGGAGGCC
clone-379-RS4  (189) --------------------------------------TACCCAGGATGGAGGAGAAGGAGGCC
                          449                                                           512
hCT7238_ORF    (445) CTGGTACCCATCCAGAAGGCCACGGACAGCTTCCACACAGAACTCCATCCCCGGGTGGCCTTCT
sgrs0379-stop  (449) CTGGTACCCATCCAGAAGGCCACGGACAGCTTCCACACAGAACTCCATCCCCGGGTGGCCTTCT
clone-379-R6   (449) CTGGTACCCATCCAGAAGGCCACGGACAGCTTCCACACAGAACTCCATCCCCGGGTGGCCTTCT
clone 379-R7   (449) CTGGTACCCATCCAGAAGGCCACGGACAGCTTCCACACAGAACTCCATCCCCGGGTGGCCTTCT
clone-379-R3   (449) CTGGTACCCATCCAGAAGGCCACGGACAGCTTCCACACAGAACTCCATCCCCGGGTGGCCTTCT
clone-379-RS2  (449) CTGGTACCCATCCAGAAGGCCACGGACAGCTTCCACACAGAACTCCATCCCCGGGTGGCCTTCT
clone 379-R8   (356) CTGGTACCCATCCAGAAGGCCACGGACAGCTTCCACACAGAACTCCATCCCCGGGTGGCCTTCT
clone-379-RS3  (356) CTGGTACCCATCCAGAAGGCCACGGACAGCTTCCACACAGAACTCCATCCCCGGGTGGCCTTCT
clone-379 R4   (215) CTGGTACCCATCCAGAAGGCCACGGACAGCTTCCACACAGAACTCCATCCCCGGGTGGCCTTCT
clone-379-R5   (215) CTGGTACCCATCCAGAAGGCCACGGACAGCTTCCACACAGAACTCCATCCCCGGGTGGCCTTCT
clone-379-R2   (215) CTGGTACCCATCCAGAAGGCCACGGACAGCTTCCACACAGAACTCCATCCCCGGGTGGCCTTCT
clone-379-RS7  (215) CTGGTACCCATCCAGAAGGCCACGGACAGCTTCCACACAGAACTCCATCCCCGGGTGGCCTTCT
clone-379-RS4  (215) CTGGTACCCATCCAGAAGGCCACGGACAGCTTCCACACAGAACTCCATCCCCGGGTGGCCTTCT
                          513                                                           576
hCT7238_ORF    (509) GGATCATTAAGCTGCCACGGCGGAGGTCCCACCAGGATGCCCTGGAGGGCGGCCACTGGCTCAG
sgrs0379-stop  (513) GGATCATTAAGCTGCCACGGCGGAGGTCCCACCAGGATGCCCTGGAGGGCGGCCACTGGCTCAG
clone-379-R6   (513) GGATCATTAAGCTGCCACGGCGGAGGTCCCACCAGGATGCCCTGGAGGGCGGCCACTGGCTCAG
clone 379-R7   (513) GGATCATTAAGCTGCCACGGCGGAGGTCCCACCAGGATGCCCTGGAGGGCGGCCACTGGCTCAG
clone-379-R3   (513) GGATCATTAAGCTGCCACGGCGGAGGTCCCACCAGGATGCCCTGGAGGGCAGCCACTGGCTCAG
clone-379-RS2  (513) GGATCATTAAGCTGCCACGGCGGAGGTCCCACCAGGATGCCCTGGAGGGCGGCCACTGGCTCAG
clone 379-R8   (420) GGATCATTAAGCTGCCACGGCGGAGGTCCCACCAGGATGCCCTGGAGGGCGGCCACTGGCTCAG
clone-379-RS3  (420) GGATCATTAAGCTGCCACGGCGGAGGTCCCACCAGGATGCCCTGGAGGGCGGCCACTGGCTCAG
clone-379 R4   (279) GGATCATTAAGCTGCCACGGCGGAGGTCCCACCAGGATGCCCTGGAGGGCAGCCACTGGCTCAG
clone-379-R5   (279) GGATCATTAAGCTGCCACGGCGGAGGTCCCACCAGGATGCCCTGGAGGGCAGCCACTGGCTCAG
clone-379-R2   (279) GGATCATTAAGCTGCCACGGCGGAGGTCCCACCAGGATGCCCTGGAGGGCAGCCACTGGCTCAG
clone-379-RS7  (279) GGATCATTAAGCTGCCACGGCGGAGGTCCCACCAGGATGCCCTGGAGGGCAGCCACTGGCTCAG
clone-379-RS4  (279) GGATCATTAAGCTGCCACGGCGGAGGTCCCACCAGGATGCCCTGGAGGGCAGCCACTGGCTCAG
```

FIG. 3C

```
                        577                                                              640
   hCT7238_ORF  (573)  CGAGAAGCGACACCGCCTGCAGGCCATCCGGGATGGACTCCGCAAGGGGACCCACAAGGACGTC
   sgrs0379-stop (577) CGAGAAGCGACACCGCCTGCAGGCCATCCGGGATGGACTCCGCAAGGGGACCCACAAGGACGTC
   clone-379-R6  (577) CGAGAAGCGACACCGCCTGCAGGCCATCCGGGATGGACTCCGCAAGGGGACCCACAAGGACGTC
   clone 379-R7  (577) CGAGAAGCGACACCGCCTGCAGGCCATCCGGGATGGACTCCGCAAGGGGACCCACAAGGACGTC
   clone-379-R3  (577) CGAGAAGCGACACCGCCTGCAGGCCATCCGGGATGGACTCCGCAAGGGGACCCACAAGGACGTC
   clone-379-RS2 (577) CGAGAAGCGACACCGCCTGCAGGCCATCCGGGATGGACTCCGCAAGGGGACCCACAAGGACGTC
   clone 379-R8  (484) CGAGAAGCGACACCGCCTGCAGGCCATCCGGGATGGACTCCGCAAGGGGACCCACAAGGACGTC
   clone-379-RS3 (484) CGAGAAGCGACACCGCCTGCAGGCCATCCGGGATGGACTCCGCAAGGGGACCCACAAGGACGTC
   clone-379 R4  (343) CGAGAAGCGACACCGCCTGCAGGCCATCCGGGATGGACTCCGCAAGGGGACCCACAAGGACGTC
   clone-379-R5  (343) CGAGAAGCGACACCGCCTGCAGGCCATCCGGGATGGACTCCGCAAGGGGACCCACAAGGACGTC
   clone-379-R2  (343) CGAGAAGCGACACCGCCTGCAGGCCATCCGGGATGGACTCCGCAAGGGGACCCACAAGGACGTC
   clone-379-RS7 (343) CGAGAAGCGACACCGCCTGCAGGCCATCCGGGATGGACTCCGCAAGGGGACCCACAAGGACGTC
   clone-379-RS4 (343) CGAGAAGCGACACCGCCTGCAGGCCATCCGGGATGGACTCCGCAAGGGGACCCACAAGGACGTC
                        641                                                              704
   hCT7238_ORF  (637)  CTAGAAGAGGGGACCGAGAGCTCCTCCCACTCCAGGCTGTCCCCCCGAAAGACCCACTTACTGT
   sgrs0379-stop (641) CTAGAAGAGGGGACCGAGAGCTCCTCCCACTCCAGGCTGTCCCCCCGAAAGACCCACTTACTGT
   clone-379-R6  (641) CTAGAAGAGGGGACCGAGAGCTCCTCCCACTCCAGGCTGTCCCCCCGAAAGACCCACTTACTGT
   clone 379-R7  (641) CTAGAAGAGGGGACCGAGAGCTCCTCCCACTCCAGGCTGTCCCCCCGAAAGACCCACTTACTGT
   clone-379-R3  (641) CTAAAAGAGGGGACCGAGAGCTCCTCCCACTCCAGGCTGTCCCCCCGAAAGACCCACTTACTGT
   clone-379-RS2 (641) CTAGAAGAGGGGACCGAGAGCTCCTCCCACTCCAGGCTGTCCCCCCGAAAGACCCACTTACTGT
   clone 379-R8  (548) CTAGAAGAGGGGACCGAGAGCTCCTCCCACTCCAGGCTGTCCCCCCGAAAGACCCACTTACTGT
   clone-379-RS3 (548) CTAGAAGAGGGGACCGAGAGCTCCTCCCACTCCAGGCTGTCCCCCCGAAAGACCCACTTACTGT
   clone-379 R4  (407) CTAAAAGAGGGGACCGAGAGCTCCTCCCACTCCAGGCTGTCCCCCCGAAAGACCCACTTACTGT
   clone-379-R5  (407) CTAAAAGAGGGGACCGAGAGCTCCTCCCACTCCAGGCTGTCCCCCCGAAAGACCCACTTACTGT
   clone-379-R2  (407) CTAGAAGAGGGGACCGAGAGCTCCTCCCACTCCAGGCTGTCCCCCCGAAAGACCCACTTACTGT
   clone-379-RS7 (407) CTAAAAGAGGGGACCGAGAGCTCCTCCCACTCCAGGCTGTCCCCCCGAAAGACCCACTTACTGT
   clone-379-RS4 (407) CTAAAAGAGGGGACCGAGAGCTCCTCCCACTCCAGGCTGTCCCCCCGAAAGACCCACTTACTGT
                        705                                                              768
   hCT7238_ORF  (701)  ACATCCTCAGGCCCTCTCGGCAGCTGTAGGGGTGGGGACCGGGGAGCACCTGCCTGTAGCCCCC
   sgrs0379-stop (705) ACATCCTCAGGCCCTCTCGGCAGCTGTAG------------------------------------
   clone-379-R6  (705) ACATCCTCAGGCCCTCTCGGCAGCTGTAG------------------------------------
   clone 379-R7  (705) ACATCCTCAGGCCCTCTCGGCAGCTGTAG------------------------------------
   clone-379-R3  (705) ACATCCTCAGGCCCTCTCGGCAGCTGTAG------------------------------------
   clone-379-RS2 (705) ACATCCTCAGGCCCTCTCGGCAGCTGTAG------------------------------------
   clone 379-R8  (612) ACATCCTCAGGCCCTCTCGGCAGCTGTAG------------------------------------
   clone-379-RS3 (612) ACATCCTCAGGCCCTCTCGGCAGCTGTAG------------------------------------
   clone-379 R4  (471) ACATCCTCAGGCCCTCTCGGCAGCTGTAG------------------------------------
   clone-379-R5  (471) ACATCCTCAGGCCCTCTCGGCAGCTGTAG------------------------------------
   clone-379-R2  (471) ACATCCTCAGGCCCTCTCGGCAGCTGTAG------------------------------------
   clone-379-RS7 (471) ACATCCTCAGGCCCTCTCGGCAGCTGTAG------------------------------------
   clone-379-RS4 (471) ACATCCTCAGGCCCTCTCGGCAGCTGTAG------------------------------------
```

FIG. 3D

```
                        769                                                      823
hCT7238_ORF  (765) ATCAGACCCTGCCCCAAGCACCATATGGAAATAAAGTTCTTTCTTACATCTAACA
sgrs0379-stop (734) -------------------------------------------------------
clone-379-R6 (734) -------------------------------------------------------
clone 379-R7 (734) -------------------------------------------------------
clone-379-R3 (734) -------------------------------------------------------
clone-379-RS2 (734) -------------------------------------------------------
clone 379-R8 (641) -------------------------------------------------------
clone-379-RS3 (641) -------------------------------------------------------
clone-379 R4 (500) -------------------------------------------------------
clone-379-R5 (500) -------------------------------------------------------
clone-379-R2 (500) -------------------------------------------------------
clone-379-RS7 (500) -------------------------------------------------------
clone-379-RS4 (500) -------------------------------------------------------
```

FIG. 3E

|                                   |      | 1                                               48 |
|-----------------------------------|------|-----------------------------------------------------|
| hCP35274.2                        | (1)  | MGEASPPAPARRHLLVLLLLLSTLVIPSAAAPIHDADAQESSLGLTGL |
| Translation of DKKL1-pending_chris | (1) | MGEASPPAPARRHLLVLLLLLSTLVIPSAAAPIHDADAQESSLGLTGL |
| Translation of clone 379-R6       | (1)  | MGEASPPAPARRHLLVLLLLLSTLVIPSTAAPIHDADAQESSLGLTGL |
| Translation of clone 379-R7       | (1)  | MGEASPPAPARRHLLVLLLLLSTLVIPSTAAPIHDADAQESSLGLTGL |
| Translation of clone-379-R3       | (1)  | MGEASPPAPARRHLLVLLLLLSTLVIPSTAAPIHDADAQESSLGLTGL |
| Translation of clone-379-RS2      | (1)  | MGEASPPAPARRHLLVLLLLLSTLVIPSTAAPIHDADAQESSLGLTGL |
| Translation of clone 379-R8       | (1)  | MGEASPPAPARRHLLVLLLLLSTLVIPSAAAPIHDADAQESSLGLTGL |
| Translation of clone-379-RS3      | (1)  | MGEASPPAPARRHLLVLLLLLSTLVIPSAAAPIHDADAQESSLGLTGL |
| Translation of clone-379 R4       | (1)  | MGEASPPAPARRHLLVLLLLLSTLVIPSAAAPIHDADAQESSLGLTGL |
| Translation of clone-379-R5       | (1)  | MGEASPPAPARRHLLVLLLLLSTLVIPSAAAPIHDADAQESSLGLTGL |
| Translation of clone-379-R2       | (1)  | MGEASPPAPARRHLLVLLLLLSTLVIPSAAAPIHDADAQESSLGLTGL |
| Translation of clone-379-RS7      | (1)  | MGEASPPAPARRHLLVLLLLLSTLVIPSAAAPIHDADAQESSLGLTGL |
| Translation of clone-379-RS4      | (1)  | MGEASPPAPARRHLLVLLLLLSTLVIPSAAAPIHDADAQESSLGLTGL |
|                                   |      | 49                                             96 |
| hCP35274.2                        | (49) | QSLLQGFSRLFLKGNLLRGIDSLFSAPMDFRGLPGNYHKEENQEHQLG |
| Translation of DKKL1-pending_chris | (49)| QSLLQGFSRLFLKGNLLRGIDSLFSAPMDFRGLPGNYHKEENQEHQLG |
| Translation of clone 379-R6       | (49) | QSLLQGFSRLFLKGNLLRGIDSLFSAPMDFRGLPGNYHKEENQEHQLG |
| Translation of clone 379-R7       | (49) | QSLLQGFSRLFLKGNLLRGIDSLFSAPMDFRGLPGNYHKEENQEHQLG |
| Translation of clone-379-R3       | (49) | QSLLQGFSRLFLKGNLLRGIDSLFSAPMDFRGLPGNYHKEENQEHQLG |
| Translation of clone-379-RS2      | (49) | QSLLQGFSRLFLKGNLLRGIDSLFSAPMDFRGLPGNYHKEENQEHQLG |
| Translation of clone 379-R8       | (49) | QSLLQGFSRLFLKGNLLRGIDSLFSAPMDFRGLPGNYHKEENQEHQLG |
| Translation of clone-379-RS3      | (49) | QSLLQGFSRLFLKGNLLRGIDSLFSAPMDFRGLPGNYHKEENQEHQLG |
| Translation of clone-379 R4       | (49) | QSLLQGFSRLFLK----------------------------------- |
| Translation of clone-379-R5       | (49) | QSLLQGFSRLFLK----------------------------------- |
| Translation of clone-379-R2       | (49) | QSLLQGFSRLFLK----------------------------------- |
| Translation of clone-379-RS7      | (49) | QSLLQGFSRLFLK----------------------------------- |
| Translation of clone-379-RS4      | (49) | QSLLQGFSRLFLK----------------------------------- |
|                                   |      | 97                                            144 |
| hCP35274.2                        | (97) | NNTLSSHLQIDKRTDNKTGEVLISENVVASIQPAEGSFEGDLKVPRME |
| Translation of DKKL1-pending_chris | (97)| NNTLSSHLQIDKMTDNKTGEVLISENVVASIQPAEGSFEGDLKVPRME |
| Translation of clone 379-R6       | (97) | NNTLSSHLQIDKMTDNKTGEVLISENVVASIQPAEGSFEGDLKVPRME |
| Translation of clone 379-R7       | (97) | NNTLSSHLQIDKMTDNKTGEVLISENVVASIQPAEGSFEGDLKVPRME |
| Translation of clone-379-R3       | (97) | NNTLSSHLQIDKMTDNKTGEVLISENVVASIQPAEGSFEGDLKVPRME |
| Translation of clone-379-RS2      | (97) | NNTLSSHLQIDKMTDNKTGEVLISENVVASIQPAEGSFEGDLKVPRME |
| Translation of clone 379-R8       | (97) | NNTLSSHLQIDK--------------------------------VPRME |
| Translation of clone-379-RS3      | (97) | NNTLSSHLQIDK--------------------------------VPRME |
| Translation of clone-379 R4       | (62) | ----------------------------------------VPRME |
| Translation of clone-379-R5       | (62) | ----------------------------------------VPRME |
| Translation of clone-379-R2       | (62) | ----------------------------------------VPRME |
| Translation of clone-379-RS7      | (62) | ----------------------------------------VPRME |
| Translation of clone-379-RS4      | (62) | ----------------------------------------VPRME |

FIG. 4A

|  | | 145 192 |
|---|---|---|
| hCP35274.2 | (145) | EKEALVPIQKATDSFHTELHPRVAFWIIKLPRRRSHQDALEGSHWLSE |
| Translation of DKKL1-pending_chris | (145) | EKEALVPIQKATDSFHTELHPRVAFWIIKLPRRRSHQDALEGSHWLSE |
| Translation of clone 379-R6 | (145) | EKEALVPIQKATDSFHTELHPRVAFWIIKLPRRRSHQDALEGSHWLSE |
| Translation of clone 379-R7 | (145) | EKEALVPIQKATDSFHTELHPRVAFWIIKLPRRRSHQDALEGSHWLSE |
| Translation of clone-379-R3 | (145) | EKEALVPIQKATDSFHTELHPRVAFWIIKLPRRRSHQDALEGSHWLSE |
| Translation of clone-379-RS2 | (145) | EKEALVPIQKATDSFHTELHPRVAFWIIKLPRRRSHQDALEGGHWLSE |
| Translation of clone 379-R8 | (145) | EKEALVPIQKATDSFHTELHPRVAFWIIKLPRRRSHQDALEGGHWLSE |
| Translation of clone-379-RS3 | (114) | EKEALVPIQKATDSFHTELHPRVAFWIIKLPRRRSHQDALEGGHWLSE |
| Translation of clone-379 R4 | (67) | EKEALVPIQKATDSFHTELHPRVAFWIIKLPRRRSHQDALEGSHWLSE |
| Translation of clone-379-R5 | (67) | EKEALVPIQKATDSFHTELHPRVAFWIIKLPRRRSHQDALEGSHWLSE |
| Translation of clone-379-R2 | (67) | EKEALVPIQKATDSFHTELHPRVAFWIIKLPRRRSHQDALEGSHWLSE |
| Translation of clone-379-RS7 | (67) | EKEALVPIQKATDSFHTELHPRVAFWIIKLPRRRSHQDALEGSHWLSE |
| Translation of clone-379-RS4 | (67) | EKEALVPIQKATDSFHTELHPRVAFWIIKLPRRRSHQDALEGSHWLSE |
|  | | 193 240 |
| hCP35274.2 | (193) | KRHRLQAIRDGLRKGTHKDVLEEGTESSSHSRLSPRKTHLLYILRPSR |
| Translation of DKKL1-pending_chris | (193) | KRHRLQAIRDGLRKGTHKDVLEEGTESSSHSRLSPRKTHLLYILRPSR |
| Translation of clone 379-R6 | (193) | KRHRLQAIRDGLRKGTHKDVLEEGTESSSHSRLSPRKTHLLYILRPSR |
| Translation of clone 379-R7 | (193) | KRHRLQAIRDGLRKGTHKDVLEEGTESSSHSRLSPRKTHLLYILRPSR |
| Translation of clone-379-R3 | (193) | KRHRLQAIRDGLRKGTHKDVLEEGTESSSHSRLSPRKTHLLYILRPSR |
| Translation of clone-379-RS2 | (193) | KRHRLQAIRDGLRKGTHKDVLEEGTESSSHSRLSPRKTHLLYILRPSR |
| Translation of clone 379-R8 | (162) | KRHRLQAIRDGLRKGTHKDVLEEGTESSSHSRLSPRKTHLLYILRPSR |
| Translation of clone-379-RS3 | (162) | KRHRLQAIRDGLRKGTHKDVLEEETESSSHSRLSPRKTHLLYILRPSR |
| Translation of clone-379 R4 | (115) | KRHRLQAIRDGLRKGTHKDVLKEGTESSSHSRLSPRKTHLLYILRPSR |
| Translation of clone-379-R5 | (115) | KRHRLQAIRDGLRKGTHKDVLEEGTESSSHSRLSPRKTHLLYILRPSR |
| Translation of clone-379-R2 | (115) | KRHRLQAIRDGLRKGTHKDVLEEGTESSSHSRLSPRKTHLLYILRPSR |
| Translation of clone-379-RS7 | (115) | KRHRLQAIRDGLRKGTHKDVLKEGTESSSHSRLSPRKTHLLYILRPSR |
| Translation of clone-379-RS4 | (115) | KRHRLQAIRDGLRKGTHKDVLKEGTESSSHSRLSPRKTHLLYILRPSR |
|  | | 241 |
| hCP35274.2 | (241) | QL- |
| Translation of DKKL1-pending_chris | (241) | QL- |
| Translation of clone 379-R6 | (241) | QL- |
| Translation of clone 379-R7 | (241) | QL- |
| Translation of clone-379-R3 | (241) | QL- |
| Translation of clone-379-RS2 | (241) | QL- |
| Translation of clone 379-R8 | (210) | QL- |
| Translation of clone-379-RS3 | (210) | QL- |
| Translation of clone-379 R4 | (163) | QL- |
| Translation of clone-379-R5 | (163) | QL- |
| Translation of clone-379-R2 | (163) | QL- |
| Translation of clone-379-RS7 | (163) | QL- |
| Translation of clone-379-RS4 | (163) | QL- |

FIG. 4B

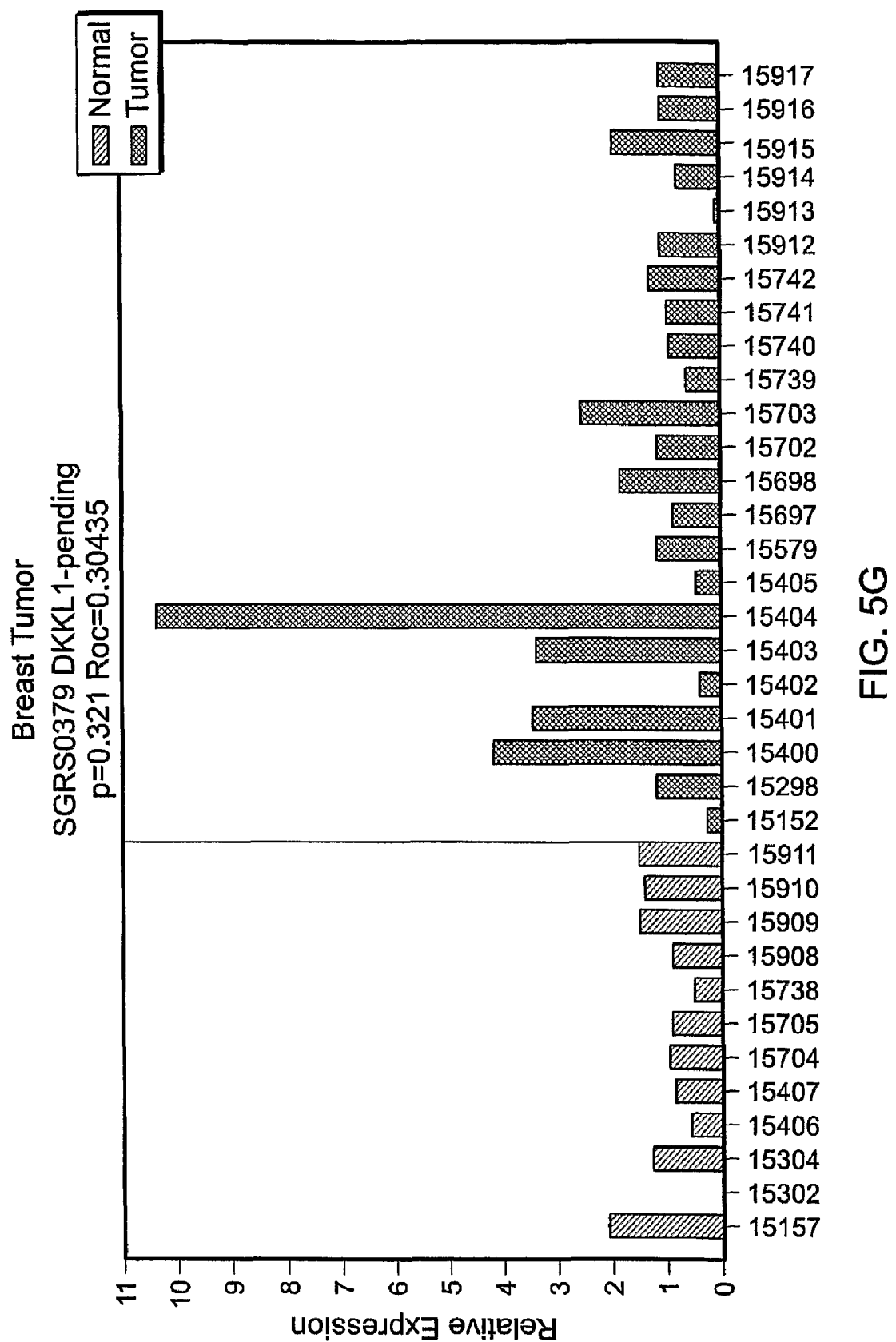

DKKL-1 SPLICE PRODUCT MODULATORS FOR CANCER DIAGNOSIS AND THERAPY

CROSS-REFERENCE TO RELATED APPLICATIONS

The present application claims priority of U.S. Ser. No. 60/666,431, filed Mar. 30, 2005, which is hereby incorporated by reference in its entirety.

TECHNICAL FIELD OF THE INVENTION

The present invention relates generally to the field of cancer-associated genes. Specifically, it relates to nucleotide and polypeptide sequences representing novel splice products of the human DKKL-1 gene in human tissue for use in diagnosis and treatment of cancer, as well as the use of the sequences in screening methods.

BACKGROUND OF THE INVENTION

Oncogenes are genes that can cause cancer. Carcinogenesis can occur by a wide variety of mechanisms, including infection of cells by viruses containing oncogenes, activation of protooncogenes in the host genome, and mutations of protooncogenes and tumor suppressor genes. Carcinogenesis is fundamentally driven by somatic cell evolution (i.e. mutation and natural selection of variants with progressive loss of growth control). The genes that serve as targets for these somatic mutations are classified as either protooncogenes or tumor suppressor genes, depending on whether their mutant phenotypes are dominant or recessive, respectively.

The pattern of gene expression in a particular living cell is characteristic of its current state. Nearly all differences in the state or type of a cell are reflected in qualitative and quantitative differences in RNA levels of one or more genes. For example, oncogenes are positive regulators of tumorigenesis, while tumor suppressor genes are negative regulators of tumorigenesis. (Marshall, Cell, 64: 313-326 (1991); Weinberg, Science, 254: 1138-1146 (1991)).

Secreted proteins are involved in signaling between cells that are not in direct contact and play a role in differentiation of cells in mammals. The wnt gene family encodes a class of secreted proteins related to the Int1/Wnt1 protooncogene (Cadigan and Nusse, Genes & Development 11:3286-3305 (1997); U.S. Patent Publication 2004/0247593 A1, which is incorporated by reference). Dickkopf (Dkk) is a negative regulator of Wnt signaling (Glinka A, et al. Nature. 1998 Jan. 22; 391(6665):357-362; Niehrs C Trends Genet. 1999 August; 15(8):314-319). The Dkk protein is secreted and rich in cysteines. A family of human Dickkopf proteins (also referred to as "Cysteine-Rich Secreted Proteins" or CRSPs) have been reported. (see WO 00/52047 (McCarthy)). There are 4 Dkk members in the human genome with different activities. Some do not inhibit Wnt signaling (Wu W, et al. Cur Biol. 2000 Dec. 14-28; 10(24):1611-1614). There are presently no known non-vertebrate homologs of Dkk.

Additional members of the human Dickkopf gene family were identified by sequence homology. A Dkk-like protein referred to as Soggy-1 (referred to herein as wild-type DKKL-1 or DKKL-1 isoform 1) has been reported. (Krupnick V E, et al. Gene 238(2): 301-313 (1999); see WO 00/52047 (McCarthy)). The mouse ortholog of Soggy-1 has been reported. (Kaneko K J et al., Nuc. Acids Res. 28(20): 3982-3990 (2000)).

Immunotherapy, or the use of antibodies for therapeutic purposes has been used in recent years to treat cancer. Passive immunotherapy involves the use of monoclonal antibodies in cancer treatments. See for example, Cancer: Principles and Practice of Oncology, 6th Edition (2001) Ch. 20 pp. 495-508. Inherent therapeutic biological activity of these antibodies include direct inhibition of tumor cell growth or survival, and the ability to recruit the natural cell killing activity of the body's immune system. These agents are administered alone or in conjunction with radiation or chemotherapeutic agents. Rituxan® and Herceptin®, approved for treatment of lymphoma and breast cancer, respectively, are two examples of such therapeutics. Alternatively, antibodies are used to make antibody conjugates where the antibody is linked to a toxic agent and directs that agent to the tumor by specifically binding to the tumor. Mylotarg® is an example of an approved antibody conjugate used for the treatment of leukemia.

Accordingly, it is another object of this invention to provide antigens (cancer-associated polypeptides) associated with a variety of cancers as targets for diagnostic and/or therapeutic antibodies. These antigens are also useful for drug discovery (e.g., small molecules) and for further characterization of cellular regulation, growth, and differentiation.

SUMMARY OF THE INVENTION

The present invention provides, inter alia, novel DKKL-1 splice product modulators for cancer diagnosis and therapy.

In some aspects, the present invention provides isolated antibodies that specifically binds an epitope of a DKKL-1 splice product. In some embodiments the DKKL-1 splice product is DKKL-1 isoform 2 or DKKL-1 isoform 3. In some embodiments the antibody is a monoclonal antibody. In some embodiments the antibody is a humanized antibody or chimeric antibody, or a fragment thereof. In some embodiments the antibody binds to a polypeptide having at least 95% sequence identity to a sequence of SEQ ID NO:4 or SEQ ID NO:6. In some embodiments the antibody binds to a polypeptide having a sequence of SEQ ID NO:4 or SEQ ID NO:6. In some embodiments the antibody inhibits cancer cell proliferation by at least 30% as compared to a control. In some embodiments the antibody inhibits cancer cell growth by at least 30% as compared to a control. In some embodiments the antibody inhibits one or more of β-catenin signaling and Wnt signaling by at least 30% as compared to a control. In some embodiments the antibody exhibits or is modified to exhibit ADCC activity. In some embodiments the antibody is labeled. In some embodiments the label is an enzyme, radioisotope or fluorophore. In some embodiments the antibody is conjugated to a cytotoxic or therapeutic agent. In some embodiments the antibody binds to the DKKL-1 splice product with an affinity of at least $1 \times 10^8$ Ka.

In some aspects, the present invention provides isolated cells that produce the antibodies of the invention.

In some aspects, the present invention provides hybridomas that produce the antibody of the invention.

In some aspects, the present invention provides non-human transgenic animals that produce the antibodies of the invention.

In some aspects, the present invention provides compositions comprising a DKKL-1 splice product modulator and one or more pharmaceutically acceptable carriers. In some embodiments the DKKL-1 splice product modulator is an isolated double-stranded RNA (dsRNA) of SEQ ID NO:3 or SEQ ID NO:5. In some embodiments the DKKL-1 splice product modulator is an isolated oligonucleotide comprising at least 10 consecutive nucleotides of a sequence of SEQ ID NO:3 or SEQ ID NO:5. In some embodiments the DKKL-1 splice product modulator is an antibody that specifically binds an epitope of a DKKL-1 splice product. In some embodiments the DKKL-1 splice product is DKKL-1 isoform 2 or DKKL-1 isoform 3. In some embodiments the antibody is a monoclonal antibody. In some embodiments the antibody further comprises a detectable label. In some embodiments the DKKL-1 splice product has a polypeptide sequence having at least 95% sequence identity to a sequence of SEQ ID NO:4 or SEQ ID NO:6. In some embodiments DKKL-1 isoform 2 has a polypeptide sequence of SEQ ID NO:4. In some embodiments DKKL-1 isoform 3 has a polypeptide sequence of SEQ ID NO:6.

In some aspects, the present invention provides methods of treating cancer or a cancer symptom in a patient in need thereof comprising administering to the patient a therapeutically effective amount of the DKKL-1 splice product modulators of the invention. In some embodiments the DKKL-1 splice product modulator inhibits growth of cancer cells that express DKKL-1 by at least 30% in an in vitro assay to measure cell growth. In some embodiments the DKKL-1 splice product modulator inhibits proliferation of cancer cells that express DKKL-1 by at least 30% in an in vitro assay to measure cell proliferation. In some embodiments the DKKL-1 splice product is DKKL-1 isoform 2 or DKKL-1 isoform 3. In some embodiments the DKKL-1 splice product modulator inhibits one or more of β-catenin signaling and Wnt signaling by at least 30% as compared to a control. In some embodiments the DKKL-1 splice product modulator inhibits expression of the DKKL-1 splice product by at least 30% as compared to a control. In some embodiments the DKKL-1 splice product modulator is an oligonucleotide having a sequence selected from the group consisting of SEQ ID NO:13, 14 and 15. In some embodiments the oligonucleotide is an antisense or RNAi oligonucleotide. In some embodiments the DKKL-1 splice product modulator is a double stranded RNA comprising a sequence capable of hybridizing to a sequence of SEQ ID NO:3, or its complement, or a sequence of SEQ ID NO:5, or its complement. In some embodiments the DKKL-1 splice product modulator is a monoclonal antibody. In some embodiments the cancer is ovarian cancer, lung cancer, liver cancer, cervical cancer, colon cancer, breast cancer or lymphoma. In some embodiments the lung cancer is mesothelioma or non-small cell lung cancer. In some embodiments the breast cancer is selected from the group consisting of ductal adenocarcinoma, lobular adenocarcinoma, and metastatic adenocarcinoma. In some embodiments the methods further comprise the administration of a traditional cancer therapeutic to the patient. In some embodiments the methods further comprise the treatment of the patient with one or more of chemotherapy, radiation therapy or surgery.

In some aspects, the present invention provides methods of modulating a DKKL-1 splice product-related biological activity in a patient. In some embodiments the methods comprise administering to the patient an amount of a DKKL-1 splice product modulator of the invention effective to modulate the DKKL-1 splice product-related biological activity. In some embodiments the DKKL-1 splice product is DKKL-1 isoform 2 or DKKL-1 isoform 3. In some embodiments the DKKL-1 splice product modulator is a monoclonal antibody which selectively binds to DKKL-1 isoform 2 or isoform 3. In some embodiments the patient has or is predisposed to one or more of ovarian cancer, lung cancer, liver cancer, cervical cancer, colon cancer, breast cancer or lymphoma. In some embodiments the DKKL-1 splice product modulator is an antibody and is administered to the subject via in vivo therapeutic antibody gene transfer.

In some aspects, the present invention provides methods of treating a cancer patient comprising (a) detecting the presence or absence of differential expression of a DKKL-1 splice product in a patient sample, wherein the presence of differential expression of the DKKL-1 splice product in the sample is indicative of a patient who is a candidate for DKKL-1 therapy; and (b) administering a therapeutically effective amount of a DKKL-1 splice product modulator of the invention to the patient if the patient is a candidate for DKKL-1 therapy; or (c) administering a traditional cancer therapeutic to the patient if the patient is not a candidate for DKKL-1 therapy. In some embodiments differential expression of the DKKL-1 splice product is detected by measuring DKKL-1 splice product RNA. In some embodiments differential expression of the DKKL-1 splice product is detected by measuring DKKL-1 splice products. In some embodiments the methods further comprise the administration of a traditional cancer therapeutic to the patient. In some embodiments the DKKL-1 splice product is DKKL-1 isoform 2 or DKKL-1 isoform 3.

In some aspects, the present invention provides methods of inhibiting a cancer cell phenotype in a population of cells expressing a DKKL-1 splice product. In some embodiments the methods comprise administering to the population an amount of a DKKL-1 splice product modulator of the invention effective to inhibit the cancer cell phenotype. In some embodiments the cancer cell phenotype is cell proliferation, cancer cell growth, cancer cell migration, cancer cell metastasis, tumorigenicity and cancer cell survival. In some embodiments the cancer cells are selected from the group consisting of ovarian cancer, lung cancer, liver cancer, cervical cancer, colon cancer, breast cancer or lymphoma.

In some aspects, the present invention provides methods for detecting one or more cancer cells expressing a DKKL-1 splice product in a sample comprising the sample with a composition comprising a DKKL-1 splice product modulator of the invention linked to an imaging agent and detecting the localization of the imaging agent in the sample. In some embodiments the DKKL-1 splice product modulator is a monoclonal antibody. In some embodiments the imaging agent is $^{18}$F, $^{43}$K, $^{52}$Fe, $^{57}$Co, $^{67}$Cu, $^{67}$Ga, $^{77}$Br, $^{87}$MSr, $^{86}$Y, $^{90}$Y, $^{99}$MTc, $^{111}$in, $^{123}$I, $^{125}$I, $^{127}$Cs, $^{129}$Cs, $^{131}$I, $^{132}$I, $^{197}$Hg, $^{203}$Pb, or $^{206}$Bi.

In some aspects, the present invention provides methods of identifying a cancer inhibitor wherein the cancer is characterized by overexpression of a DKKL-1 splice product compared to a control. In some embodiments the methods comprise contacting a cell expressing a DKKL-1 splice product with a candidate compound, and determining whether a downstream marker of a DKKL-1 splice product is inhibited. In some embodiments inhibition of the downstream marker is indicative of a cancer inhibitor. In some embodiments the downstream marker is wnt or β-catenin.

In some aspects, the present invention provides methods for screening for a DKKL-1 splice product modulator comprising contacting a cell expressing a DKKL-1 splice product with a test compound and measuring an activity of a member of a Wnt pathway. In some embodiments, if the activity of the member of the Wnt pathway is modulated compared to a control, then the test compound is a DKKL-1 splice product modulator.

In some aspects, the present invention provides methods for determining the susceptibility of a patient to a DKKL-1 splice product modulator comprising detecting evidence of differential expression of a DKKL-1 splice product in the patient's cancer sample, wherein evidence of differential expression of a DKKL-1 splice product is indicative of the patient's susceptibility to a DKKL-1 splice product modulator of the invention. In some embodiments the DKKL-1 splice product is DKKL-1 isoform 2 or DKKL-1 isoform 3. In some embodiments evidence of differential expression of the DKKL-1 splice product is upregulation of the DKKL-1 splice product in the patient's cancer sample.

In some aspects, the present invention provides methods of purifying a DKKL-1 splice product from a sample comprising a DKKL-1 splice product comprising (a) providing an affinity matrix comprising an antibody of the invention bound to a solid support; b) contacting the sample with the affinity matrix to form an affinity matrix-DKKL-1 splice product complex; c) separating the affinity matrix-DKKL-1 splice product complex from the remainder of the sample; and d) releasing the DKKL-1 splice product from the affinity matrix. In some embodiments the DKKL-1 splice product is DKKL-1 isoform 2 or DKKL-1 isoform 3.

In some aspects, the present invention provides methods of delivering a cytotoxic agent or a diagnostic agent to one or more cells that express a DKKL-1 splice product. In some embodiments the methods comprise providing the cytotoxic agent or the diagnostic agent conjugated to an antibody or fragment thereof of the invention and exposing the cell to the antibody-agent or fragment-agent conjugate. In some embodiments the DKKL-1 splice product is DKKL-1 isoform 2 or DKKL-1 isoform 3. In some embodiments the cytotoxic agent is a chemotherapeutic agent.

In some aspects, the present invention provides methods for determining the prognosis of a cancer patient comprising determining the ratio of wild-type DKKL-1 expression products to DKKL-1 splice product expression products in a sample of the patient. In some embodiments the ratio of wild-type DKKL-1 expression products to DKKL-1 splice product expression products is used to determine the prognosis of the cancer patient. In some embodiments the wild-type DKKL-1 is encoded for by a nucleic acid having a sequence of SEQ ID NO: 1. In some embodiments the wild-type DKKL-1 has a sequence of SEQ ID NO:2. In some embodiments the DKKL-1 splice product is DKKL-1 isoform 2 or DKKL-1 isoform 3. In some embodiments a wild-type DKKL-1 expression product:DKKL-1 splice product expression product ratio of at least 2:1 is indicative of a patient with a good prognosis.

Other aspects of the invention will become apparent to the skilled artisan by the following description of the invention.

BRIEF DESCRIPTION OF THE FIGURES

FIGS. 3A-3E shows alignment of transcripts of splice variant isoforms of DKKL-1 by nucleotide sequence. The splice variant isoforms of DKKL-1 found in FIGS. 3A-3E listed by SEQ ID NO are as follows:
  hCT7238 ORF- SEQ ID NO. 19
  Sgrs0379-stop - SEQ ID NO. 20
  clone-379-R6 - SEQ ID NO. 21
  clone-379-R7 - SEQ ID NO. 22
  clone-379-R3 - SEQ ID NO. 23
  clone-379-RS2 - SEQ ID NO. 24
  clone-379-R8 - SEQ ID NO. 25
  clone-379-RS3 - SEQ ID NO. 26
  clone-379-R4 - SEQ ID NO. 27
  clone-379-R5 - SEQ ID NO. 28
  clone-379-R2 - SEQ ID NO. 29
  clone-379-RS7 - SEQ ID NO. 30
  clone-379-RS4 - SEQ ID NO. 31

FIGS. 4A-4B shows amino acid sequence alignment of transcripts of splice variant isoforms of DKKL-1. The splice variant isoforms of DKKL-1 found in FIGS. 4A-4B listed by SEQ ID NO are as follows:
  hCP35274.2- SEQ ID NO. 32
  Translation of DKKL-1 pending chris - SEQ ID NO. 33
  Translation of clone-379-R6 - SEQ ID NO. 34
  Translation of clone-379-R7 - SEQ ID NO. 35
  Translation of clone-379-R3 - SEQ ID NO. 36
  Translation of clone-379-RS2 - SEQ ID NO. 37
  Translation of clone-379-R8 - SEQ ID NO. 38
  Translation of clone-379-RS3 - SEQ ID NO 39
  Translation of clone-379-R4 - SEQ ID NO. 40
  Translation of clone-379-R5 - SEQ ID NO. 41
  Translation of clone-379-R2 - SEQ ID NO. 42
  Translation of clone-379-RS7 - SEQ ID NO. 43
  Translation of clone-379-RS4 - SEQ ID NO. 44

FIGS. 5A-5G show DKKL-1 expression levels in normal vs. tumor tissue samples (QPCR). Samples to the left of the vertical line are normal while samples to the right of the vertical lines are tumor samples.

DETAILED DESCRIPTION

Figure 1:
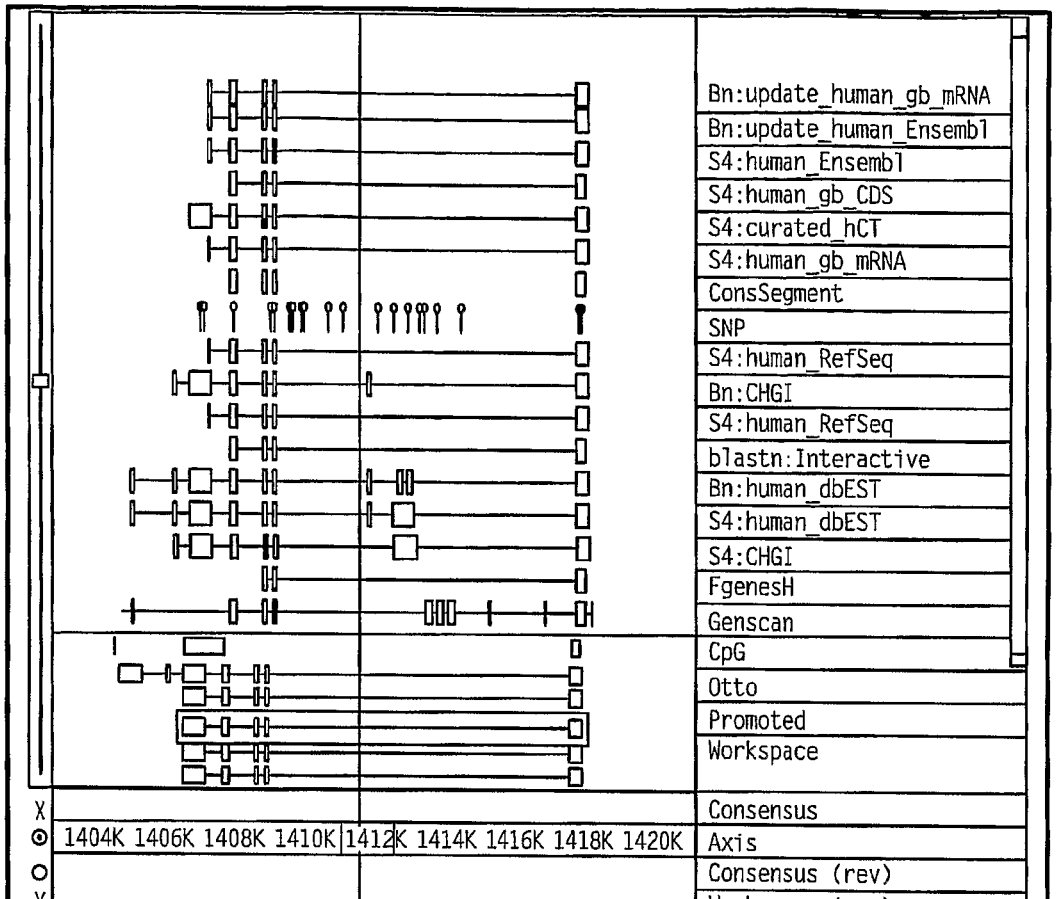
FIG. 1 shows alignment of Celera DKKL-1 transcript (SEQ ID NO.18) with the novel splice variants.

The inventors of the present application have discovered, inter alia, that DKKL-1 splice products are over-expressed in several cancers, including ovarian cancer, lung cancer, liver cancer, colon cancer, cervical cancer, breast cancer and lymphoma, and have restricted expression in normal tissues. Surprisingly, inhibition of DKKL-1 splice products inhibits activities of cancer cells, but not of "normal" cells. These and other aspects of the present invention are provided in the present application. Accordingly, the present invention provides, inter alia, compositions (e.g. "DKKL-1 splice product modulators") for treating, diagnosing and detecting cancers and methods for using such modulators.

Definitions

As used herein, the terms "DKKL-1", "novel isoforms", and "DKKL-1 splice products" refer to DKKL-1 isoform 2 and DKKL-1 isoform 3, described below.

As used herein, the terms "wild-type DKKL-1" and "DKKL-1 isoform 1" refer to DKKL-1 isoform 1 having a nucleotide sequence of SEQ ID NO:1 and an amino acid sequence of SEQ ID NO:2.

A "polynucleotide comprising novel isoform 2" comprises the novel splice junction comprising at least 4, 6, 10, 15, 20, 25, or 30 consecutive nucleotides spanning positions 329 and 330 of the nucleotide sequences of clones 379-R8 and 379-

RS3 shown in FIGS. 3A-3E and hybridizes to a DKKL-1 polynucleotide sequence or complement thereof. Sequences of clones 379-R8 and 379-RS3 shown in FIGS. 3A-3E and hybridize to a DKKL-1 polynucleotide sequence or complement thereof. The nucleotide sequence of isoform 2 is set forth as SEQ ID NO:3.

A "polynucleotide comprising novel isoform 3" comprises the novel splice junction comprising at least 4, 6, 10, 15, 20, 25, or 30 consecutive nucleotides spanning positions 188 and 189 of the nucleotide sequences of clones 379-R4, 379-R5, 379-R2, 379-RS7 and 379-RS4 shown in FIGS. 3A-3E and hybridizes to a DKKL-1 polynucleotide sequence, or complement thereof. The nucleotide sequence of isoform 3 is set forth as SEQ ID NO:5.

A "polypeptide comprising novel isoform 2" comprises the novel splice junction comprising at least 2, 4, 6, 8, 10, 12, 15, or 20 consecutive residues spanning positions 108 and 109 of the polypeptide sequences of clones 379-R8 and 379-RS3 shown in FIGS. 4A-4B and comprises a DKKL-1 polypeptide sequence or fragment thereof. The polypeptide sequence of isoform 2 is set forth as SEQ ID NO:4.

A "polypeptide comprising novel isoform 3" comprises the novel splice junction comprising at least 2, 4, 6, 8, 10, 12, 15, or 20 consecutive residues spanning positions 61 and 62 of the polypeptide sequences of clones 379-R4, 379-R5, 379-R2, 379-RS7 and 379-RS4 shown in FIGS. 4A-4B and comprises a DKKL-1 polypeptide sequence or fragment thereof. The polypeptide sequence of isoform 3 is set forth as SEQ ID NO:6.

As used herein, the term "modulator" refers to a composition that modulates one or more physiological or biochemical events associated with cancer. In some embodiments the modulator inhibits one or more biological activities associated with cancer. In some embodiments the modulator is a small molecule, an antibody, a mimetic, a soluble receptor, a decoy receptor or an oligonucleotide. In some embodiments the modulator acts by blocking ligand binding or by competing for a ligand-binding site. In some embodiments the modulator acts independently of ligand binding. In some embodiments the modulator blocks expression of a gene product involved in cancer. In some embodiments the modulator blocks a physical interaction of two or more biomolecules involved in cancer. In some embodiments modulators of the invention inhibit one or more DKKL-1 splice product activities. In some embodiments the modulator inhibits expression of one or more DKKL-1 splice products.

"Modulation of DKKL-1 splice product activities", as used herein, refers to an increase or decrease in DKKL-1 splice product activities that can be a result of, for example, interaction of an agent with a DKKL-1 splice product polynucleotide or polypeptide, inhibition of DKKL-1 splice product transcription and/or translation (e.g., through antisense or siRNA interaction with the DKKL-1 splice product, through modulation of transcription factors that facilitate DKKL-1 splice product expression), and the like. DKKL-1 splice product activity can be assessed by means including, without limitation, assessing DKKL-1 splice product polypeptide levels, or by assessing DKKL-1 splice product transcription levels. Comparisons of DKKL-1 splice product activities can also be accomplished by measuring levels of a DKKL-1 splice product downstream marker, measuring inhibition of DKKL-1 splice product signaling, measuring inhibition of cancer cell growth, measuring inhibition of tumor formation, measuring inhibition of cancer cell proliferation, measuring inhibition of metastasis, and measuring inhibition of tumor formation.

As used herein, the term "inhibit" refers to a reduction, decrease, inactivation or down-regulation of an activity or quantity. For example, in the context of the present invention, DKKL-1 splice product modulators may inhibit one or more of cancer cell growth, tumor formation, cancer cell proliferation, cancer cell metastasis, cell migration, angiogenesis, signaling, and expression. DKKL-1 splice product modulators may also one or more genes in the wnt pathway. DKKL-1 splice product modulators may also inhibit β-catenin activation and/or stabilization. Inhibition may be at least 25%, at least 30%, at least 40%, at least 50%, at least 60%, at least 70%, at least 75%, at least 80%, at least 90%, at least 95%, at least 97%, at least 98%, at least 99%, or 100%, as compared to a control.

In some embodiments the cancer is selected from the group consisting of ovarian cancer, lung cancer, liver cancer, colon cancer, cervical cancer, breast cancer or lymphoma. In some embodiments the lung cancer is mesothelioma or non-small cell lung cancer (NSCLC). In some embodiments the breast cancer is selected from the group consisting of ductal adenocarcinoma, lobular adenocarcinoma, and metastatic adenocarcinoma.

A "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, constituting at least about 0.5%, or at least about 5% by weight of the total protein in a given sample. A substantially pure protein comprises about 50-75%, about 80%, or about 90% by weight of the total protein. The definition includes the production of a cancer-associated protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

Nucleic acids of the present invention generally contains phosphodiester bonds, although in some cases, as outlined below (for example, in antisense applications or when a nucleic acid is a candidate drug agent), nucleic acid analogs may have alternate backbones, comprising, for example, phosphoramidate (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644, 048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done for a variety of reasons, for example to increase the stability and half-life of such molecules in physiological environments for use in anti-sense applications or as probes on a biochip.

As will be appreciated by those in the art, nucleic acid analogs may find use in the present invention. In addition, mixtures of naturally occurring nucleic acids and analogs can be made; alternatively, mixtures of different nucleic acid analogs, and mixtures of naturally occurring nucleic acids and analogs may be made.

The nucleic acids may be single stranded or double stranded, as specified, or contain portions of both double stranded or single stranded sequence. As will be appreciated by those in the art, the depiction of a single strand "Watson" also defines the sequence of the other strand "Crick"; thus the sequences described herein also includes the complement of the sequence. The nucleic acid may be DNA, both genomic and cDNA, RNA, or a hybrid, where the nucleic acid contains any combination of deoxyribo- and ribo-nucleotides, and any combination of bases, including uracil, adenine, thymine, cytosine, guanine, inosine, xanthine, hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

As used herein, the term "tag," "sequence tag" or "primer tag sequence" refers to an oligonucleotide with specific nucleic acid sequence that serves to identify a batch of polynucleotides bearing such tags therein. Polynucleotides from the same biological source are covalently tagged with a specific sequence tag so that in subsequent analysis the polynucleotide can be identified according to its source of origin. The sequence tags also serve as primers for nucleic acid amplification reactions.

A "microarray" is a linear or two-dimensional array of regions, each having a defined area, formed on the surface of a solid support. In some embodiments the regions are discrete regions. The density of the discrete regions on a microarray is determined by the total numbers of target polynucleotides to be detected on the surface of a single solid phase support, and is, in some embodiments, at least about 50/cm$^2$, at least about 100/cm$^2$, at least about 500/cm$^2$, and at least about 1,000/cm$^2$. As used herein, a DNA microarray is an array of oligonucleotide primers placed on a chip or other surfaces used to amplify or clone target polynucleotides. Since the position of each particular group of primers in the array is known, the identities of the target polynucleotides can be determined based on their binding to a particular position in the microarray.

A "linker" is a synthetic oligodeoxyribonucleotide that contains a restriction site. A linker may be blunt end-ligated onto the ends of DNA fragments to create restriction sites that can be used in the subsequent cloning of the fragment into a vector molecule.

The term "label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical, chemical, or any other appropriate means. The term "label" is used to refer to any chemical group or moiety having a detectable physical property or any compound capable of causing a chemical group or moiety to exhibit a detectable physical property, such as an enzyme that catalyzes conversion of a substrate into a detectable product. The term "label" also encompasses compounds that inhibit the expression of a particular physical property. The label may also be a compound that is a member of a binding pair, the other member of which bears a detectable physical property.

The term "support" refers to conventional supports such as beads, particles, dipsticks, fibers, filters, membranes, and silane or silicate supports such as glass slides. The term "amplify" is used in the broad sense to mean creating an amplification product which may include, for example, additional target molecules, or target-like molecules or molecules complementary to the target molecule, which molecules are created by virtue of the presence of the target molecule in the sample. In the situation where the target is a nucleic acid, an amplification product can be made enzymatically with DNA or RNA polymerases or reverse transcriptases.

As used herein, a "biological sample" refers to a sample of tissue or fluid isolated from an individual, including but not limited to, for example, blood, plasma, serum, spinal fluid, lymph fluid, skin, respiratory, intestinal and genitourinary tracts, tears, saliva, milk, cells (including but not limited to blood cells), tumors, organs, and also samples of in vitro cell culture constituents.

The term "biological sources" as used herein refers to the sources from which the target polynucleotides are derived. The source can be of any form of "sample" as described above, including but not limited to, cell, tissue or fluid. "Different biological sources" can refer to different cells/tissues/organs of the same individual, or cells/tissues/organs from different individuals of the same species, or cells/tissues/organs from different species.

DKKL-1 splice product proteins of the present invention are generally secreted proteins, the secretion of which can be either constitutive or regulated. These proteins have a signal peptide or signal sequence that targets the molecule to the secretory pathway. Secreted proteins are involved in numerous physiological events; by virtue of their circulating nature, they serve to transmit signals to various other cell types. The secreted protein may function in an autocrine manner (acting on the cell that secreted the factor), a paracrine manner (acting on cells in close proximity to the cell that secreted the factor) or an endocrine manner (acting on cells at a distance). Thus secreted molecules find use in modulating or altering numerous aspects of physiology. In some embodiments secreted proteins are used as targets for diagnostic markers, for example in blood tests.

Nucleic Acids of Novel Isoforms of DKKL-1

In some embodiments, the invention provides polynucleotides having at least 95% identity to the DKKL-1 splice products shown in FIGS. 3A-3E (SEQ ID NOS:3 and 5. In some embodiments, the invention provides polynucleotides having a sequence of SEQ ID NOS:3 and 5. Once isolated from its natural source, e.g., contained within a plasmid or other vector or excised therefrom as a linear nucleic acid segment, the recombinant nucleic acid can be further used as a probe to identify the expression of DKKL-1 splice variants. DKKL-1 splice products are discussed in U.S. Ser. No. 60/587,682, which is incorporated by reference in its entirety.

In some embodiments, nucleic acid probes hybridizable to polynucleotides comprising one or more of the novel isoforms 2 and 3 of DKKL-1 splice products are made and attached to biochips to be used in screening and diagnostic methods, or for gene therapy and/or antisense applications. In some embodiments, the polynucleotides comprising one or more of the novel isoforms 2 and 3 of DKKL-1 splice products that include coding regions of DKKL-1 can be put into expression vectors for the expression of proteins, again either for screening purposes or for administration to a patient.

DNA microarray technology makes it possible to conduct a large scale assay of a plurality of target nucleic acid molecules on a single solid phase support. U.S. Pat. No. 5,837,832 (Chee et al.) and related patent applications describe immobilizing an array of oligonucleotide probes for hybridization and detection of specific nucleic acid sequences in a sample. Target polynucleotides of interest isolated from a tissue of interest are hybridized to the DNA chip and the specific sequences detected based on the target polynucleotides' preference and degree of hybridization at discrete probe locations. One important use of arrays is in the analysis of differential gene expression, where the profile of expression of genes in different cells, often a cell of interest and a control cell, is compared and any differences in gene expression among the respective cells are identified. Such information is useful for the identification of the types of genes expressed in a particular cell or tissue type and diagnosis of cancer conditions based on the expression profile.

Typically, RNA from the sample of interest is subjected to reverse transcription to obtain labeled cDNA. See U.S. Pat. No. 6,410,229 (Lockhart et al.) The cDNA is then hybridized to oligonucleotides or cDNAs of known sequence arrayed on a chip or other surface in a known order. The location of the oligonucleotide to which the labeled cDNA hybridizes provides sequence information on the cDNA, while the amount of labeled hybridized RNA or cDNA provides an estimate of the relative representation of the RNA or cDNA of interest. See Schena, et al. Science 270:467-470 (1995). For example, use of a cDNA microarray to analyze gene expression patterns in human cancer is described by DeRisi, et al. (Nature Genetics 14:457-460 (1996)).

In some embodiments, nucleic acid probes corresponding to polynucleotides comprising one or more of the novel isoforms 2 and 3 of DKKL-1 splice products (both the nucleic acid sequences outlined in the figures and/or the complements thereof) are made. Typically, these probes are synthesized based on the disclosed sequences of this invention. The nucleic acid probes attached to the biochip are designed to be substantially complementary to the polynucleotides comprising one or more of the novel isoforms 2 and 3 of DKKL-1 splice products, i.e. the target sequence (either the target sequence of the sample or to other probe sequences, for example in sandwich assays), such that specific hybridization of the target sequence and the probes of the present invention occurs. As outlined below, this complementarity need not be perfect, in that there may be any number of base pair mismatches that will interfere with hybridization between the target sequence and the single stranded nucleic acids of the present invention. It is expected that the overall homology of the genes at the nucleotide level will be about 40% or greater about 60% or greater, about 80% or greater; about 90% or greater, about 95%, about 97% or greater, about 98% or greater, or 99% or greater, and, in addition, that there will be corresponding contiguous sequences of about 8-12 nucleotides or longer. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein. Whether or not a sequence is unique to polynucleotides comprising one or more of the novel isoforms 2 and 3 of DKKL-1 splice products according to this invention can be determined by techniques known to those of skill in the art. For example, the sequence can be compared to sequences in databanks, e.g., GenBank, to determine whether it is present in the uninfected host or other organisms. The sequence can also be compared to the known sequences of other viral agents, including those that are known to induce cancer.

A nucleic acid probe is generally single stranded but can be partly single and partly double stranded. The strandedness of the probe is dictated by the structure, composition, and properties of the target sequence. In general, the oligonucleotide probes range from about 6, 8, 10, 12, 15, 20, 30 to about 100 bases long, from about 10 to about 80 bases, or from about 30 to about 50 bases. In some embodiments entire genes are used as probes. In some embodiments, much longer nucleic acids can be used, up to hundreds of bases. The probes are sufficiently specific to hybridize to complementary template sequence under conditions known by those of skill in the art. In some embodiments the number of mismatches between the probes sequences and their complementary template (target) sequences to which they hybridize during hybridization generally do not exceed 15%, usually do not exceed 10% and do not exceed 5%, as determined by FASTA (default settings).

Oligonucleotide probes can include the naturally-occurring heterocyclic bases normally found in nucleic acids (uracil, cytosine, thymine, adenine and guanine), as well as modified bases and base analogues. Any modified base or base analogue compatible with hybridization of the probe to a target sequence is useful in the practice of the invention. The sugar or glycoside portion of the probe can comprise deoxyribose, ribose, and/or modified forms of these sugars, such as, for example, 2'-O-alkyl ribose. In some embodiments, the sugar moiety is 2'-deoxyribose; however, any sugar moiety that is compatible with the ability of the probe to hybridize to a target sequence can be used.

In some embodiments, the nucleoside units of the probe are linked by a phosphodiester backbone, as is well known in the art. In additional embodiments, internucleotide linkages can include any linkage known to one of skill in the art that is compatible with specific hybridization of the probe including, but not limited to phosphorothioate, methylphosphonate, sulfamate (e.g., U.S. Pat. No. 5,470,967) and polyamide (i.e., peptide nucleic acids). Peptide nucleic acids are described in Nielsen et al. (1991) *Science* 254: 1497-1500, U.S. Pat. No. 5,714,331, and Nielsen (1999) *Curr. Opin. Biotechnol.* 10:71-75.

In some embodiments, the probe is a chimeric molecule; i.e., can comprise more than one type of base or sugar subunit, and/or the linkages can be of more than one type within the same primer. The probe can comprise a moiety to facilitate hybridization to its target sequence, as are known in the art, for example, intercalators and/or minor groove binders. Variations of the bases, sugars, and internucleoside backbone, as well as the presence of any pendant group on the probe, will be compatible with the ability of the probe to bind, in a sequence-specific fashion, with its target sequence. A large number of structural modifications, both known and to be developed, are possible within these bounds. Advantageously, the probes according to the present invention may have structural characteristics such that they allow the signal amplification, such structural characteristics being, for example, branched DNA probes as those described by Urdea et al. (Nucleic Acids Symp. Ser., 24:197-200 (1991)) or in the European Patent No. EP-0225,807. Moreover, synthetic methods for preparing the various heterocyclic bases, sugars, nucleosides and nucleotides that form the probe, and preparation of oligonucleotides of specific predetermined sequence, are well-developed and known in the art. In some embodiments the method for oligonucleotide synthesis incorporates the teaching of U.S. Pat. No. 5,419,966.

Probes may be in solution, such as in wells or on the surface of a micro-array, or attached to a solid support. Examples of solid support materials that can be used include a plastic, a ceramic, a metal, a resin, a gel and a membrane. Useful types of solid supports include plates, beads, magnetic material, microbeads, hybridization chips, membranes, crystals, ceramics and self-assembling monolayers. Some embodiments comprise a two-dimensional or three-dimensional matrix, such as a gel or hybridization chip with multiple probe binding sites (Pevzner et al., J. Biomol. Struc. & Dyn. 9:399-410, 1991; Maskos and Southern, Nuc. Acids Res. 20:1679-84, 1992). Hybridization chips can be used to construct very large probe arrays that are subsequently hybridized with a target nucleic acid. Analysis of the hybridization pattern of the chip can assist in the identification of the target nucleotide sequence. Patterns can be manually or computer analyzed, but it is clear that positional sequencing by hybridization lends itself to computer analysis and automation. Algorithms and software, which have been developed for sequence reconstruction, are applicable to the methods described herein (R. Drmanac et al., J. Biomol. Struc. & Dyn. 5:1085-1102, 1991; P. A. Pevzner, J. Biomol. Struc. & Dyn. 7:63-73, 1989).

As will be appreciated by those in the art, nucleic acids can be attached or immobilized to a solid support in a wide variety of ways. By "immobilized" herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of electrostatic, hydrophilic, and hydrophobic interactions. Included in non-covalent binding is the covalent attachment of a molecule, such as streptavidin, to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

Nucleic acid probes may be attached to the solid support by covalent binding such as by conjugation with a coupling agent or by, covalent or non-covalent binding such as electrostatic interactions, hydrogen bonds or antibody-antigen coupling, or by combinations thereof. Typical coupling agents include biotin/avidin, biotin/streptavidin, *Staphylococcus aureus* protein A/IgG antibody $F_c$ fragment, and streptavidin/protein A chimeras (T. Sano and C. R. Cantor, Bio/Technology 9:1378-81 (1991)), or derivatives or combinations of these agents. Nucleic acids may be attached to the solid support by a photocleavable bond, an electrostatic bond, a disulfide bond, a peptide bond, a diester bone or a combination of these sorts of bonds. The array may also be attached to the solid support by a selectively releasable bond such as 4,4'-dimethoxytrityl or its derivative. Derivatives which have been found to be useful include 3 or 4 [bis-(4-methoxyphenyl)]-methyl-benzoic acid, N-succinimidyl-3 or 4 [bis-(4-methoxyphenyl)]-methyl-benzoic acid, N-succinimidyl-3 or 4 [bis-(4-methoxyphenyl)]-hydroxymethyl-benzoic acid, N-succinimidyl-3 or 4 [bis-(4-methoxyphenyl)]-chloromethyl-benzoic acid, and salts of these acids.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. The solid phase support of the present invention can be of any solid materials and structures suitable for supporting nucleotide hybridization and synthesis. In some embodiments, the solid phase support comprises at least one substantially rigid surface on which the primers can be immobilized and the reverse transcriptase reaction performed. The substrates with which the polynucleotide microarray elements are stably associated may be fabricated from a variety of materials, including plastics, ceramics, metals, acrylamide, cellulose, nitrocellulose, glass, polystyrene, polyethylene vinyl acetate, polypropylene, polymethacrylate, polyethylene, polyethylene oxide, polysilicates, polycarbonates, Teflon®, fluorocarbons, nylon, silicon rubber, polyanhydrides, polyglycolic acid, polylactic acid, polyorthoesters, polypropylfumerate, collagen, glycosaminoglycans, and polyamino acids. Substrates may be two-dimensional or three-dimensional in form, such as gels, membranes, thin films, glasses, plates, cylinders, beads, magnetic beads, optical fibers, woven fibers, etc. In some embodiments the array is a three-dimensional array. In some embodiments the three-dimensional array is a collection of tagged beads. Each tagged bead has different primers attached to it. Tags are detectable by signaling means such as color (Luminex, Illumina) and electromagnetic field (Pharmaseq) and signals on tagged beads can even be remotely detected (e.g., using optical fibers). The size of the solid support can be any of the standard microarray sizes, useful for DNA microarray technology, and the size may be tailored to fit the particular machine being used to conduct a reaction of the invention. In general, the substrates allow optical detection and do not appreciably fluoresce.

In some embodiments, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups. In some embodiments the biochip is derivatized with amino groups. Using these functional groups, the probes can be attached using functional groups on the probes. For example, nucleic acids containing amino groups can be attached to surfaces comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference). In addition, in some cases, additional linkers, such as alkyl groups (including substituted and heteroalkyl groups) may be used.

In some embodiments, the oligonucleotides are synthesized as is known in the art, and then attached to the surface of the solid support. As will be appreciated by those skilled in the art, either the 5' or 3' terminus may be attached to the solid support, or attachment may be via an internal nucleoside. In some embodiments, the immobilization to the solid support may be very strong, yet non-covalent. For example, biotinylated oligonucleotides can be made, which bind to surfaces covalently coated with streptavidin, resulting in attachment.

The arrays may be produced according to any convenient methodology, such as preforming the polynucleotide microarray elements and then stably associating them with the surface of the solid support. In some embodiments, the oligonucleotides may be synthesized on the surface, as is known in the art. A number of different array configurations and methods for their production are known to those of skill in the art and disclosed in WO 95/25116 and WO 95/35505 (photolithographic techniques), U.S. Pat. No. 5,445,934 (in situ synthesis by photolithography), U.S. Pat. No. 5,384,261 (in situ synthesis by mechanically directed flow paths); and U.S. Pat. No. 5,700,637 (synthesis by spotting, printing or coupling); the disclosure of which are herein incorporated in their entirety by reference. Another method for coupling DNA to beads uses specific ligands attached to the end of the DNA to link to ligand-binding molecules attached to a bead. Possible ligand-binding partner pairs include biotin-avidin/streptavidin, or various antibody/antigen pairs such as digoxygenin-antidigoxygenin antibody (Smith et al., "Direct Mechanical Measurements of the Elasticity of Single DNA Molecules by Using Magnetic Beads," Science 258:1122-1126 (1992)). Covalent chemical attachment of DNA to the support can be accomplished by using standard coupling agents to link the 5'-phosphate on the DNA to coated microspheres through a phosphoamidate bond. Methods for immobilization of oligonucleotides to solid-state substrates are well established. See Pease et al., Proc. Natl. Acad. Sci. USA 91(11):5022-5026 (1994). In some embodiments oligonucleotides are attached to solid-state substrates as described by Guo et al., Nucleic Acids Res. 22:5456-5465 (1994). Immobilization can be accomplished either by in situ DNA synthesis (Maskos and Southern, Nucleic Acids Research, 20:1679-1684 (1992) or by covalent attachment of chemically synthesized oligonucleotides (Guo et al., supra) in combination with robotic arraying technologies.

In addition to the solid-phase technology represented by biochip arrays, gene expression can also be quantified using liquid-phase arrays. One such system is kinetic polymerase chain reaction (PCR). Kinetic PCR allows for the simultaneous amplification and quantification of specific nucleic acid sequences. The specificity is derived from synthetic oligonucleotide primers designed to preferentially adhere to single-stranded nucleic acid sequences bracketing the target site. This pair of oligonucleotide primers form specific, non-covalently bound complexes on each strand of the target sequence. These complexes facilitate in vitro transcription of double-stranded DNA in opposite orientations. Temperature cycling of the reaction mixture creates a continuous cycle of primer binding, transcription, and re-melting of the nucleic acid to individual strands. The result is an exponential increase of the target dsDNA product. This product can be quantified in real time either through the use of an intercalating dye or a sequence specific probe. SYBR® Greene I, is an example of an intercalating dye that preferentially binds to dsDNA resulting in a concomitant increase in the fluorescent signal. Sequence specific probes, such as used with TaqMan® technology, consist of a fluorochrome and a quenching molecule covalently bound to opposite ends of an oligonucleotide. The probe is designed to selectively bind the target DNA sequence between the two primers. When the DNA strands are synthesized during the PCR reaction, the fluorochrome is cleaved from the probe by the exonuclease activity of the polymerase resulting in signal dequenching. The probe signaling method can be more specific than the intercalating dye method, but in each case, signal strength is proportional to the dsDNA product produced. Each type of quantification method can be used in multi-well liquid phase arrays with each well representing primers and/or probes specific to nucleic acid sequences of interest. When used with messenger RNA preparations of tissues or cell lines, an array of probe/primer reactions can simultaneously quantify the expression of multiple gene products of interest. See Germer, S., et al., Genome Res. 10:258-266 (2000); Heid, C. A., et al., Genome Res. 6, 986-994 (1996).

Expression of Novel Isoforms of DKK-1 Protein

In some embodiments, the invention provides nucleic acids encoding polypeptides having at least 95% identity to the DKKL-1 splice products shown in FIGS. 4A-4B (SEQ ID NOS:4 and 6). In some embodiments, the invention provides nucleic acids encoding polypeptides having a sequence of SEQ ID NOS:4 or 6. In some embodiments, nucleic acids encoding polypeptides comprising one or more of the novel isoforms 2 and 3 of DKKL-1 splice products shown in FIGS. 4A-4B are used to make a variety of expression vectors to express the proteins which can then be used in screening assays, as described below. In some embodiments the polypeptides comprise the novel splice junction comprising at least 2, 4, 6, 8, 10, 12, 15, or 20 consecutive residues spanning positions 108 and 109 of the polypeptide sequences of clones 379-R8 and 379-RS3 shown in FIGS. 4A-4B, or the novel splice junction comprising at least 2, 4, 6, 8, 10, 12, 15, or 20 consecutive residues spanning positions 61 and 62 of the polypeptide sequences of clones 379-R4, 379-R5, 379-R2, 379-RS7 and 379-RS4 shown in FIGS. 4A-4B.

The expression vectors may be either self-replicating extrachromosomal vectors or vectors which integrate into a host genome. Generally, these expression vectors include transcriptional and translational regulatory nucleic acid operably linked to the nucleic acid encoding the protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice. The transcriptional and translational regulatory nucleic acid will generally be appropriate to the host cell used to express the protein. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In some embodiments, the regulatory sequences include a promoter and transcriptional start and stop sequences. Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and, in some embodiment, two homologous sequences that flank the expression construct. The integrating vector may be directed to a specific locus in the host cell by selecting the appropriate homologous sequence for inclusion in the vector. Constructs for integrating vectors are well known in the art.

In addition, in some embodiments, the expression vector contains a selectable marker gene to allow the selection of transformed host cells. Selection genes are well known in the art and will vary with the host cell used.

In some embodiments the proteins of the present invention are produced by culturing a host cell transformed with an expression vector containing nucleic acid encoding polypeptides comprising one or more of the novel DKKL-1 splice products, under the appropriate conditions to induce or cause expression of the polypeptide. The conditions appropriate for protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect, plant and animal cells, including mammalian cells. Of particular interest are *Drosophila melanogaster* cells, *Saccharomyces cerevisiae* and other yeasts, *E. coli*, *Bacillus subtilis*, Sf9 cells, C129 cells, 293 cells, *Neurospora*, BHK, CHO, COS, HeLa cells, THP1 cell line (a macrophage cell line) and human cells and cell lines.

In some embodiments, the polypeptides comprising one or more of the DKKL-1 splice products are expressed in mammalian cells. Mammalian expression systems are also known in the art, and include retroviral systems. In some embodiments the expression vector system is a retroviral vector system such as is generally described in PCT/US97/01019 and PCT/US97/01048, both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenylation signals include those derived form SV40.

Methods of introducing exogenous nucleic acid into mammalian hosts, as well as other hosts, are well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In some embodiments, the proteins are expressed in bacterial systems. Bacterial expression systems are well known in the art. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the protein in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes that render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris*, and *Streptococcus lividans*, among others. The bacterial expression vectors are transformed into bacterial host cells using techniques well known in the art, such as calcium chloride treatment, electroporation, and others.

In some embodiments, proteins are produced in insect cells. Expression vectors for the transformation of insect cells, and in particular, baculovirus-based expression vectors, are well known in the art.

In some embodiments, protein is produced in yeast cells. Yeast expression systems are well known in the art, and include expression vectors for *Saccharomyces cerevisiae*,

*Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.*

The polypeptides comprising one or more of the novel DKKL-1 splice products may also be made as fusion proteins, using techniques well known in the art, for example, for the creation of monoclonal antibodies. If the desired epitope is small, the protein may be fused to a carrier protein to form an immunogen. Alternatively, the protein may be made as a fusion protein to increase expression, or for other reasons.

In some embodiments, the nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the nucleic acids, proteins and antibodies at any position. For example, the label should be capable of producing, either directly or indirectly, a detectable signal. The detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the label may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982).

In general, the term "polypeptide" as used herein refers to both the full-length polypeptide encoded by the recited polynucleotide, the polypeptide encoded by the gene represented by the recited polynucleotide, as well as portions or fragments thereof.

The present invention includes variants of DKKL-1 splice products including mutants, fragments, and fusions thereof. Mutants can include amino acid substitutions, additions or deletions. The amino acid substitutions can be conservative amino acid substitutions or substitutions to eliminate nonessential amino acids, such as to alter a glycosylation site, a phosphorylation site or an acetylation site, or to minimize misfolding by substitution or deletion of one or more cysteine residues that are not necessary for function. Conservative amino acid substitutions are those that preserve the general charge, hydrophobicity/hydrophilicity, and/or steric bulk of the amino acid substituted. Variants can be designed so as to retain or have enhanced biological activity of a particular region of the protein (e.g., a functional domain and/or, where the polypeptide is a member of a protein family, a region associated with a consensus sequence). Selection of amino acid alterations for production of variants can be based upon the accessibility (interior vs. ekterior) of the amino acid (see, e.g., Go et al, *Int. J Peptide Protein Res.* (1980) 15:211), the thermostability of the variant polypeptide (see, e.g., Querol et al., *Prot. Eng.* (1996) 9:265), desired glycosylation sites (see, e.g., Olsen and Thomsen, *J. Gen. Microbiol.* (1991) 137:579), desired disulfide bridges (see, e.g., Clarke et al., *Biochemistiy* (1993) 32:4322; and Wakarchuk et al., *Protein Eng.* (1994) 7:1379), desired metal binding sites (see, e.g., Toma et al., *Biochemistry* (1991) 30:97, and Haezerbrouck et al., *Protein Eng.* (1993) 6:643), and desired substitutions within proline loops (see, e.g., Masul et al., *Appl. Env. Microbiol.* (1994) 60:3579). Cysteine-depleted muteins can be produced as disclosed in U.S. Pat. No. 4,959,314.

Variants also include fragments of the polypeptides disclosed herein, particularly biologically active fragments and/or fragments corresponding to functional domains. Fragments of interest will typically be at least about 8 amino acids (aa) 10 aa, 15 aa, 20 aa, 25 aa, 30 aa, 35 aa, 40 aa, to at least about 45 aa in length, usually at least about 50 aa in length, at least about 75 aa, at least about 100 aa, at least about 125 aa, at least about 150 aa in length, at least about 200 aa, at least about 300 aa, at least about 400 aa and can be as long as 500 aa in length or longer, but will usually not exceed about 1000 aa in length, where the fragment will have a stretch of amino acids that is identical to a polypeptide encoded by a polynucleotide having a sequence of any one of the polynucleotide sequences provided herein, or a homolog thereof. The protein variants described herein are encoded by polynucleotides that are within the scope of the invention. The genetic code can be used to select the appropriate codons to construct the corresponding variants.

In some embodiments, polypeptides of the present invention have at least about 60%, at least about 70%, at least about 80%, at least about 85%, at least about 90%, at least about at least 92%, at least about 94%, at least about 95%, at least about 97%, at least about 98%, at least about 99% and about 100% homology to SEQ ID NO:4 or 6, or a portion thereof.

Covalent modifications of polypeptides comprising one or more of the novel DKKL-1 splice products are included within the scope of this invention. One type of covalent modification includes reacting targeted amino acid residues of a polypeptide with an organic derivatizing agent that is capable of reacting with selected side chains or the N- or C-terminal residues of a polypeptide. Derivatization with bifunctional agents is useful, for instance, for crosslinking polypeptides to a water-insoluble support matrix or surface for use in the method for purifying anti-DKKL-1 antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl, threonyl or tyrosyl residues, methylation of the a-amino groups of lysine, arginine, and histidine side chains [T. E. Creighton, Proteins: Structure and Molecular Properties, W.H. Freeman & Co., San Francisco, pp. 79-86 (1983)], acetylation of the N-terminal amine, and amidation of any C-terminal carboxyl group.

Another type of covalent modification comprises linking the polypeptide to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

Polypeptides comprising one or more of the novel DKKL-1 splice products may be modified to form chimeric molecules comprising a polypeptide fused to another, heterologous polypeptide or amino acid sequence. In some embodiments such a chimeric molecule comprises a fusion of a polypeptide with a tag polypeptide that provides an epitope to which an anti-tag antibody can selectively bind. The epitope tag is generally placed at the amino- or carboxyl-terminus of the polypeptide, although internal fusions may also be tolerated in some instances. The presence of such epitope-tagged forms of a polypeptide can be detected using an antibody against the tag polypeptide. Also, provision of the epitope tag enables the polypeptide to be readily purified by affinity purification using an anti-tag antibody or another type of affinity matrix that binds to the epitope tag. In an alternative embodiment, the chimeric molecule may comprise a fusion of a polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E1, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; tubulin epitope peptide [Skinner et al., J. Biol. Chem., 266: 15163-15166 (1991)]; and the T7 gene 10 protein peptide tag [Lutz-Freyermuth et al., Proc. Natl. Acad. Sci. USA, 87:6393-6397 (1990)].

Novel DKKL-1 Antigens and Antibodies Thereto

In some embodiments, the invention provides antibodies which specifically bind to a polypeptide of the present invention. In some embodiments the antibodies specifically bind to polypeptides having a sequence at least 95% identical to SEQ D NO:4 or SEQ ID NO:6. In some embodiments, the polypeptide is DKKL-1 isoform 2 and/or DKKL-1 isoform 3. In some embodiments the antibodies specifically bind to polypeptides having a sequence of SEQ ID NO:4 or SEQ ID NO:6. In some embodiments, the polypeptide has at least one epitope or determinant comprising the novel splice junction comprising at least 2, 4, 6, 8, 10, 12, 15, or 20 consecutive residues spanning positions 108 and 109 of the polypeptide sequences of clones 379-R8 and 379-RS3 shown in FIGS. 4A-4B or the novel splice junction comprising at least 2, 4, 6, 8, 10, 12, 15, or 20 consecutive residues spanning positions 61 and 62 of the polypeptide sequences of clones 379-R4, 379-R5, 379-R2, 379-RS7 and 379-RS4 shown in FIGS. 4A-4B. By "epitope" or "determinant" herein is meant a portion of a protein that will generate and/or bind an antibody or T-cell receptor in the context of MHC.

Antibodies are defined to be "specifically binding" if: 1) they exhibit a threshold level of binding activity, and/or 2) they do not significantly cross-react with known related polypeptide molecules. The binding affinity of an antibody can be readily determined by one of ordinary skill in the art, for example, by Scatchard analysis (Scatchard, Ann. NY Acad. Sci. 51: 660-672, 1949). In some embodiments the antibodies of the present invention bind to their target epitopes or mimetic decoys at least $10^3$, at least $10^4$, at least $10^5$, and at least $10^6$ fold higher than to other known members of the human Dickkopf family, including, for example, wild-type DKKL-1.

In some embodiments, the antibodies of the present invention do not bind to known related polypeptide molecules, for example, if they bind a DKKL-1 splice product but not known related polypeptides using a standard Western blot analysis (Ausubel et al.). In some embodiments the antibodies bind to DKKL-1 isoform 2 and DKKL-1 isoform 3 but do not specifically bind to DKKL-1 isoform 1. In some embodiments the antibodies bind to DKKL-1 isoform 2 but do not specifically bind to DKKL-1 isoform 1 or DKKL-1 isoform 3. In some embodiments the antibodies bind to DKKL-1 isoform 3 but do not specifically bind to DKKL-1 isoform 1 or DKKL-1 isoform 2.

In some embodiments the antibodies bind with high affinity of $10^{-4}$M or less, $10^{-7}$M or less, $10^{-9}$M or less or with subnanomolar affinity (0.9, 0.8, 0.7, 0.6, 0.5, 0.4, 0.3, 0.2, 0.1 nM or even less). In some embodiments, the epitope is unique; that is, antibodies generated to a unique epitope show little or no cross-reactivity.

In some embodiments, the antibodies of the present invention bind to orthologs, homologs, paralogs or variants, or combinations and subcombinations thereof, of the DKKL-1 polypeptides of the present invention. In some embodiments, the antibodies of the present invention bind to orthologs of DKKL-1 polypeptides. In some embodiments, the antibodies of the present invention bind to homologs of DKKL-1 polypeptides. In some embodiments, the antibodies of the present invention bind to paralogs of DKKL-1 polypeptides. In some embodiments, the antibodies of the present invention bind to variants of DKKL-1 polypeptides. In some embodiments, the antibodies of the present invention do not bind to orthologs, homologs, paralogs or variants, or combinations and subcombinations thereof, of DKKL-1 polypeptides.

Polypeptides comprising one or more of the novel isoforms 2 and 3 of DKKL-1 splice products shown in FIGS. 4A-4B may be analyzed to determine certain preferred regions of the polypeptide. Regions of high antigenicity are determined from data by DNASTAR analysis by choosing values that represent regions of the polypeptide that are likely to be exposed on the surface of the polypeptide in an environment in which antigen recognition may occur in the process of initiation of an immune response. For example, the amino acid sequence of a polypeptide may be analyzed using the default parameters of the DNASTAR computer algorithm (DNASTAR, Inc., Madison Wis;).

Polypeptide features that may be routinely obtained using the DNASTAR computer algorithm include, but are not limited to, Garnier-Robson alpha-regions, beta-regions, turn-regions, and coil-regions (Garnier et al. J. Mol. Biol., 120: 97 (1978)); Chou-Fasman alpha-regions, beta-regions, and turn-regions (Adv. in Enzymol., 47:45-148 (1978)); Kyte-Doolittle hydrophilic regions and hydrophobic regions (J. Mol. Biol., 157:105-132 (1982)); Eisenberg alpha- and beta-amphipathic regions; Karplus-Schulz flexible regions; Emini surface-forming regions (J. Virol., 55(3):836-839 (1985)); and Jameson-Wolf regions of high antigenic index (CABIOS, 4(1):181-186 (1988)). Kyte-Doolittle hydrophilic regions and hydrophobic regions, Emini surface-forming regions, and Jameson-Wolf regions of high antigenic index (i.e., containing four or more contiguous amino acids having an antigenic index of greater than or equal to 1.5, as identified using the default parameters of the Jameson-Wolf program) can routinely be used to determine polypeptide regions that exhibit a high degree of potential for antigenicity. One approach for preparing antibodies to a protein is the selection and preparation of an amino acid sequence of all or part of the protein, chemically synthesizing the sequence and injecting it into an appropriate animal, typically a rabbit, hamster or a mouse. Oligopeptides can be selected as candidates for the production of an antibody to the protein based upon the oligopeptides lying in hydrophilic regions, which are thus likely to be exposed in the mature protein. Additional oligopeptides can be determined using, for example, the Antigenicity Index, Welling, G. W. et al., FEBS Lett. 188:215-218 (1985), incorporated herein by reference.

In some embodiments, the term "antibody" includes antibody fragments, as are known in the art, including Fab, Fab$_2$, single chain antibodies (Fv for example), chimeric antibodies, etc., either produced by the modification of whole antibodies or those synthesized de novo using recombinant DNA technologies.

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of the figures or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, in some embodiments, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a polypeptide encoded by a nucleic acid of the novel DKKL-1 isoform sequences, or fragment thereof or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that in some embodiments contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Monoclonal antibody technology is used in implementing research, diagnosis and therapy. Monoclonal antibodies are used in radioimmunoassays, enzyme-linked immunosorbent assays, immunocytopathology, and flow cytometry for in vitro diagnosis, and in vivo for diagnosis and immunotherapy of human disease. Waldmann, T. A. (1991) Science 252:1657-1662. In particular, monoclonal antibodies have been widely applied to the diagnosis and therapy of cancer, wherein it is desirable to target malignant lesions while avoiding normal tissue. See, e.g., U.S. Pat. Nos. 4,753,894 to Frankel, et al.; 4,938,948 to Ring et al.; and 4,956,453 to Bjorn et al.

In some embodiments, it may be desirable to modify the DKKL-1 modulator with respect to effector function, e.g. so as to enhance antigen-dependent cell-mediated cyotoxicity (ADCC) and/or complement dependent cytotoxicity (CDC) of the neutralizing agent. This may be achieved, for example, by introducing one or more amino acid substitutions in an Fc region of an antibody neutralizing agent. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

In some embodiments, the antibodies are bispecific antibodies. Bispecific antibodies are monoclonal, in some embodiments human or humanized, antibodies that have binding specificities for at least two different antigens. A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349: 293-299; Lobuglio et al. (1989) Proc. Nat. Acad. Sci. USA 86:4220-4224; Shaw et al. (1987) J Immunol. 138:4534-4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients. In the present case, one of the binding specificities is for a protein encoded by a nucleic acid of the novel DKKL-1 isoform sequences, or a fragment thereof, the other one is for any other antigen, and, in some embodiments, for a cell-surface protein or receptor or receptor subunit, which, in some embodiments, is tumor specific.

In some embodiments, the antibodies to polypeptides comprising one or more of the novel isoforms 2 and 3 of DKKL-1 splice products shown in FIGS. 4A-4B are capable of reducing or eliminating the biological function of the polypeptide. Generally, the antibodies cause at least a 25% decrease, at least a 30% decrease, at least a 40% decrease, at least about 50% decrease in activity, and about a 95-100% decrease in activity.

In some embodiments the antibodies inhibit a cancer cell activity selected from the group consisting of cancer cell proliferation, cancer cell growth, cancer cell migration, cancer cell metastasis, tumorigenicity and cancer cell survival. In some embodiments the antibodies inhibit one or more of β-catenin signaling and Wnt signaling. In some embodiments the antibodies modulate stabilization and/or activation of β-catenin. In some embodiments the antibodies inhibit the activity by at least 30% as compared to a control.

In some embodiments the antibodies are humanized antibodies. "Humanized" antibodies refer to a molecule having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Alternatively, a humanized antibody may be derived from a chimeric antibody that retains or substantially retains the antigen-binding properties of the parental, non-human, antibody but which exhibits diminished immunogenicity as compared to the parental antibody when administered to humans. The phrase "chimeric antibody," as used herein, refers to an antibody containing sequence derived from two different antibodies (see, e.g., U.S. Pat. No. 4,816,567) that typically originate from different species. Typically, in these chimeric antibodies, the variable region of both light and heavy chains mimics the variable regions of antibodies derived from one species of mammals, while the constant portions are homologous to the sequences in antibodies derived from another. Most typically, chimeric antibodies comprise human and murine antibody fragments, generally human constant and mouse variable regions. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework residues (FR) regions are those of a human immunoglobulin consensus sequence. The humanized antibody optimally also will comprise at least a portion of an immunoglobulin constant region (Fc), typically that of a human immunoglobulin (Jones et al., *Nature,* 321: 522-525 (1986); Riechmann et al., *Nature,* 332:323-329 (1988); and Presta, *Curr. Op. Struct. Biol.,* 2:593-596 (1992)). One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

Because humanized antibodies are far less immunogenic in humans than the parental mouse monoclonal antibodies, they can be used for the treatment of humans with far less risk of anaphylaxis. Thus, in some embodiments humanized antibodies are used in therapeutic applications that involve in vivo administration to a human such as, e.g., use as radiation sensitizers for the treatment of neoplastic disease or use in methods to reduce the side effects of, e.g., cancer therapy. Methods for humanizing non-human antibodies are well known in the art. Generally, a humanized antibody has one or more amino acid residues introduced into it from a source that is non-human. These non-human amino acid residues are often referred to as import residues, which are typically taken from an import variable domain. Humanization can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies [Cole et al., Monoclonal Antibodies and Cancer Therapy, Alan R. Liss, p. 77 (1985) and Boerner et al., J. Immunol., 147(1):86-95 (1991)]. Humanized antibodies may be achieved by a variety of methods including, for example: (1) grafting the non-human complementarity determining regions (CDRs) onto a human framework and constant region (a process referred to in the art as "humanizing"), or, alternatively, (2) transplanting the entire non-human variable domains, but "cloaking" them with a human-like surface by replacement of surface residues (a process referred to in the art as "veneering"). In the present invention, humanized antibodies will include both "humanized" and "veneered" antibodies. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995); Jones et al., *Nature* 321:522-525 (1986); Morrison et al., *Proc. Natl. Acad. Sci,* U.S.A., 81:6851-6855 (1984); Morrison and Oi, *Adv. Immunol.,* 44:65-92 (1988); Verhoeyer et al., *Science* 239:1534-1536 (1988); Padlan, *Molec. Immun.* 28:489-498 (1991); Padlan, *Molec. Immunol.* 31(3):169-217 (1994); and Kettleborough, C. A. et al., *Protein Eng.* 4(7): 773-83 (1991) each of which is incorporated herein by reference.

The phrase "complementarity determining region" refers to amino acid sequences which together define the binding affinity and specificity of the natural Fv region of a native immunoglobulin binding site. See, e.g., Chothia et al., *J. Mol. Biol.* 196:901-917 (1987); Kabat et al., U.S. Dept. of Health and Human Services NIH Publication No. 91-3242 (1991).

The phrase "constant region" refers to the portion of the antibody molecule that confers effector functions. In the present invention, mouse constant regions are substituted by human constant regions. The constant regions of the subject humanized antibodies are derived from human immunoglobulins. The heavy chain constant region can be selected from any of the five isotypes: alpha, delta, epsilon, gamma or mu. One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region that disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors. See, e.g., U.S. Pat. Nos. 5,530,101 and 5,585,089 which are incorporated herein by reference.

Humanized antibodies can also be produced using transgenic animals that are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody-producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein.

In the present invention, polypeptides of the invention and variants thereof can be used to immunize a transgenic animal as described above. Monoclonal antibodies are made using methods known in the art, and the specificity of the antibodies is tested using isolated polypeptides. Methods for preparation of the human or primate polypeptide or an epitope thereof include, but are not limited to chemical synthesis, recombinant DNA techniques or isolation from biological samples. Chemical synthesis of a peptide can be performed, for example, by the classical Merrifeld method of solid phase peptide synthesis (Merrifeld, *J. Am. Chem. Soc.* 85:2149, 1963 which is incorporated by reference) or the FMOC strategy on a Rapid Automated Multiple Peptide Synthesis system (E. I. du Pont de Nemours Company, Wilmington, Del.) (Caprino and Han, *J. Org. Chem.* 37:3404, 1972 which is incorporated by reference).

Polyclonal antibodies can be prepared by immunizing rabbits or other animals by injecting antigen followed by subsequent boosts at appropriate intervals. The animals are bled and sera assayed against purified proteins usually by ELISA or by bioassay based upon the ability to block the action of proteins. When using avian species, e.g., chicken, turkey and the like, the antibody can be isolated from the yolk of the egg. Monoclonal antibodies can be prepared after the method of Milstein and Kohler by fusing splenocytes from immunized mice with continuously replicating tumor cells such as myeloma or lymphoma cells. (Milstein and Kohler, *Nature* 256:495-497, 1975; Gulfre and Milstein, *Methods in Enzymology: Immunochemical Techniques* 73:1-46, Langone and Banatis eds., Academic Press, 1981 which are incorporated by reference). The hybridoma cells so formed are then cloned by limiting dilution methods and supernatants assayed for antibody production by ELISA, RIA or bioassay.

The unique ability of antibodies to recognize and specifically bind to target proteins provides an approach for treating an overexpression of the protein. Thus, another aspect of the present invention provides for a method for preventing or treating diseases involving overexpression of a polypeptide by treatment of a patient with specific antibodies to the protein.

Specific antibodies, either polyclonal or monoclonal, to the proteins can be produced by any suitable method known in the art as discussed above. For example, murine or human monoclonal antibodies can be produced by hybridoma technology or, alternatively, the polypeptides comprising one or more of the novel isoforms 2 and 3 of DKKL-1 splice products shown in FIGS. 4A-4B, or an immunologically active fragment thereof, or an anti-idiotypic antibody, or fragment thereof can be administered to an animal to elicit the production of antibodies capable of recognizing and binding to the proteins. Such antibodies can be from any class of antibodies including, but not limited to IgG, IgA, IgM, IgD, and IgE or in the case of avian species, IgY and from any subclass of antibodies.

In some embodiments, oncogenes which encode secreted growth factors may be inhibited by raising antibodies against the secreted proteins of the present invention as described above. Without being bound by theory, antibodies used for treatment, bind and prevent the secreted protein from binding to its receptor, thereby inactivating the secreted protein.

In some embodiments, the antibody is conjugated to a therapeutic moiety. In one aspect the therapeutic moiety is a small molecule that modulates the activity of the protein. In another aspect the therapeutic moiety modulates the activity of molecules associated with or in close proximity to the protein. The therapeutic moiety may inhibit enzymatic activity such as protease or protein kinase activity associated with cancer.

The modulators of the present invention can be optionally conjugated to a cytotoxic or therapeutic agent. Examples include chemotherapeutic agents. Such chemotherapeutics can have an established efficacy in treatment of a particular cancer.

Conjugates of a modulator and one or more small molecule toxins, such as a calicheamicin, a maytansine (U.S. Pat. No. 5,208,020), a trichothene, and CC1065 are also contemplated herein. According to some embodiments, the modulating agent is conjugated to one or more maytansine molecules (e.g. about 1 to about 10 maytansine molecules per modulating agent molecule). Maytansine may, for example, be converted to May-SS-Me which may be reduced to May-SH3 and reacted with modified modulating agent (Chari et al. Cancer Research 52: 127-131 (1992)) to generate a maytansinoid-modulating agent conjugate.

Alternatively, the modulating agent is conjugated to one or more calicheamicin molecules. The calicheamicin family of antibiotics is capable of producing double-stranded DNA breaks at sub-picomolar concentrations. Structural analogues of calichearnicin are also known. (Hinman et al. Cancer Research 53: 3336-3342 (1993) and Lode et al. Cancer Research 58: 2925-2928 (1998)).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, dianthin proteins, *Phytolaca americana* proteins (API, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232.

In some embodiments the modulators of the present invention, in particular polypeptides may be derivatized with polyethylene glycol (PEG).

The present invention further contemplates DKKL-1 modulators conjugated with a compound having nucleolytic activity (e.g. a ribonuclease or a DNA endonuclease such as a deoxyribonuclease; DNase). A variety of radioactive isotopes are available for the production of radioconjugated modulating agents. Examples include $Y^{90}$, $At^{211}$, $Re^{186}$, $Re^{188}$, $Sm^{153}$, $Bi^{212}$, $P^{32}$ and radioactive isotopes of Lu. Conjugates of the modulating agent and cytotoxic agent may be made using a variety of bifunctional protein coupling agents such as N-succinimidyl-3-(2-pyridyldithiol) propionate (SPDP), succinimidyl-4-N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis azido compounds (such as bis(p-azidobenzoyl) hexanedianine), bis-diazonium derivatives (such as bis-(pdiazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. Science 238:1098 (1987). Carbon-14-labeled 1-isothiocyanatobenzyl-3-methyldiethylene triaminepentaacetic acid (Mx-DTPA) is an exemplary chelating agent for conjugation of radionucleotide to the modulating agent. (See, for example, WO94/11026). The linker may be a "cleavable linker" facilitating release of the cytotoxic drug in the cell. For example, an acid-labile linker, peptidase-sensitive linker, dimethyl linker or disulfide-containing linker (Chari et al. Cancer Research 52: 127-131 (1992)) may be used. Alternatively, a fusion protein comprising the modulating agent and cytotoxic agent may be made, e.g. by recombinant techniques or peptide synthesis.

In some embodiments, the modulator can be conjugated to a "receptor" (such streptavidin) for utilization in tumor pretargeting wherein the modulating agent-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). The modulating agents of the present invention can also be conjugated with a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of such conjugates may include any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate cleaving enzymes such as β-galactosidase and neuraminidase useful for converting glycosylated prodrugs into free drugs; (3-lactamase useful for converting drugs derivatized with (3-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Modulating agent-abzyme conjugates can be prepared as described herein for delivery of the abzyme to a tumor cell population.

Enzymes can be covalently bound to the DKKL-1 modulator by techniques well known in the art such as the use of the heterobifunctional crosslinking reagents discussed above. Alternatively, fusion proteins comprising at least the antigen binding region of an modulating agent of the invention linked to at least a functionally active portion of an enzyme of the invention can be constructed using recombinant DNA techniques well known in the art [see, e.g., Neuberger et al., Nature, 312: 604-608 (1984)].

In some embodiments, the polypeptides of the present invention are purified or isolated after expression. Proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the protein may be purified using a standard antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the protein. In some instances no purification will be necessary.

Once expressed and purified, if necessary, the proteins and nucleic acids of the present invention are useful in a number of applications. In some aspects, the expression levels of genes are determined for different cellular states in a cancer phenotype; that is, the expression levels of genes in normal tissue and in cancer tissue (and in some cases, for varying severities of lymphoma that relate to prognosis, as outlined below) are evaluated to provide expression profiles. An expression profile of a particular cell state or point of development is essentially a "fingerprint" of the state; while two states may have any particular gene similarly expressed, the evaluation of a number of genes simultaneously allows the generation of a gene expression profile that is unique to the state of the cell. By comparing expression profiles of cells in different states, information regarding which genes are important (including both up- and down-regulation of genes) in each of these states is obtained. Then, diagnosis may be done or confirmed: does tissue from a particular patient have the gene expression profile of normal or cancer tissue.

"Differential expression," or equivalents used herein, refers to both qualitative as well as quantitative differences in the temporal and/or cellular expression patterns of genes, within and among the cells. Thus, a differentially expressed gene can qualitatively have its expression altered, including an activation or inactivation, in, for example, normal versus cancer tissue. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is up-regulated, resulting in an increased amount of transcript, or down-regulated, resulting in a decreased amount of transcript. The degree to which expression differs need only be large enough to quantify via standard characterization techniques as outlined below, such as by use of Affymetrix GeneChip® expression arrays, Lockhart, Nature Biotechnology, 14:1675-1680 (1996), hereby expressly incorporated by reference. Other techniques include, but are not limited to, quantitative reverse transcriptase PCR, Northern analysis and RNase protection. In some embodiments as outlined above, the change in expression (i.e. upregulation or downregulation) is at least about 50%, at least about 100%, at least about 150%, at least about 200%, and from 300 to at least 1000%. In some embodiments the change in expression is upregulation of at least 150% of control.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the protein and standard immunoassays (ELISAs, etc.) or other techniques, including mass spectroscopy assays, 2D gel electrophoresis assays, etc.

In some embodiments, gene expression monitoring is performed and a number of other genes forming an expression profile including DKKL-1 isoforms 2 and 3, are monitored simultaneously. Multiple protein expression monitoring can be done as well. In some embodiments, the nucleic acid probes may be attached to biochips as outlined herein for the detection and quantification of the novel isoforms 2 and 3 of DKKL-1 sequences in a particular cell. The assays are done as is known in the art. In addition, while solid-phase assays are described, any number of solution based assays may be done as well.

Screening for Targeted Drugs

In some embodiments, the sequences described herein are used in drug screening assays. The DKKL-1 proteins, antibodies, nucleic acids, modified proteins of the present invention and cells containing such sequences are used in drug screening assays or by evaluating the effect of drug candidates on a "gene expression profile" or expression profile of polypeptides. In some embodiments, the expression profiles are used, which, in some embodiments are in conjunction with high throughput screening techniques to allow monitoring for expression profile genes after treatment with a candidate agent, Zlokarnik, et al., Science 279, 84-8 (1998), Heid, et al., Genome Res., 6:986-994 (1996).

In some embodiments, the present invention provides methods of identifying a cancer inhibitor. The methods comprise contacting a cell expressing a DKKL-1 splice product with a candidate compound, and determining whether a downstream marker of a DKKL-1 splice product is inhibited. In some embodiments the cancer is characterized by overexpression of a DKKL-1 splice product compared to a control. In some embodiments the DKKL-1 splice product is DKKL-1 isoform 2 or DKKL-1 isoform 3. In some embodiments, inhibition of the downstream marker is indicative of a cancer inhibitor. In some embodiments, the downstream marker is wnt or β-catenin.

The present invention also provides methods for screening for a DKKL-1 splice product modulator comprising contacting a cell expressing a DKKL-1 splice product with a test compound and measuring an activity of a member of a Wnt pathway. In some embodiments, if the activity of the member of the Wnt pathway is modulated compared to a control, then the test compound is a DKKL-1 splice product modulator. In some embodiments, the activity is activation and/or stabilization of β-catenin. In some embodiments the activity is wnt- and/or β-catenin-associated cell signaling.

Candidate bioactive agents are screened for the ability to modulate a gene. "Modulation" thus includes both an increase and a decrease in gene expression or activity. The amount of modulation will depend on the original change of the gene expression in normal versus tumor tissue, with changes of at least 10%, at least 50%, from 100-300%, and from 300-1000% or greater. Thus, for example, if a gene exhibits a 4 fold increase in tumor compared to normal tissue, a decrease of about four fold may be desired; similarly, a 10 fold decrease in expression levels in tumor compared to normal tissue might yield a desired 10 fold increase in expression for a candidate agent.

As will be appreciated by those in the art, this may be done by evaluation at either the gene or the protein level; that is, the amount of gene expression may be monitored using nucleic acid probes and the quantification of gene expression levels, or, alternatively, the level of the gene product itself can be monitored, for example through the use of antibodies to the protein and standard immunoassays. Alternatively, binding and bioactivity assays with the protein may be done as outlined below.

The terms "candidate bioactive agent" or "drug candidate" or grammatical equivalents as used herein describes any molecule, e.g., protein, oligopeptide, small organic or inorganic molecule, polysaccharide, polynucleotide, etc., to be tested for bioactive agents that are capable of directly or indirectly altering either the cancer phenotype, binding to and/or modulating the bioactivity of a protein, or the expression of a sequence, including both nucleic acid sequences and protein sequences. In some embodiments, the candidate agent suppresses a phenotype, for example to a normal tissue fingerprint. Generally a plurality of assay mixtures is run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic or inorganic molecules. In some embodiments the candidate agents are small organic compounds having a molecular weight of more than 100 and less than about 2,500 Daltons. In some embodiments small molecules are less than 2000, or less than 1500 or less than 1000 or less than 500 Daltons. Candidate agents comprise functional groups necessary for structural interaction with proteins, particularly hydrogen bonding, and typically include at least an amine, carbonyl, hydroxyl or carboxyl group. In some embodiments the candidate agents comprise at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. In some embodiments the candidate agents are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, or amidification to produce structural analogs.

In some embodiments, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In some embodiments, the amino acids are in the (S) or L-configuration. If non-naturally occurring side chains are used, non-amino acid substituents may be used, for example to prevent or retard in vivo degradations.

In some embodiments, the candidate bioactive agents are naturally occurring proteins or fragments of naturally occurring proteins. Thus, for example, cellular extracts containing proteins, or random or directed digests of proteinaceous cellular extracts, may be used. In this way libraries of prokaryotic and eukaryotic proteins may be made for screening in the methods of the invention. In some embodiments the libraries are libraries of bacterial, fungal, viral, and mammalian proteins.

In some embodiments, the candidate bioactive agents are peptides of from about 5 to about 30 amino acids, from about 5 to about 20 amino acids, or from about 7 to about 15. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In some embodiments, the library is fully randomized, with no sequence preferences or constants at any position. In some embodiments, the library is biased. That is, some positions within the sequence are either held constant, or are selected from a limited number of possibilities. For example, in some embodiments, the nucleotides or amino acid residues are randomized within a defined class, for example, of hydrophobic amino acids, hydrophilic residues, sterically biased (either small or large) residues, towards the creation of nucleic acid binding domains, the creation of cysteines, for crosslinking, prolines for SH-3 domains, serines, threonines, tyrosines or histidines for phosphorylation sites, etc., or to purines, etc.

In some embodiments, the candidate bioactive agents are nucleic acids. As described generally for proteins, nucleic acid candidate bioactive agents may be naturally occurring nucleic acids, random nucleic acids, or "biased" random nucleic acids. In another embodiment, the candidate bioactive agents are organic chemical moieties, a wide variety of which are available in the literature.

The reactions outlined herein may be accomplished in a variety of ways, as will be appreciated by those in the art. Components of the reaction may be added simultaneously, or sequentially, in any order. In addition, the reaction may include a variety of other reagents in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target. In addition, either solid phase or solution based (i.e., kinetic PCR) assays may be used.

Once the assay is run, the data are analyzed to determine the expression levels, and changes in expression levels as between states, of individual genes, forming a gene expression profile. In some embodiments, as for the diagnosis and prognosis applications, having identified the differentially expressed gene(s) or mutated gene(s) important in any one state, screens can be run to test for alteration of the expression of the novel isoforms of DKKL-1 polynucleotides individually. That is, screening for modulation of regulation of expression of a single gene can be done. Thus, for example, in the case of target genes whose presence or absence is unique between two states, screening is done for modulators of the target gene expression.

In addition, screens can be done for novel genes that are induced in response to a candidate agent. After identifying a candidate agent based upon its ability to suppress a DKKL-1 expression and splicing pattern and creating a normal expression pattern a screen as described above can be performed to identify genes that are specifically modulated in response to the agent. Comparing expression profiles between normal tissue and agent treated tissue reveals genes that are not expressed in normal tissue or diseased tissue, but are expressed in agent treated tissue.

Several cell lines are available for the screening methods of the present invention. In some embodiments, the cell lines are tumor cell lines selected from the group consisting of breast tumor cell lines, liver tumor cell lines, lung tumor cell lines, lymphoid cell lines, ovarian tumor cell lines, cervical tumor cell lines and colon tumor cell lines. In some embodiments, the breast tumor cell line is selected from the group consisting of MDA MB-468, BT-20 and MCF-7. In some embodiments, the lung tumor cell line is selected from the group consisting of NCI-H522, H596, H1229, H520, H2172, H838, and H23. In some embodiments, the lymphoid cell line is K562. In some embodiments, the ovarian tumor cell line is A2780. In some embodiments, the lymphoid cell line is K562. In some embodiments, the cervical tumor cell line is C33A. In some embodiments, the lymphoid cell line is K562. In some embodiments, the colon tumor cell line is selected from the group consisting of HCT-8 and Colo320DM.

Applications of the Invention

In some embodiments, the invention provides methods for assessing the oncogenic potential of the novel splice variants of the DKKL-1 gene in different tissues. The assessment can be performed in multiple different biological assays including without limitation transformation assays, colony formation assays, and nude mice studies.

Proteins encoded by the splice variants are purified from recombinant systems and used as immunogen for the generation of monoclonal antibody for therapeutic purposes.

The DKK family members are known to be secreted growth factors which act as either agonist or antagonist of the wnt signaling pathway. The invention provides physiological receptors of DKKL-1. The invention further provides methods for regulating the effects of the different DKKL-1 splice variants in either wnt signaling or novel receptor signaling.

Signaling pathways induced by differential expression of the DKKL-1 isoforms and the oncogenic phenotype associated with these signaling events are also provided. In some embodiments the signaling pathways include the wnt pathway and the β-catenin pathway. Methods for use of such pathways for screening therapeutic entities that may influence the signaling potential of the DKKL-1 oncogenes are provided.

Human cancer indication on DKKL-1 by expression profiling on primary tumors is provided. Other potential oncogenic mechanisms, like DNA amplification of the loci and dys-regulation of the splicing events of the DKKL-1 locus on different primary tumors are also provided as methods for detection of cancer states.

The present invention provides methods of modulating a DKKL-1 splice product-related biological activity in a patient. In some embodiments the methods comprise administering to the patient an amount of a DKKL-1 splice product modulator effective to modulate a DKKL-1 splice product-related biological activity. In some embodiments the patient has or is predisposed to one or more of ovarian cancer, lung cancer, liver cancer, cervical cancer, colon cancer, breast cancer or lymphoma.

In some embodiments the DKKL-1 splice product-related biological activity is cancer cell proliferation, cancer cell growth, tumorigenicity, cancer cell migration, cancer cell metastasis, or cancer cell survival. In some embodiments the DKKL-1 splice product-related biological activity is β-catenin signaling and Wnt signaling. In some embodiments the DKKL-1 splice product-related biological activity is β-catenin stabilization and/or activation. In some embodiments the DKKL-1 splice product modulator is an antibody and is administered to the subject via in vivo therapeutic antibody gene transfer.

As used herein, the phrase "inhibits cancer cell growth" refers to inhibition or abolition of cancer cell growth in the presence of a DKKL-1 splice product modulator wherein the cell differentially expresses a DKKL-1 splice product. In this context, cancer cell growth can be decreased by at least 10%, at least 25%, at least 50%, at least 75%, at least 85%, at least 90%, at least 95%, up to 100% relative to cancer cell growth in the absence of a DKKL-1 splice product modulator. Comparisons of cancer cell growth can be accomplished using, for example, MTT assay (for example, the Vybrant® MTT Cell Proliferation Assay Kit (Invitrogen)); BrdU incorporation (for example, the Absolute-S SBIP assay (Invitrogen)); measuring intracellular ATP levels (for example using ATPLite™-M, 1,000 Assay Kit (PerkinElmer) or ATP Cell Viability Assay Kit (BioVision)); DiOc18 assay, a membrane permeable dye (Invitrogen); Glucose-6-phosphate dehydrogenase activity assay (for example, the Vibrant cytotoxicity assay (Invitrogen)); or measuring cellular LDH activity.

As used herein, the phrases "inhibits tumor formation" and "inhibits tumorigenicity" refers to inhibition or abolition of tumor formation in the presence of a DKKL-1 splice product modulator wherein the tumor comprises cells that differentially express a DKKL-1 splice product. In this context, tumor formation can be decreased by at least 10%, at least 25%, at least 50%, at least 75%, at least 85%, at least 90%, at least 95%, and up to 100% relative to tumor formation in the absence of a DKKL-1 splice product modulator. Comparisons of tumor formation can be accomplished using, for example, cell based assays (for example colony formation in soft agar); in vivo models of tumor formation typically relying upon injecting the cells of interest into animals (for example, athymic mice or rats, irradiated mice or rats; inoculation into immunologically privileged sites such as brain, cheek pouch or eye; inoculation of syngeneic animals) and monitoring the size of the mass after a defined time period.

As used herein, the phrase "inhibits signaling" refers to decreasing the effect of one or more DKKL-1 splice products on downstream members of cellular signaling cascades that include DKKL-1. Cellular signaling cascades that include DKKL-1 include the wnt pathway, among others. Inhibition of signaling can be determined by measuring polypeptide or polynucleotide levels of downstream members of the cellular signaling pathway.

The present invention also provides methods of inhibiting a cancer cell phenotype in a population of cells expressing a DKKL-1 splice product. In some embodiments the methods comprise administering to the cancer cell population a DKKL-1 splice product modulator. In some embodiments the amount of DKKL-1 splice product modulator administered to the cancer cells is effective to inhibit a cancer cell phenotype. In some embodiments the cancer cell phenotype is cancer cell proliferation, cancer cell growth, cancer cell metastasis, tumor formation, cancer cell migration, or cancer cell survival.

In some embodiments the cancer cells are ovarian cancer cells, lung cancer cells, liver cancer cells, cervical cancer cells, colon cancer cells, breast cancer cells or lymphoid cells.

The present invention also provides methods for modulating a DKKL-1 splice product pathway or Wnt pathway. The methods comprise contacting a cell expressing a DKKL-1 splice product with a test compound and measuring a downstream marker of the DKKL-1 splice product pathway and/or Wnt pathway. In some embodiments, if the activity of the downstream marker of the DKKL-1 splice product pathway and/or Wnt pathway is modulated compared to a control, then the test compound is a DKKL-1 splice product modulator.

The present invention further provides methods of inhibiting cancer cell proliferation, tumor growth, metastasis, cancer cell survival tumorigenicity and cell migration are provided. The methods comprise administering to a population of cells an amount of a DKKL-1 splice product modulator effective to inhibit the desired activity and/or phenotype. In some embodiments the administration of the DKKL-1 splice product modulator inhibits the activity and/or phenotype at least about 25%, at least about 30%, at least about 40%, at least about 50%, at least about 75%, at least about 80%, at least about 90%, at least about 95%, at least about 99% as compared to a control.

In some embodiments the methods comprise administering a DKKL-1 splice product modulator. In some embodiments, the modulator is an antisense molecule, a pharmaceutical composition, a therapeutic agent or small molecule, or a monoclonal, polyclonal, chimeric or humanized antibody. In particular embodiments, a therapeutic agent is coupled with an antibody which, in some embodiments, is a monoclonal antibody.

Methods for Delivering a Cytotoxic Agent or a Diagnostic Agent to a Cell

The present invention also provides methods for delivering a cytotoxic agent or a diagnostic agent to one or more cells that a DKKL-1 splice product. In some embodiments the methods comprise contacting a DKKL-1 splice product modulator of the present invention conjugated to a cytotoxic agent or diagnostic agent with the cell. In some embodiments the DKKL-1 splice product modulator is a monoclonal antibody which specifically binds to DKKL-1 isoform 2 and/or DKKL-1 isoform 3. In some embodiments the cytotoxic agent is a chemotherapeutic agent.

Methods for Diagnosing Cancer and/or Detecting Cancer Cells

In some embodiments, methods for detection or diagnosis of cancer cells in an individual are provided. In some embodiments, the diagnostic/detection agent is a small molecule that preferentially binds to a DKKL-1 isoform according to the invention. In some embodiments, the diagnostic/detection agent is an antibody, in some embodiments, a monoclonal antibody. In some embodiments the antibody is linked to a detectable agent.

The present invention provides methods for detecting one or more cancer cells in a sample. In some embodiments the cancer cells differentially express one or more DKKL-1 splice products. In some embodiments the methods comprise contacting the sample with a composition comprising a DKKL-1 splice product modulator linked to an imaging agent and detecting the localization of the imaging agent in the sample. In some embodiments the DKKL-1 splice product modulator is a monoclonal antibody. In some embodiments the imaging agent is $^{18}$F, $^{43}$K, $^{52}$Fe, $^{57}$Co, $^{67}$Cu, $^{67}$Ga, $^{77}$Br, $^{87}$MSr, $^{86}$Y, $^{90}$Y, $^{99}$MTc, $^{111}$In, $^{123}$I, $^{125}$I, $^{127}$Cs, $^{129}$Cs, $^{131}$I, $^{132}$I, $^{197}$Hg, $^{203}$Pb, or $^{206}$Bi.

The present invention also provides methods for determining the susceptibility of a patient to treatment with a DKKL-1 splice product modulator. In some embodiments the methods comprise detecting evidence of differential expression of a DKKL-1 splice product in a patient's cancer sample. In some embodiments evidence of differential expression of a DKKL-1 splice product in the sample indicates that the patient is susceptible to treatment with a DKKL-1 splice product modulator. In some embodiments the differential expression of the DKKL-1 splice product is upregulation of the DKKL-1 splice product.

The present invention also provides methods for determining the prognosis of a cancer patient. The methods comprise determining the ratio of wild-type DKKL-1 expression products to DKKL-1 splice product expression products in a patient's sample. In some embodiments the ratio of wild-type DKKL-1 expression products to DKKL-1 splice product expression products is used to determine the prognosis of the cancer patient. In some embodiments, a ratio of at least 2:1, at least 3:1, at least 4:1, at least 5:1, and at least 10:1 of wild-type DKKL-1 expression products:DKKL-1 splice product expression products indicates that the patient has a good prognosis with respect to survival and successful treatment with a composition of the present invention and/or a conventional cancer medicament. In some embodiments the wild-type DKKL-1 is encoded for by a nucleic acid having a sequence having at least 95% identity to a sequence of SEQ ID NO:1. In some embodiments wild-type DKKL-1 is encoded for by a nucleic acid having a sequence of SEQ ID NO:1. In some embodiments the wild-type DKKL-1 has a polypeptide sequence having at least 95% identity to a sequence of SEQ ID NO:2. In some embodiments the wild-type DKKL-1 has a polypeptide sequence of SEQ ID NO:2. In some embodiments the DKKL-1 splice product is DKKL-1 isoform 2 or DKKL-1 isoform 3.

In some embodiments, animal models and transgenic animals are provided, which find use in generating animal models of cancers including, without limitation, ovarian cancer, lung cancer, liver cancer, cervical cancer, colon cancer, breast cancer and lymphoma.

(a) Antisense Molecules

In some embodiments, the cancer inhibitor is an antisense molecule. Antisense molecules as used herein include antisense or sense oligonucleotides comprising a single-stranded nucleic acid sequence (either RNA or DNA) capable of binding to target mRNA (sense) or DNA (antisense) sequences for cancer molecules. Antisense or sense oligonucleotides, according to the present invention, comprise a fragment generally at least about 14 nucleotides, or from about 14 to 30 nucleotides. The ability to derive an antisense or a sense oligonucleotide, based upon a cDNA sequence encoding a given protein is described in, for example, Stein and Cohen, Cancer Res. 48:2659, (1988) and van der Krol et al., BioTechniques 6:958, (1988).

Antisense molecules can be modified or unmodified RNA, DNA, or mixed polymer oligonucleotides. These molecules function by specifically binding to matching sequences resulting in inhibition of peptide synthesis (Wu-Pong, November 1994, BioPharm, 20-33) either by steric blocking or by activating an RNase H enzyme. Antisense molecules can also alter protein synthesis by interfering with RNA processing or transport from the nucleus into the cytoplasm (Mukhopadhyay & Roth, 1996, Crit. Rev. in Oncogenesis 7, 151-190). In addition, binding of single stranded DNA to RNA can result in nuclease-mediated degradation of the heteroduplex (Wu-Pong, supra). Backbone modified DNA chemistry which have thus far been shown to act as substrates for RNase H are phosphorothioates, phosphorodithioates, borontrifluoridates, and 2'-arabino and 2'-fluoro arabino-containing oligonucleotides.

Antisense molecules may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. In some embodiments, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a sense or an antisense oligonucleotide may be introduced into a cell containing the target nucleic acid sequence by formation of an oligonucleotide-lipid complex, as described in WO 90/10448. It is understood that the use of antisense molecules or knock out and knock in models may also be used in screening assays as discussed above, in addition to methods of treatment.

In some embodiments the DKKL-1 splice product modulator is an antisense oligonucleotide which is at least 50%, at least 60%, at least 70%, at least 80%, at least 90%, at least 95%, at least 96%, at least 97%, at least 98%, at least 99%, or 100% homologous to a region, portion, domain, or segment of DKKL-1, or the complement thereof. In some embodiments there is substantial sequence homology over at least 15, 20, 25, 30, 35, 40, or 50 consecutive nucleotides of the gene.

(b) RNA Interference

RNA interference refers to the process of sequence-specific post transcriptional gene silencing in animals mediated by short interfering RNAs (siRNA) (Fire et al., Nature, 391, 806 (1998)). The corresponding process in plants is referred to as post transcriptional gene silencing or RNA silencing and is also referred to as quelling in fungi. The presence of dsRNA in cells triggers the RNAi response though a mechanism that has yet to be fully characterized. This mechanism appears to be different from the interferon response that results from dsRNA mediated activation of protein kinase PKR and 2',5'-oligoadenylate synthetase resulting in non-specific cleavage of mRNA by ribonuclease L. (reviewed in Sharp, P. A., RNA interference—2001, Genes & Development 15:485-490 (2001)).

Small interfering RNAs (siRNAs) are powerful sequence-specific reagents designed to suppress the expression of genes in cultured mammalian cells through a process known as RNA interference (RNAi). Elbashir, S. M. et al. Nature 411: 494-498 (2001); Caplen, N. J. et al. Proc. Natl. Acad. Sci. USA 98:9742-9747 (2001); Harborth, J. et al. J. Cell Sci. 114:4557-4565 (2001). The term "short interfering RNA" or "siRNA" refers to a double stranded nucleic acid molecule capable of RNA interference "RNAi", (see Kreutzer et al., WO 00/44895; Zernicka-Goetz et al. WO 01/36646; Fire, WO 99/32619; Mello and Fire, WO 01/29058). As used herein, siRNA molecules are limited to RNA molecules but further encompasses chemically modified nucleotides and non-nucleotides. siRNA gene-targeting experiments have been carried out by transient siRNA transfer into cells (achieved by such classic methods as liposome-mediated transfection, electroporation, or microinjection).

In some embodiments, eolecules of siRNA are 21- to 23-nucleotide RNAs. In some embodiments, eolecules of siRNA are 18- to 25-nucleotide RNAs. In some embodiments the siRNAs have 2- to 3-nucleotide 3'-overhanging ends resembling the RNase III processing products of long double-stranded RNAs (dsRNAs) that normally initiate RNAi. When introduced into a cell, they assemble with yet-to-be-identified proteins of an endonuclease complex (RNA-induced silencing complex), which then guides target mRNA cleavage. As a consequence of degradation of the targeted mRNA, cells with a specific phenotype characteristic of suppression of the corresponding protein product are obtained. The small size of siRNAs, compared with traditional antisense molecules, prevents activation of the dsRNA-inducible interferon system present in mammalian cells. This avoids the nonspecific phenotypes normally produced by dsRNA larger than 30 base pairs in somatic cells.

Intracellular transcription of small RNA molecules is achieved by cloning the siRNA templates into RNA polymerase III (Pol III) transcription units, which normally encode the small nuclear RNA (snRNA) U6 or the human RNase P RNA H1. Two approaches have been developed for expressing siRNAs: in the first, sense and antisense strands constituting the siRNA duplex are transcribed by individual promoters (Lee, N. S. et al. Nat. Biotechnol. 20, 500-505 (2002). Miyagishi, M. & Taira, K. Nat. Biotechnol. 20, 497-500 (2002).); in the second, siRNAs are expressed as fold-back stem-loop structures that give rise to siRNAs after intracellular processing (Paul, C. P. et al. Nat. Biotechnol. 20:505-508 (2002)). The endogenous expression of siRNAs from introduced DNA templates is thought to overcome some limitations of exogenous siRNA delivery, in particular the transient loss of phenotype. U6 and H1 RNA promoters are members of the type III class of Pol III promoters. (Paule, M. R. & White, R. J. Nucleic Acids Res. 28, 1283-1298 (2000)).

Coexpression of sense and antisense siRNAs mediate silencing of target genes, whereas expression of sense or antisense siRNA alone do not greatly affect target gene expression. Transfection of plasmid DNA, rather than synthetic siRNAs, may appear advantageous, considering the danger of RNase contamination and the costs of chemically synthesized siRNAs or siRNA transcription kits. Stable expression of siRNAs allows new gene therapy applications, such as treatment of persistent viral infections. Considering the high specificity of siRNAs, the approach also allows the targeting of disease-derived transcripts with point mutations, such as RAS or TP53 oncogene transcripts, without alteration of the remaining wild-type allele. Finally, by high-throughput sequence analysis of the various genomes, the DNA-based methodology may also be a cost-effective alternative for automated genome-wide loss-of-function phenotypic analysis, especially when combined with miniaturized array-based phenotypic screens. (Ziauddin, J. & Sabatini, D. M. Nature 411:107-110 (2001)).

The presence of long dsRNAs in cells stimulates the activity of a ribonuclease III enzyme referred to as dicer. Dicer is involved in the processing of the dsRNA into short pieces of dsRNA known as short interfering RNAs (siRNA) (Berstein et al., 2001, Nature, 409:363 (2001)). Short interfering RNAs derived from dicer activity are typically about 21-23 nucleotides in length and comprise about 19 base pair duplexes. Dicer has also been implicated in the excision of 21 and 22 nucleotide small temporal RNAs (stRNA) from precursor RNA of conserved structure that are implicated in translational control (Hutvagner et al., Science, 293, 834 (2001)). The RNAi response also features an endonuclease complex containing a siRNA, commonly referred to as an RNA-induced silencing complex (RISC), which mediates cleavage of single stranded RNA having sequence homologous to the siRNA. Cleavage of the target RNA takes place in the middle of the region complementary to the guide sequence of the siRNA duplex (Elbashir et al., Genes Dev., 15, 188 (2001)).

This invention provides expression systems comprising an isolated nucleic acid molecule comprising a sequence capable of specifically hybridizing to the polynucleotide sequences of the novel DKKL-1 isoforms. In some embodiments, the nucleic acid molecule is capable of inhibiting the expression of the corresponding protein. Methods of inhibiting expression of the novel DKKL-1 isoforms inside a cell by a vector-directed expression of a short RNA which short RNA can fold in itself and create a double strand RNA having the novel DKKL-1 isoforms mRNA sequence identity and able to trigger posttranscriptional gene silencing, or RNA interference (RNAi), of the novel isoforms of the DKKL-1 gene inside the cell. In some embodiments a short double strand RNA having the novel DKKL-1 isoform mRNA sequence identity is delivered inside the cell to trigger posttranscriptional gene silencing, or RNAi, of the novel DKKL-1 isoforms. In some embodiments, the nucleic acid molecule is at least a 7 mer, at least a 10 mer, or at least a 20 mer. In some embodiments, the sequence is unique.

In some embodiments the DKKL-1 splice product modulator is a double stranded RNA (dsRNA) molecule and works via RNAi (RNA interference). In some embodiments, one strand of the dsRNA is at least 50%, at least 60%, at least 70%, at least 80%, at least 90%, at least 95%, at least 96%, at least 97%, at least 98%, at least 99%, or 100% homologous to a region, portion, domain, or segment of DKKL-1. In some embodiments there is substantial sequence homology over at least 15, 20, 25, 30, 35, 40, 50, 100, 200, 300, 400, 500, or 1000 consecutive nucleotides of the gene. In some embodiments there is substantial sequence homology over the entire length of the gene.

In some embodiments the DKKL-1 splice product modulator is a siRNA. In some embodiments, the siRNA is at least 50%, at least 60%, at least 70%, at least 80%, at least 90%, at least 95%, at least 96%, at least 97%, at least 98%, at least 99%, or 100% homologous to a region, portion, domain, or segment of DKKL-1 or the complement thereof. In some embodiments there is substantial sequence homology over at least 15, 20, 25, 30, 35, 40, or 50 consecutive nucleotides of the gene. In some embodiments, the siRNA oligonucleotides have a sequence selected from the group consisting of AAA-GAGGAGAACCAGGAGCAC (Si379-2; SEQ ID NO:13); GGTGGCCTTCTGGATCATTAA (Si379-8; SEQ ID NO:14); and GACCCACAAGGACGTCCTAGA (Si379-10; SEQ ID NO:15)

(c) Pharmaceutical Compositions

The present invention provides compositions comprising a DKKL-1 splice product modulator and one or more pharmaceutically acceptable carriers. In some embodiments the DKKL-1 splice product modulator is an isolated double-stranded RNA (dsRNA) of SEQ ID NO:3 or SEQ ID NO:5.

In some embodiments the DKKL-1 splice product modulator is an isolated oligonucleotide comprising at least 10 consecutive nucleotides of a sequence of SEQ ID NO:3 or SEQ ID NO:5. In some embodiments the DKKL-1 splice product modulator is an isolated oligonucleotide comprising at least 20 consecutive nucleotides of a sequence of SEQ ID NO:3 or SEQ ID NO:5.

In some embodiments the DKKL-1 splice product modulator is an antibody that specifically binds an epitope of a DKKL-1 splice product. In some embodiments the DKKL-1 splice product is DKKL-1 isoform 2 or DKKL-1 isoform 3. In some embodiments the antibody is a monoclonal antibody. In some embodiments, DKKL-1 isoform 2 has a polypeptide sequence having at least 95% identical to a sequence of SEQ ID NO:4. In some embodiments, DKKL-1 isoform 2 has a polypeptide sequence of SEQ ID NO:4. In some embodiments, DKKL-1 isoform 3 has a polypeptide sequence having at least 95% identical to a sequence of SEQ ID NO:6. In some embodiments, DKKL-1 isoform 3 has a polypeptide sequence of SEQ ID NO:6. In some embodiments the antibody binds to DKKL-1 isoform 2 but does not specifically bind to DKKL-1 isoform 1 or DKKL-1 isoform 3. In some embodiments the antibody binds to DKKL-1 isoform 3 but does not specifically bind to DKKL-1 isoform I or DKKL-1 isoform 2. In some embodiments the antibody specifically binds to DKKL-1 isoform 2 and DKKL-1 isoform 3 but does not specifically bind to DKKL-1 isoform 1.

Pharmaceutical compositions encompassed by the present invention include as active agent, the polypeptides, polynucleotides, antisense oligonucleotides, or antibodies of the invention disclosed herein in a therapeutically effective amount. An "effective amount" is an amount sufficient to effect beneficial or desired results, including clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

The compositions of the present invention can be used to treat cancer as well as metastases of primary cancer. In addition, the pharmaceutical compositions can be used in conjunction with conventional methods of cancer treatment, e.g., to sensitize tumors to radiation or conventional chemotherapy. The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

Where the pharmaceutical composition comprises an antibody that specifically binds to a gene product encoded by a differentially expressed polynucleotide, the antibody can be coupled to a drug for delivery to a treatment site or coupled to a detectable label to facilitate imaging of a site comprising cancer cells, such as prostate cancer cells. Methods for coupling antibodies to drugs and detectable labels are well known in the art, as are methods for imaging using detectable labels.

A "patient" for the purposes of the present invention includes both humans and other animals, particularly mammals, and organisms. Thus the methods are applicable to both human therapy and veterinary applications. In some embodiments the patient is a mammal, and, in some embodiments, the patient is human.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. The effective amount for a given situation is determined by routine experimentation and is within the judgment of the clinician. For purposes of the present invention, an effective dose will generally be from about 0.01 mg/kg to about 5 mg/kg, or about 0.01 mg/kg to about 50 mg/kg or about 0.05 mg/kg to about 10 mg/kg of the compositions of the present invention in the individual to which it is administered.

A pharmaceutical composition can also comprise one or more pharmaceutically acceptable carriers. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Typically, the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington: The Science and Practice of Pharmacy (1995) Alfonso Gennaro, Lippincott, Williams, & Wilkins.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

In some embodiments the pharmaceutical compositions of the present invention are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. In some embodiments the salts are ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1-100% wt/vol. Once formulated, the compositions contemplated by the invention can be (1) administered directly to the subject (e.g., as polynucleotide, polypeptides, small molecule agonists or antagonists, and the like); or (2) delivered ex vivo, to cells derived from the subject (e.g., as in ex vivo gene therapy). Direct delivery of the compositions will generally be accomplished by parenteral injection, e.g., subcutaneously, intraperitoneally, intravenously or intramuscularly, intratumoral or to the interstitial space of a tissue. Other modes of administration include oral and pulmonary administration, suppositories, and transdermal applications, needles, and gene guns or hyposprays. Dosage treatment can be a single dose schedule or a multiple dose schedule.

Methods for the ex vivo delivery and reimplantation of transformed cells into a subject are known in the art and described in e.g., International Publication No. WO 93/14778. Examples of cells useful in ex vivo applications include, for example, stem cells, particularly hematopoetic, lymph cells, macrophages, dendritic cells, or tumor cells. Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

The dose and the means of administration of the inventive pharmaceutical compositions are determined based on the specific qualities of the therapeutic composition, the condition, age, and weight of the patient, the progression of the disease, and other relevant factors. For example, administration of polynucleotide therapeutic compositions agents includes local or systemic administration, including injection, oral administration, particle gun or catheterized administration, and topical administration. In some embodiments, the therapeutic polynucleotide composition contains an expression construct comprising a promoter operably linked to a polynucleotide of at least 12, 22, 25, 30, or 35 contiguous nt of the polynucleotide disclosed herein. Various methods can be used to administer the therapeutic composition directly to a specific site in the body. For example, a small metastatic lesion is located and the therapeutic composition injected several times in several different locations within the body of tumor. Alternatively, arteries that serve a tumor are identified, and the therapeutic composition injected into such an artery, in order to deliver the composition directly into the tumor. A tumor that has a necrotic center is aspirated and the composition injected directly into the now empty center of the tumor. An antisense composition is directly administered to the surface of the tumor, for example, by topical application of the composition. X-ray imaging is used to assist in certain of the above delivery methods.

Targeted delivery of therapeutic compositions containing an antisense polynucleotide, subgenomic polynucleotides, or antibodies to specific tissues can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. (USA) (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. Factors such as method of action (e.g., for enhancing or inhibiting levels of the encoded gene product) and efficacy of transformation and expression are considerations that will affect the dosage required for ultimate efficacy of the antisense subgenomic polynucleotides. Where greater expression is desired over a larger area of tissue, larger amounts of antisense subgenomic polynucleotides or the same amounts re-administered in a successive protocol of administrations, or several administrations to different adjacent or close tissue portions of, for example, a tumor site, may be required to affect a positive therapeutic outcome. In all cases, routine experimentation in clinical trials will determine specific ranges for optimal therapeutic effect.

The therapeutic polynucleotides and polypeptides of the present invention can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP 0 345 242; and WO 91/02805), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:16985); eukaryotic cell delivery vehicles cells (see, e.g., U.S. Pat. No. 5,814,482; WO 95/07994; WO 96/17072; WO 95/30763; and WO 97/42338) and nucleic charge neutralization or fusion with cell membranes. Naked DNA can also be employed. Exemplary naked DNA introduction methods are described in WO 90/11092 and U.S. Pat. No. 5,580,859. Liposomes that can act as gene delivery vehicles are described in U.S. Pat. No. 5,422,120; WO 95/13796; WO 94/23697; WO 91/14445; and EP 0524968. Additional approaches are described in Philip, Mol. Cell. Biol. (1994) 14:2411, and in Woffendin, Proc. Natl. Acad. Sci. (1994) 91:1581.

Further non-viral delivery suitable for use includes mechanical delivery systems such as the approach described in Woffendin et al., Proc. Natl. Acad. Sci. USA (1994) 91(24): 11581. Moreover, the coding sequence and the product of expression of such can be delivered through deposition of photopolymerized hydrogel materials or use of ionizing radiation (see, e.g., U.S. Pat. No. 5,206,152 and WO 92/11033). Other conventional methods for gene delivery that can be used for delivery of the coding sequence include, for example, use of hand-held gene transfer particle gun (see, e.g., U.S. Pat. No. 5,149,655); use of ionizing radiation for activating transferred gene (see, e.g., U.S. Pat. No. 5,206,152 and WO 92/11033).

(d) Antibodies

In some embodiments, a cancer inhibitor is an antibody as discussed above. In some embodiments, the DKKL-1 isoform proteins of the present invention may be used to generate polyclonal and monoclonal antibodies to the proteins, which are useful as described herein. Similarly, the proteins can be coupled, using standard technology, to affinity chromatography columns. These columns may then be used to purify antibodies against polypeptides of the novel DKKL-1 isoforms. In some embodiments, the antibodies are generated to epitopes unique to a protein; that is, the antibodies show little or no cross-reactivity to other proteins. These antibodies find use in a number of applications. For example, the antibodies may be coupled to standard affinity chromatography columns and used to purify the novel DKKL-1 isoform proteins. The antibodies may also be used therapeutically as blocking polypeptides, as outlined above, since they will specifically bind to the protein.

Detection of specific binding of the antibody specific for the encoded cancer-associated polypeptide, when compared to a suitable control is an indication that encoded polypeptide is present in the sample. Suitable controls include a sample known not to contain the encoded the novel DKKL-1 isoform polypeptides or known not to contain elevated levels of the polypeptide; such as normal tissue, and a sample contacted with an antibody not specific for the encoded polypeptide, e.g., an anti-idiotype antibody. A variety of methods to detect specific antibody-antigen interactions are known in the art and can be used in the method, including, but not limited to, standard immunohistological methods, immunoprecipitation, an enzyme immunoassay, and a radioimmunoassay. In general, the specific antibody will be detectably labeled, either directly or indirectly. Direct labels include radioisotopes; enzymes whose products are detectable (e.g., luciferase, β-galactosidase, and the like); fluorescent labels (e.g., fluorescein isothiocyanate, rhodamine, phycoerythrin, and the like); fluorescence emitting metals, e.g., 152Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. The antibody may be attached (coupled) to an insoluble support, such as a polystyrene plate or a bead. Indirect labels include second antibodies specific for antibodies specific for the encoded polypeptide ("first specific antibody"), wherein the second antibody is labeled as described above; and members of specific binding pairs, e.g., biotin-avidin, and the like. The biological sample may be brought into contact with and immobilized on a solid support or carrier, such as nitrocellulose, that is capable of immobilizing cells, cell particles, or soluble proteins. The support may then be washed with suitable buffers, followed by contacting with a detectably-labeled first specific antibody. Detection methods are known in the art and will be chosen as appropriate to the signal emitted by the detectable label. Detection is generally accomplished in comparison to suitable controls, and to appropriate standards.

(e) Detection and Diagnosis of Cancers

In some embodiments, the present invention provides methods to locate or identify sites where cancer cells are present. In some embodiments, a detectably-labeled moiety, e.g., an antibody, which is specific for a cancer-associated polypeptide is administered to an individual (e.g., by injection), and labeled cells are located using standard imaging techniques, including, but not limited to, magnetic resonance imaging, computed tomography scanning, and the like. In this manner, cancer cells are differentially labeled.

The present invention provides methods for identifying cancer cells containing the novel DKKL-1 polynucleotides. In some embodiments, the novel DKKL-1 isoform sequences are used as probes to determine the number of copies of the DKKL-1 gene in the genome. For example, some cancers exhibit chromosomal deletions or insertions, resulting in an alteration in the copy number of a gene.

The present invention provides methods of using the polynucleotides described herein for detecting cancer cells, facilitating diagnosis of cancer and the severity of a cancer (e.g., tumor grade, tumor burden, and the like) in a subject, facilitating a determination of the prognosis of a subject, and assessing the responsiveness of the subject to therapy (e.g., by providing a measure of therapeutic effect through, for example, assessing tumor burden during or following a chemotherapeutic regimen). Detection can be based on detection of a polynucleotide that is differentially expressed in a cancer cell, and/or detection of a polypeptide encoded by a polynucleotide that is differentially expressed in a cancer cell. The detection methods of the invention can be conducted in vitro or in vivo, on isolated cells, or in whole tissues or a bodily fluid e.g., blood, plasma, serum, urine, and the like).

In some embodiments, methods are provided for detecting a cancer cell by detecting expression in the cell of a transcript that is differentially expressed in a cancer cell. Any of a variety of known methods can be used for detection, including, but not limited to, detection of a transcript by hybridization with a polynucleotide that hybridizes to a polynucleotide that is differentially expressed in a prostate cancer cell; detection of a transcript by a polymerase chain reaction using specific oligonucleotide primers; in situ hybridization of a cell using as a probe a polynucleotide that hybridizes to a gene that is differentially expressed in a prostate cancer cell. The methods can be used to detect and/or measure mRNA levels of a gene that is differentially expressed in a cancer cell. In some embodiments, the methods comprise: a) contacting a sample with a polynucleotide that corresponds to a differentially expressed gene described herein under conditions that allow hybridization; and b) detecting hybridization, if any.

Detection of differential hybridization, when compared to a suitable control, is an indication of the presence in the sample of a polynucleotide that is differentially expressed in a cancer cell. Appropriate controls include, for example, a sample that is known not to contain a polynucleotide that is differentially expressed in a cancer cell, and use of a labeled polynucleotide of the same "sense" as the polynucleotide that is differentially expressed in the cancer cell. Conditions that allow hybridization are known in the art, and have been described in more detail above. Detection can also be accomplished by any known method, including, but not limited to, in situ hybridization, PCR (polymerase chain reaction), RT-PCR (reverse transcription-PCR), TMA, bDNA, and Nasbau and "Northern" or RNA blotting, or combinations of such techniques, using a suitably labeled polynucleotide. A variety of labels and labeling methods for polynucleotides are known in the art and can be used in the assay methods of the invention. Specificity of hybridization can be determined by comparison to appropriate controls.

Polynucleotides generally comprising at least 10 nt, at least 12 nt or at least 15 contiguous nucleotides of a polynucleotide provided herein are used for a variety of purposes, such as probes for detection of and/or measurement of, transcription levels of a polynucleotide that is differentially expressed in a prostate cancer cell. As will be readily appreciated by the ordinarily skilled artisan, the probe can be detectably labeled and contacted with, for example, an array comprising immobilized polynucleotides obtained from a test sample (e.g., mRNA). Alternatively, the probe can be immobilized on an array and the test sample detectably labeled. These and other variations of the methods of the invention are well within the skill in the art and are within the scope of the invention.

Nucleotide probes can also be used to detect expression of a gene corresponding to the provided polynucleotide. In Northern blots, mRNA is separated electrophoretically and contacted with a probe. A probe is detected as hybridizing to an mRNA species of a particular size. The amount of hybridization can be quantitated to determine relative amounts of expression, for example under a particular condition. Probes are used for in situ hybridization to cells to detect expression. Probes can also be used in vivo for diagnostic detection of hybridizing sequences. Probes are typically labeled with a radioactive isotope. Other types of detectable labels can be used such as chromophores, fluorophores, and enzymes. Other examples of nucleotide hybridization assays are described in WO92/02526 and U.S. Pat. No. 5,124,246.

PCR is another means for detecting small amounts of target nucleic acids (see, e.g., Mullis et al., Meth. Enzymol. (1987) 155:335; U.S. Pat. No. 4,683,195; and U.S. Pat. No. 4,683,202). Two primer oligonucleotides that hybridize with the target nucleic acids are used to prime the reaction. The primers can be composed of sequence within or 3' and 5' to the polynucleotides disclosed herein. Alternatively, if the primers are 3' and 5' to these polynucleotides, they need not hybridize to them or the complements. After amplification of the target with a thermostable polymerase, the amplified target nucleic acids can be detected by methods known in the art, e.g., Southern blot. mRNA or cDNA can also be detected by traditional blotting techniques (e.g., Southern blot, Northern blot, etc.) described in Sambrook et al., "Molecular Cloning: A Laboratory Manual" (New York, Cold Spring Harbor Laboratory, 1989) (e.g., without PCR amplification). In general, mRNA or cDNA generated from mRNA using a polymerase enzyme can be purified and separated using gel electrophoresis, and transferred to a solid support, such as nitrocellulose. The solid support is exposed to a labeled probe, washed to remove any unhybridized probe, and duplexes containing the labeled probe are detected.

Methods using PCR amplification can be performed on the DNA from a single cell, although it is convenient to use at least about 105 cells. The use of the polymerase chain reaction is described in Saiki et al. (1985) Science 239:487, and a review of current techniques may be found in Sambrook, et al. Molecular Cloning: A Laboratory Manual, CSH Press 1989, pp. 14.2-14.33. A detectable label may be included in the amplification reaction. Suitable detectable labels include fluorochromes, (e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA)), radioactive labels, (e.g. 32P, 35S, 3H, etc.), and the like. The label may be a two stage system, where the polynucleotides is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The detection methods can be provided as part of a kit. Thus, the invention further provides kits for detecting the presence and/or a level of a polynucleotide that is differentially expressed in a cancer cell (e.g., by detection of an mRNA encoded by the differentially expressed gene of interest), and/or a polypeptide encoded thereby, in a biological sample. Procedures using these kits can be performed by clinical laboratories, experimental laboratories, medical practitioners, or private individuals. The kits of the invention for detecting a polypeptide encoded by a polynucleotide that is differentially expressed in a cancer cell may comprise a moiety that specifically binds the polypeptide, which may be an antibody that binds the polypeptide or fragment thereof. The kits of the invention used for detecting a polynucleotide that is differentially expressed in a prostate cancer cell may comprise a moiety that specifically hybridizes to such a polynucleotide. The kit may optionally provide additional components that are useful in the procedure, including, but not limited to, buffers, developing reagents, labels, reacting surfaces, means for detection, control samples, standards, instructions, and interpretive information.

The present invention further relates to methods of detecting/diagnosing a neoplastic or preneoplastic condition in a mammal (for example, a human). "Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and therametrics (e.g., monitoring a subject's condition to provide information as to the effect or efficacy of therapy).

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

An "effective amount" is an amount sufficient to effect beneficial or desired results, including clinical results. An effective amount can be administered in one or more administrations.

A "cell sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "cell sample" encompasses a clinical sample, and also includes cells in culture, cell supernatants, cell lysates, serum, plasma, biological fluid, and tissue samples.

As used herein, the terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign.

The terms "individual", "subject", "host" and "patient" are used interchangeably herein and refer to any mammalian subject for whom diagnosis, treatment, or therapy is desired, particularly humans. Other subjects may include cattle, dogs, cats, guinea pigs, rabbits, rats, mice, horses, and so on. Examples of conditions that can be detected/diagnosed in accordance with these methods include cancers. Polynucleotides corresponding to genes that exhibit the appropriate expression pattern can be used to detect cancer in a subject. For a review of markers of cancer, see, e.g., Hanahan et al. Cell 100:57-70 (2000).

As used herein, the term "susceptible" refers to a patients for whom a DKKL-1 splice product modulator is an acceptable method of treatment, i.e., a patient who is likely to respond positively. Cancer patients susceptible to DKKL-1 splice product modulator therapy express high levels of DKKL-1 splice products relative to those patients not susceptible to therapy with DKKL-1 splice product modulators. Cancer patients who are not good candidates for therapy with DKKL-1 splice product modulators include cancer patients with tumor samples that lack or have lower levels of DKKL-1 splice products in patient samples.

Biological samples suitable for use in this method include biological fluids such as serum, plasma, pleural effusions, urine and cerebro-spinal fluid, CSF, tissue samples (e.g., mammary tumor or prostate tissue slices) can also be used in the method of the invention, including samples derived from biopsies. Cell cultures or cell extracts derived, for example, from tissue biopsies can also be used.

In some embodiments, the compound is a binding protein, e.g., an antibody, polyclonal or monoclonal, or antigen binding fragment thereof, which can be labeled with a detectable marker (e.g., fluorophore, chromophore or isotope, etc). Where appropriate, the compound can be attached to a solid support such as a bead, plate, filter, resin, etc. Determination of formation of the complex can be effected by contacting the complex with a further compound (e.g., an antibody) that specifically binds to the first compound (or complex). Like the first compound, the further compound can be attached to a solid support and/or can be labeled with a detectable marker.

The identification of elevated levels of the novel DKKL-1 isoform polypeptides in accordance with the present invention makes possible the identification of subjects (patients) that are likely to benefit from adjuvant therapy. For example, a biological sample from a post primary therapy subject (e.g., subject having undergone surgery) can be screened for the presence of circulating protein, the presence of elevated levels of the protein, determined by studies of normal populations, being indicative of residual tumor tissue. Similarly, tissue from the cut site of a surgically removed tumor can be examined (e.g., by immunofluorescence), the presence of elevated levels of product (relative to the surrounding tissue) being indicative of incomplete removal of the tumor. The ability to identify such subjects makes it possible to tailor therapy to the needs of the particular subject. Subjects undergoing non-surgical therapy, e.g., chemotherapy or radiation therapy, can also be monitored, the presence in samples from such subjects of elevated levels of the protein being indicative of the need for continued treatment. Staging of the disease (for example, for purposes of optimizing treatment regimens) can also be affected, for example, by biopsy.

(f) Combination Therapy

In some embodiments, DKKL-1 splice product modulators are administered to the individual in combination with traditional cancer treatments. In some embodiments, the traditional cancer treatment does not interfere with or reduce the effectiveness of the DKKL-1 splice product modutors. Some example traditional cancer treatments include surgery (including, e.g., cryosurgery, segmental resection surgery, radical prostatectomy, lumpectomy, mastectomy, etc.), chemotherapy, radiation therapy (e.g., internal radiation therapy, external beam radiation therapy), brachytherapy (e.g., delivery of radiation directly to the original tumor site and decrease radiation time using a single catheter to perform a breast cancer therapy), hormone ablation therapy (reduction of hormone levels), and the like.

In some embodiments, DKKL-1 splice product modutors are administered to the individual in combination with traditional cancer therapeutics. As used herein, the phrase "traditional cancer therapeutics" refers to other therapeutics (e.g. pharmaceutical compositions) that are used to treat cancer. Examples of traditional cancer therapeutics include, but not limited to, alkylating agents (e.g., cyclophosphamide, ifosfamide), antibiotics which affect nucleic acids (e.g., doxorubicin, bleomycin), platinum compounds (e.g., cisplatin), mitotic inhibitors (e.g., vincristine), antimetabolites (e.g., 5-fluorouracil), camptothecin derivatives (e.g., topotecan), biological response modifiers (e.g., interferon), and hormone therapies (e.g., tamoxifen). Other cancer therapeutics include specific inhibitors that target a specific pathway. Examples of specific inhibitors include, but are not limited to, proteosome inhibitors (e.g. bortozemib, Velcade), protein tyrosine kinase inhibitors (e.g. Gleevec), angiogenesis inhibitors (e.g. Avastin and Tarveca), EGF receptor inhibitors (e.g. Iressa), and the like. Other cancer therapeutics that can be administered include, but are not limited to, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxyurea, idarubicin, ifosfamide, irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, fioguanine/thioguanine, topotecan, treosulfan, vinblastine, vincristine, vindesine, vinorelbine, zometa, and the like.

Certain aspects of the present invention are described in greater detail in the non-limiting examples that follow.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all and only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Detection of Novel Splice Forms of DKKL-1

Expression products of the human DKKL-1 gene were amplified and cloned from Origene "Multiple-choice first-strand cDNA CH-1011-testis"—a gene expression library of the human testis tissue using gene specific primers designed against publicly available sequences of DKKL-1: NM_014419 and AF177398. In addition to the known isoform 1, two novel splice variants of the human DKKL-1 gene were identified by aberrant size and sequenced.

Figure 2:
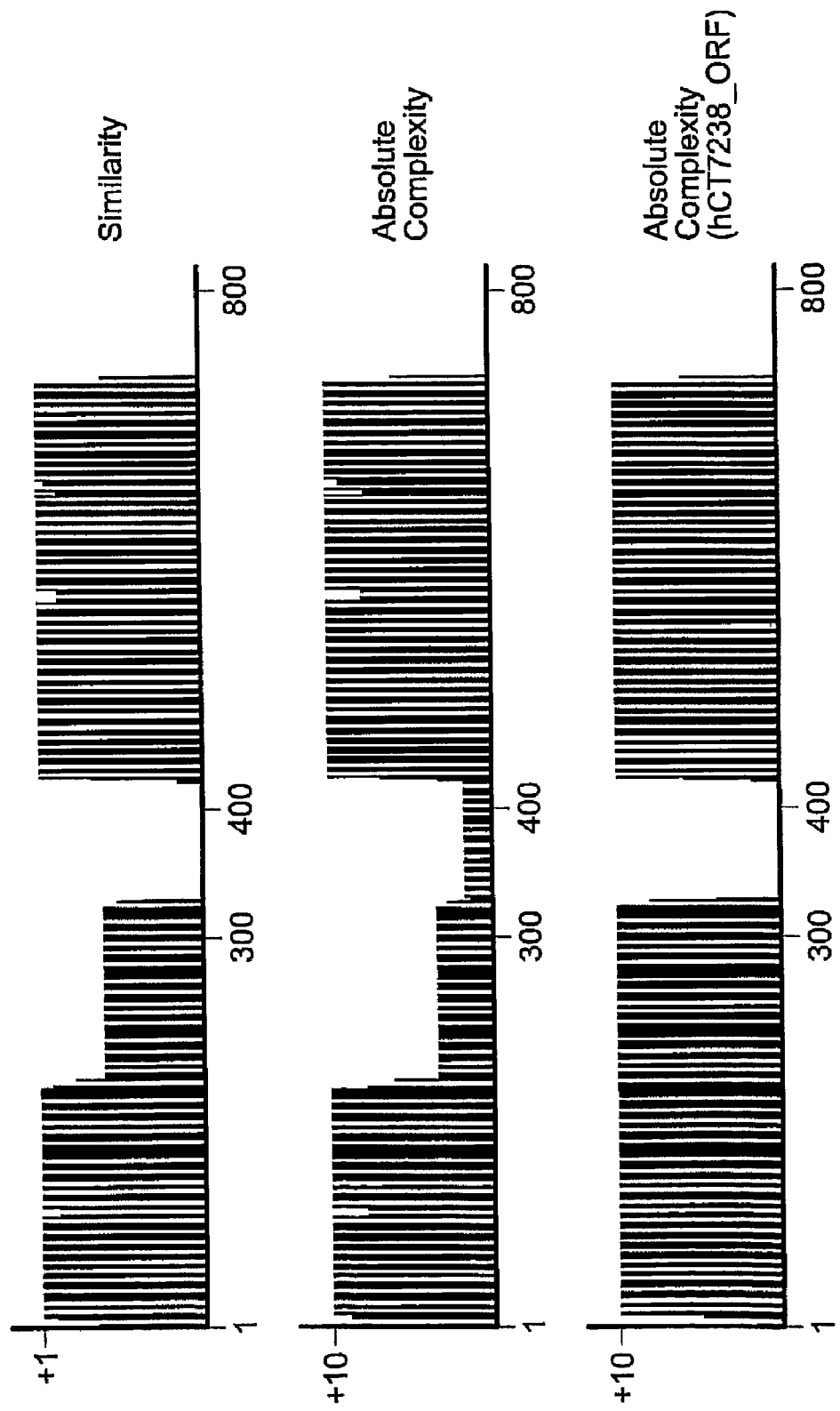
FIG. 2 shows alignment of transcripts of splice variant isoforms of DKKL-1 in terms of complexity.
Figure 5A:
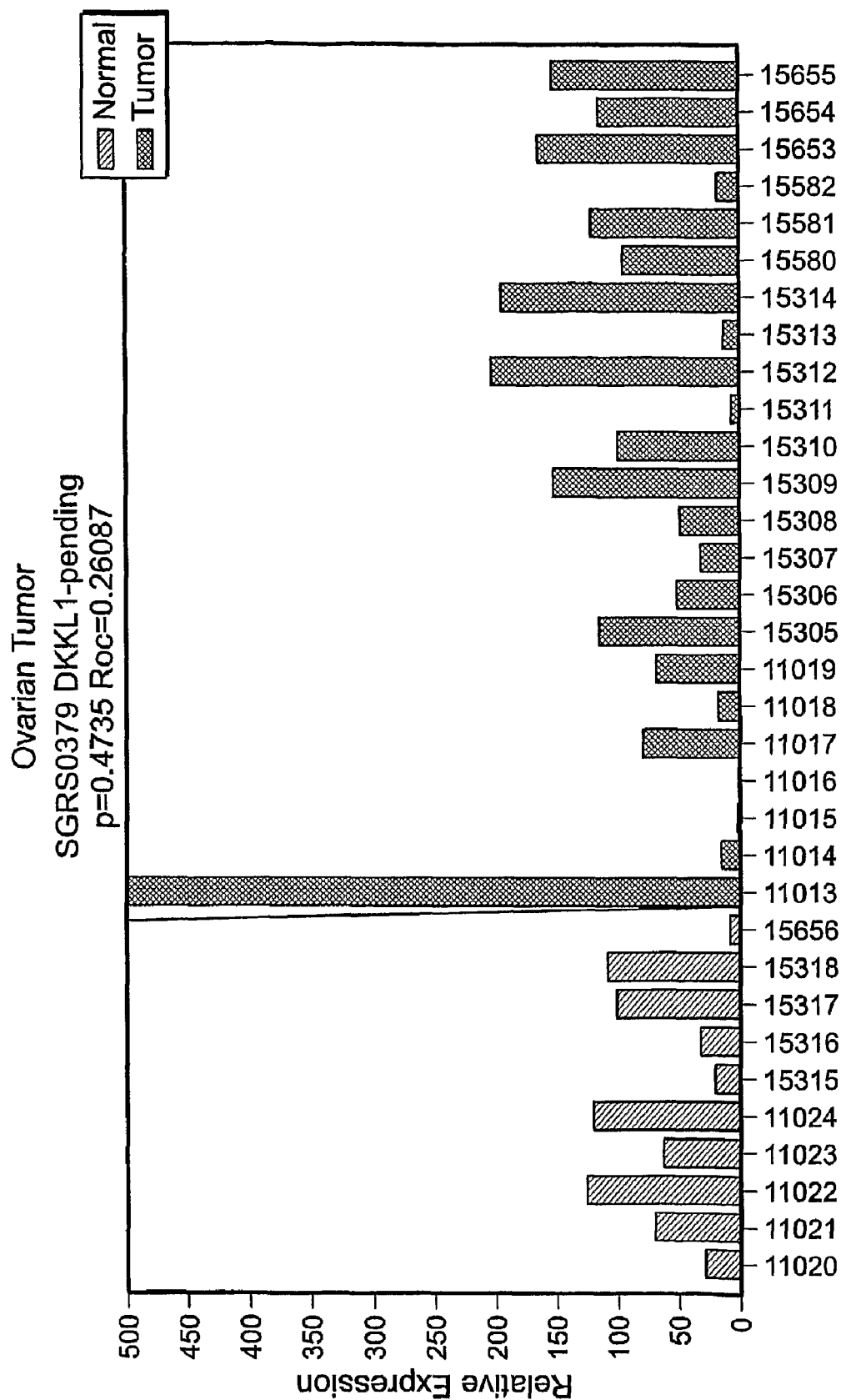
Figure 5B:
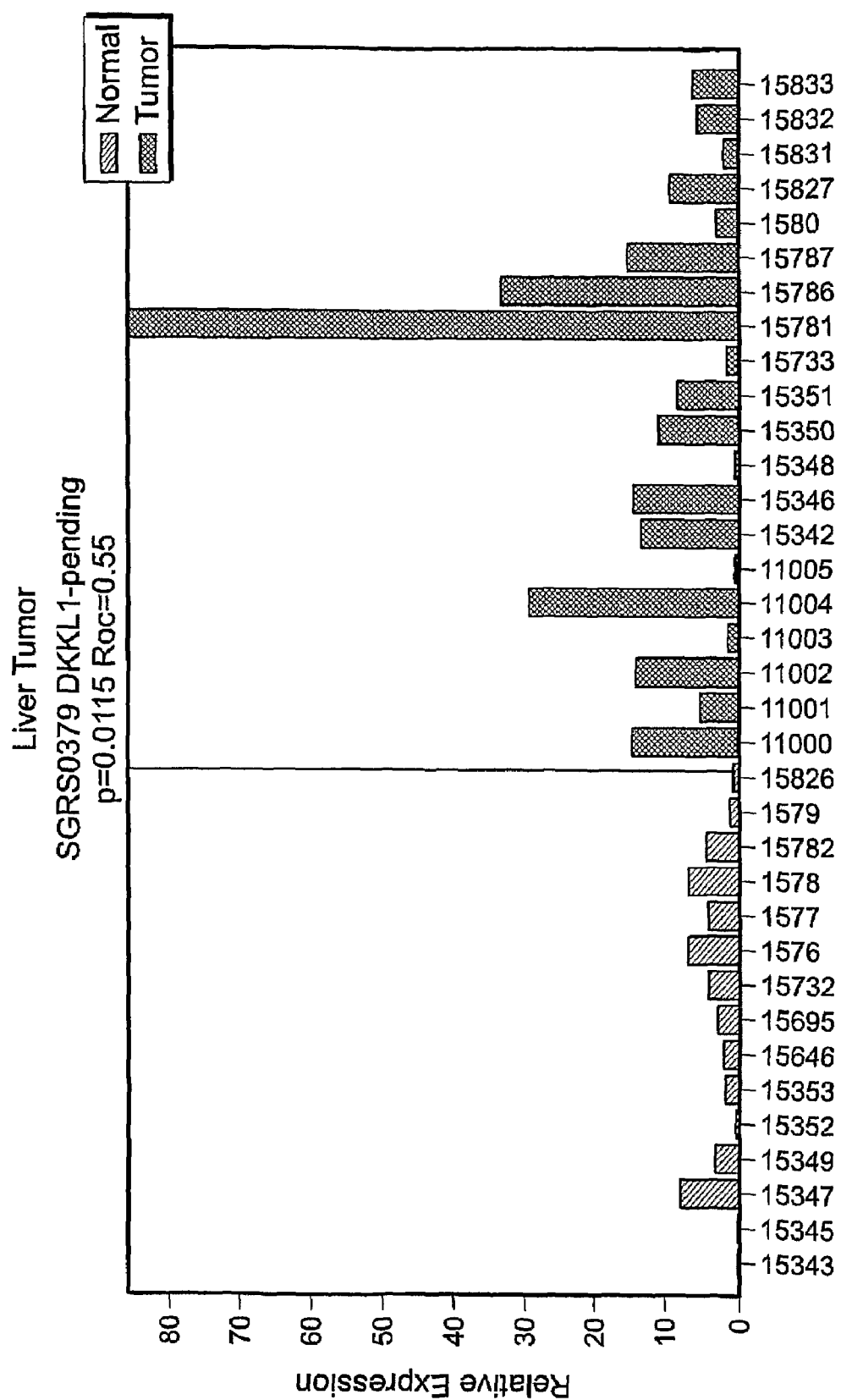
Figure 5C:
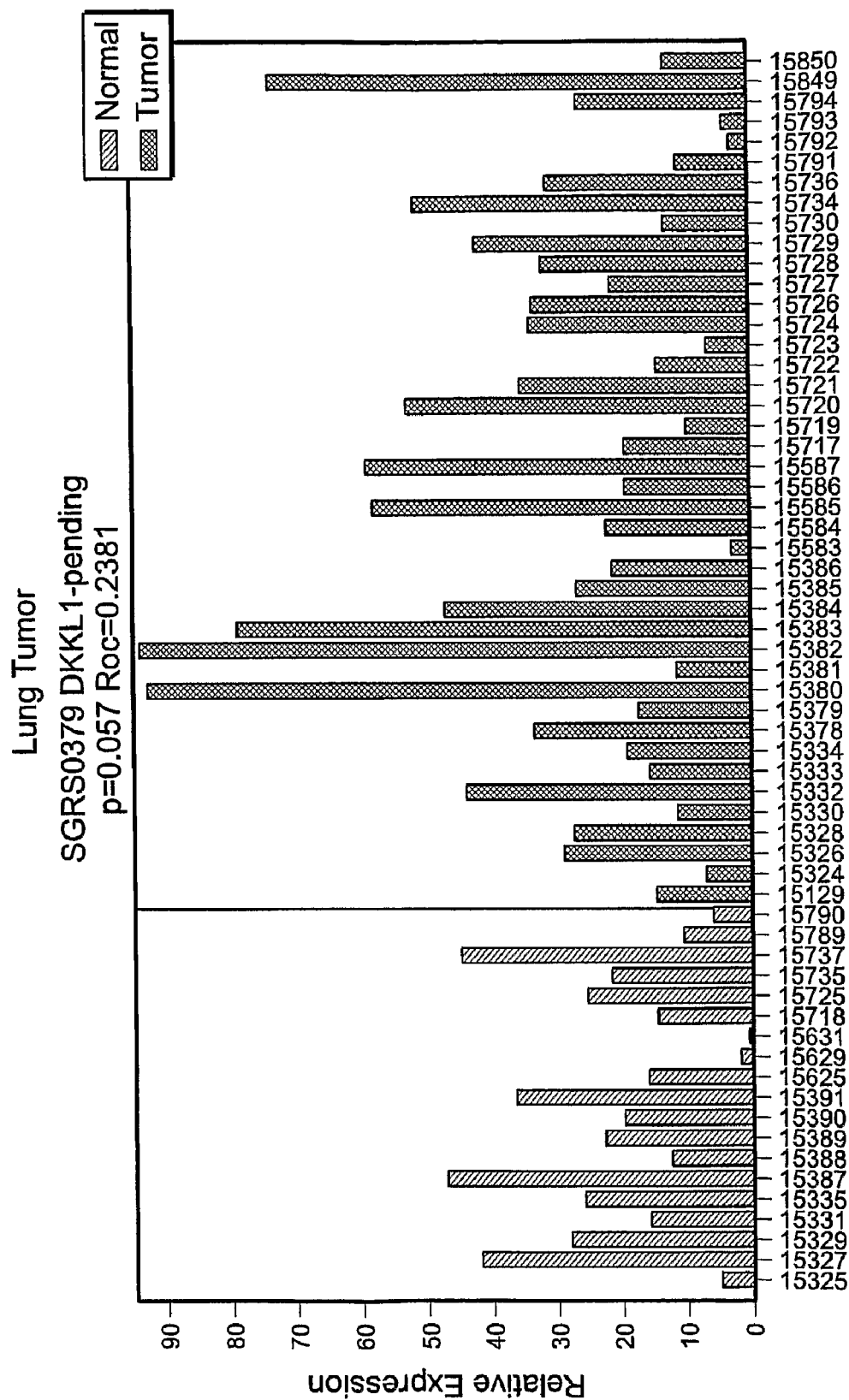
Figure 5D:
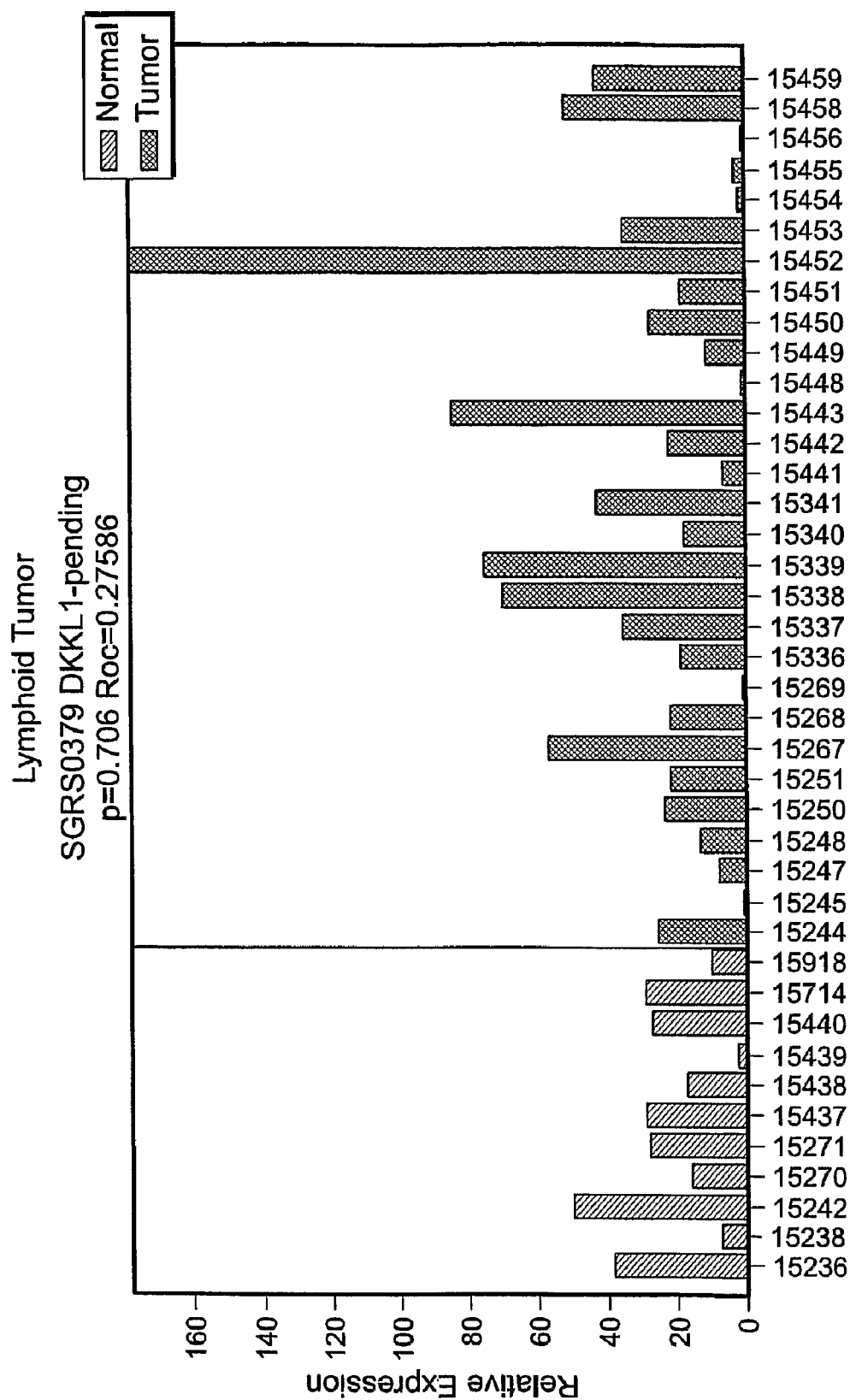
Figure 5E:
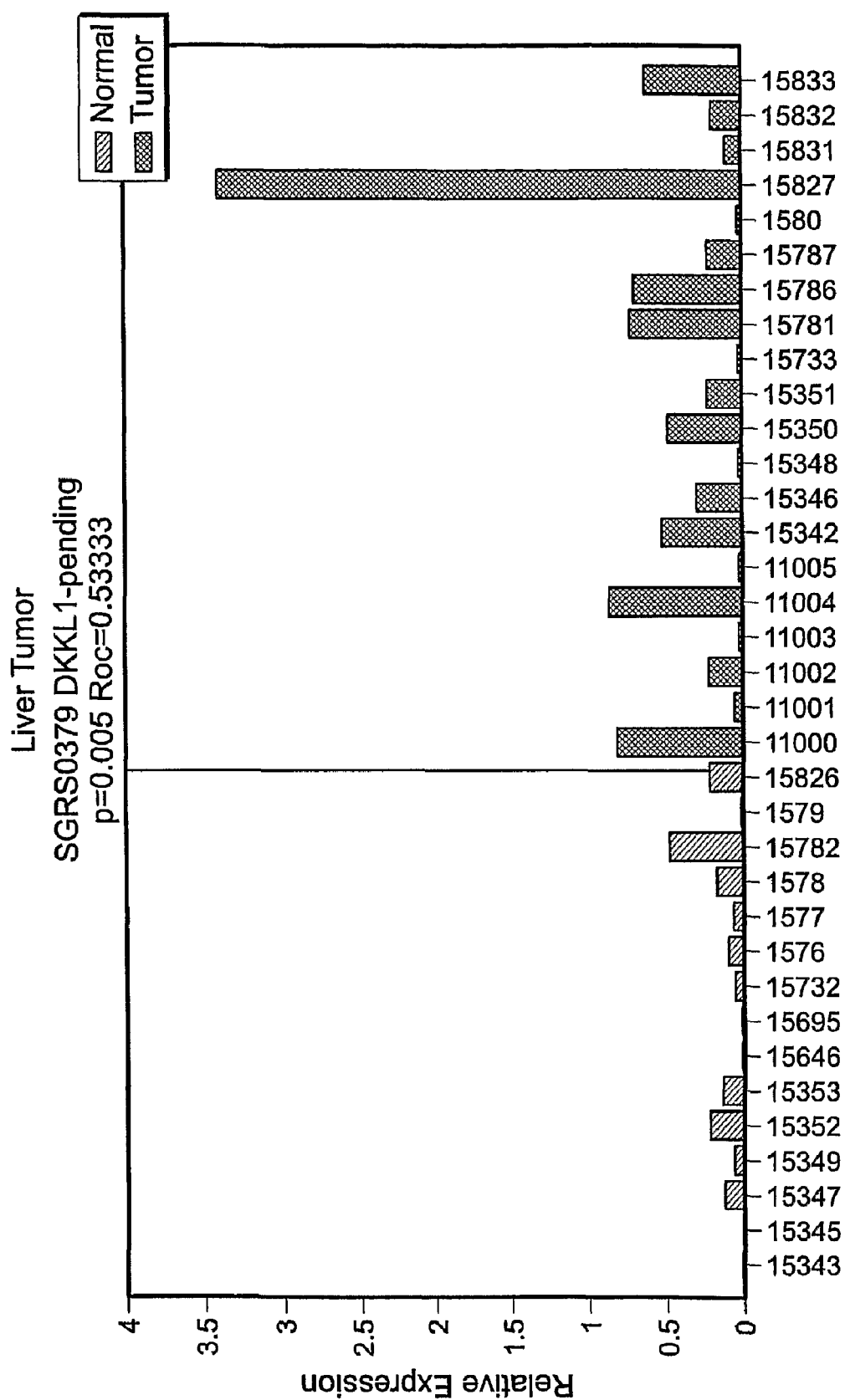
Figure 5F:
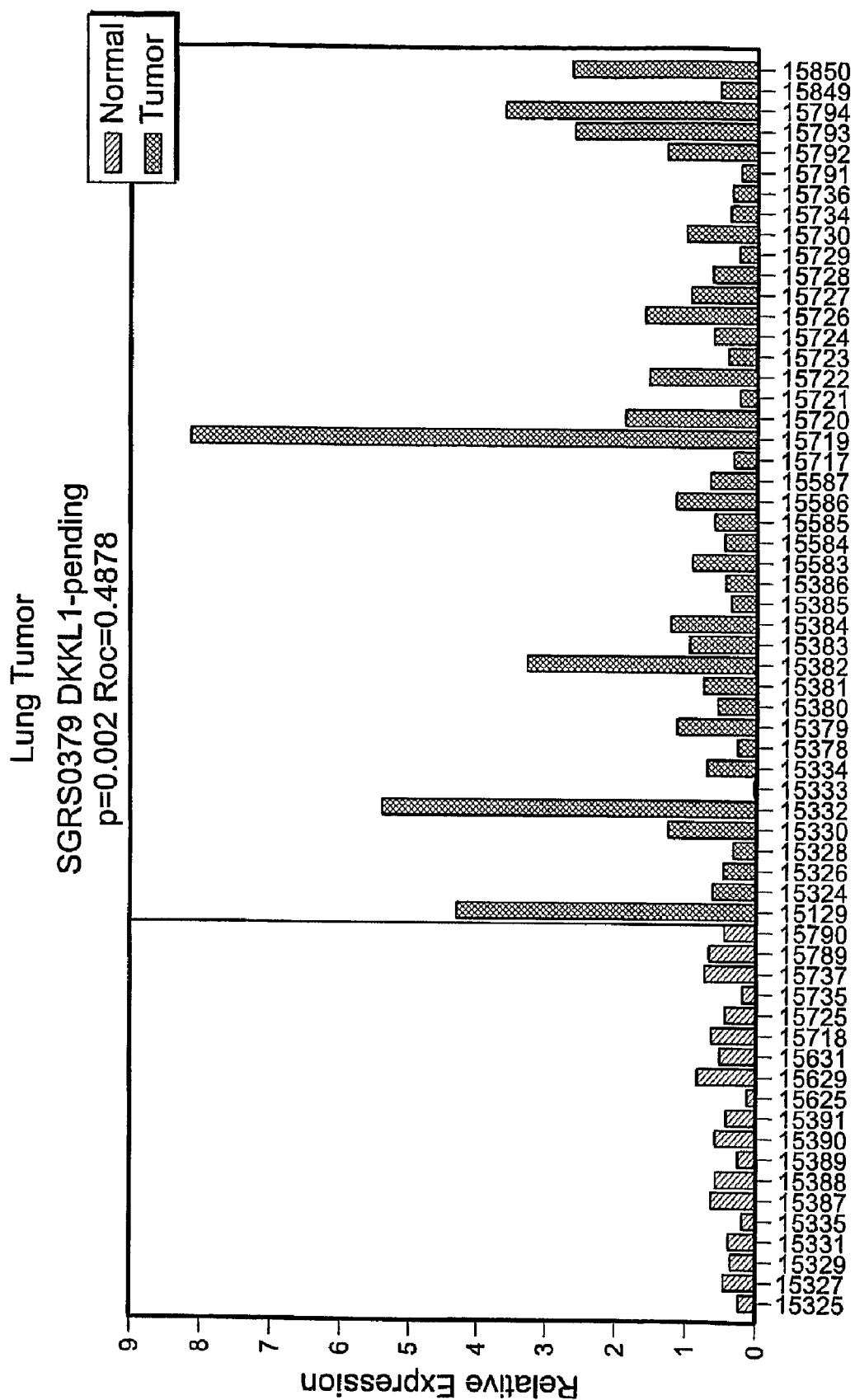

Alignments were performed using the Celera (hCG16206 and hCT_7238) sequences of DKKL-1 as shown in FIG. 1. A diagram of alignment in terms of complexity is shown in FIG. 2 using the coding sequence of the Celera hCT_7238.

Example 2

Characterization of Novel Splice Forms of DKKL-1

Nucleotide sequence alignment of the novel isoforms 2 and 3 of DKKL-1 splice products with the coding sequence of the Celera hCT_7238 are shown in FIGS. 3A-3E. Sagres clones 379-stop, 379-R6, 379-R7, 379-R3 and 379-RS2 represent the known normal splice pattern of isoform 1. The coding sequences were aligned with the sequences of Sagres clones starting at position-4 before the start codon and ending at the stop codon for DKKL-1. A novel isoform 2 comprises the nucleotide sequences of clones 379-R8 and 379-RS3 shown in FIGS. 3A-3E and lacks exon 4. The novel splice junction of isoform 2 spans nucleotides 329-330 of the DKKL-1 coding sequence. A novel isoform 3 comprises the nucleotide sequences of clones 379-R4, 379-R5, 379-R2, 379-RS7 and 379-RS4 shown in FIGS. 3A-3E and lacks exons 3 and 4. The novel splice junction of isoform 3 spans positions 188 and 189 of the DKKL-1 coding sequence.

Polypeptide sequence alignment of the novel isoforms 2 and 3 of DKKL-1 splice products with normal isoform 1 and Celera hCT_7238 is shown in FIGS. 4A-4B. The novel isoform 2 has a novel splice junction spanning positions 108 and 109 of the polypeptide sequences of clones 379-R8 and 379-RS3 shown in FIGS. 4A-4B. The novel isoform 3 comprises the novel splice junction spanning positions 61 and 62 of the polypeptide sequences of clones 379-R4, 379-R5, 379-R2, 379-RS7 and 379-RS4 shown in FIGS. 4A-4B.

All three splice variants (isoforms 1, 2 and 3) were secreted when overexpressed and localized in the plasma membrane and secretory organelles of some cancer cell lines that were tested. This behavior is similar to known human Dickkopf (dkk) proteins.

Example 3

Detection of Elevated Levels of cDNA Associated with Cancer Using Arrays cDNA sequences representing the novel DKKL-1 isoforms to be screened for differential expression in cancer are assayed by hybridization on polynucleotide arrays. The cDNA sequences include cDNA clones isolated from cell lines or tissues of interest. cDNAs are spotted onto reflective slides (Amersham) according to methods well known in the art at a density of 9,216 spots per slide representing 4,068 sequences (including controls) spotted in duplicate, with approximately 0.8 µl of an approximately 200 ng/µl solution of cDNA.

PCR products of selected cDNA clones corresponding to the gene products of interest are prepared in a 50% DMSO solution. These PCR products are spotted onto Amersham aluminum microarray slides at a density of 9216 clones per array using a Molecular Dynamics Generation III spotting robot. Clones are spotted in duplicate, for a total of 4608 different sequences per chip.

cDNA probes are prepared from total RNA obtained by laser capture microdissection (LCM, Arcturus Enginering Inc., Mountain View, Calif.) of tumor tissue samples and normal tissue samples isolated from patients.

Total RNA is first reverse transcribed into cDNA using a primer containing a T7 RNA polymerase promoter, followed by second strand DNA synthesis. cDNA is then transcribed in vitro to produce antisense RNA using the T7 promoter-mediated expression (see, e.g., Luo et al. (1999) Nature Med 5:117-122), and the antisense RNA is then converted into cDNA. The second set of cDNAs are again transcribed in vitro, using the T7 promoter, to provide antisense RNA. This antisense RNA is then fluorescently labeled, or the RNA is again converted into cDNA, allowing for a third round of T7-mediated amplification to produce more antisense RNA. Thus the procedure provides for two or three rounds of in vitro transcription to produce the final RNA used for fluorescent labeling. Probes are labeled by making fluorescently labeled cDNA from the RNA starting material. Fluorescently labeled cDNAs prepared from the tumor RNA sample are compared to fluorescently labeled cDNAs prepared from normal cell RNA sample. For example, the cDNA probes from the normal cells are labeled with Cy3 fluorescent dye (green) and the cDNA probes prepared from suspected cancer cells are labeled with Cy5 fluorescent dye (red).

The differential expression assay is performed by mixing equal amounts of probes from tumor cells and normal cells of the same patient. The arrays are prehybridized by incubation for about 2 hrs at 60° C. in 5×SSC, 0.2% SDS, 1 mM EDTA, and then washing three times in water and twice in isopropanol. Following prehybridization of the array, the probe mixture is then hybridized to the array under conditions of high stringency (overnight at 42° C. in 50% formamide, 5×SSC, and 0.2% SDS. After hybridization, the array is washed at 55° C. three times as follows: 1) first wash in 1×SSC/0.2% SDS; 2) second wash in 0.1×SSC/0.2% SDS; and 3) third wash in 0.1×SSC.

The arrays are then scanned for green and red fluorescence using a Molecular Dynamics Generation III dual color laser-scanner/detector. The images are processed using BioDiscovery Autogene software, and the data from each scan set normalized. The experiment is repeated, this time labeling the two probes with the opposite color in order to perform the assay in both "color directions." Each experiment is sometimes repeated with two more slides (one in each color direction). The data from each scan is normalized, and the level of fluorescence for each sequence on the array expressed as a ratio of the geometric mean of 8 replicate spots/genes from the four arrays or 4 replicate spots/gene from 2 arrays or some other permutation.

Normalization: The objective of normalization is to generate a cDNA library in which all transcripts expressed in a particular cell type or tissue are equally represented (S. M. Weissman, Mol. Biol. Med. 4(3):133-143 (1987); Patanjali, et al., Proc. Natl. Acad. Sci. USA 88(5):1943-1947 (1991)), and therefore isolation of as few as 30,000 recombinant clones in an optimally normalized library may represent the entire gene expression repertoire of a cell, estimated to number 10,000 per cell.

Total RNA is extracted from harvested cells using RNeasy™ Protect Kit (Qiagen, Valencia, Calif.), following manufacturer's recommended procedures. RNA is quantified using RiboGreen™ RNA quantification kit (Molecular Probes, Inc. Eugene, Oreg.). One μg of total RNA is reverse transcribed and PCR amplified using SMART™ PCR cDNA synthesis kit (CloneTech, Palo Alto, Calif.). The cDNA products are size-selected by agarose gel electrophoresis using standard procedures (Sambrook, J. T., et al. Molecular Cloning: A Laboratory Manual, 2d ed., Cold Spring Harbor Laboratory Press, NY). The cDNA is extracted using Bio 101 Geneclean® II kit (Qbiogene, Carlsbad, Calif.). Normalization of the cDNA is carried out using kinetics of hybridization principles: 1.0 μg of cDNA is denatured by heat at 100° C. for 10 minutes, then incubated at 42° C. for 42 hours in the presence of 120 mM NaCl, 10 mM Tris.HCl (pH=8.0), 5 mM EDTA.Na+ and 50% formamide. Single-stranded cDNA ("normalized") is purified by hydroxyapatite chromatography (#130-0520, BioRad, Hercules, Calif.) following the manufacturer's recommended procedures, amplified and converted to double-stranded cDNA by three cycles of PCR amplification, and cloned into plasmid vectors using standard procedures (Sambrook, J. T., et al. Molecular Cloning: A Laboratory Manual, 2d ed., Cold Spring Harbor Laboratory Press, NY). All primers/adaptors used in the normalization and cloning process are provided by the manufacturer in the SMART™ PCR cDNA synthesis kit (ClonTech, Palo Alto, Calif.). Supercompetent cells (XL-2 Blue Ultracompetent Cells, Stratagene, Calif.) are transfected with the normalized cDNA libraries, plated on solid media and grown overnight at 36° C.

The sequences of 10,000 recombinants per normalized library are analyzed by capillary sequencing using the ABI PRISM 3700 DNA Analyzer (Applied Biosystems, California). To determine the representation of transcripts in a library, BLAST analysis is performed on the clone sequences to assign transcript identity to each isolated clone, i.e., the sequences of the isolated polynucleotides are first masked to eliminate low complexity sequences using the XBLAST masking program (Claverie "Effective Large-Scale Sequence Similarity Searches," Computer Methods for Macromolecular Sequence Analysis, Doolittle, ed., Meth. Enzymol. 266: 212-227 Academic Press, NY, N.Y. (1996); see particularly Claverie, in "Automated DNA Sequencing and Analysis Techniques" Adams et al., eds., Chap. 36, p. 267 Academic Press, San Diego, 1994 and Claverie et al. Comput. Chem. (1993) 17:191). Generally, masking does not influence the final search results, except to eliminate sequences of relative little interest due to their low complexity, and to eliminate multiple "hits" based on similarity to repetitive regions common to multiple sequences, e.g., Alu repeats. The remaining sequences are then used in a BLASTN vs. GenBank search. The sequences are also used as query sequence in a BLASTX vs. NRP (non-redundant proteins) database search.

Automated sequencing reactions are performed using a Perkin-Elmer PRISM Dye Terminator Cycle Sequencing Ready Reaction Kit containing AmpliTaq DNA Polymerase, FS, according to the manufacturer's directions. The reactions are cycled on a GeneAmp PCR System 9600 as per manufacturer's instructions, except that they are annealed at 20° C. or 30° C. for one minute. Sequencing reactions are ethanol precipitated, pellets are resuspended in 8 microliters of loading buffer, 1.5 microliters is loaded on a sequencing gel, and the data is collected by an ABI PRISM 3700 DNA Sequencer. (Applied Biosystems, Foster City, Calif.).

The number of times a sequence is represented in a library is determined by performing sequence identity analysis on the cloned cDNA sequences and assigning transcript identity to each isolated clone. First, each sequence is checked to determine if it is a bacterial, ribosomal, or mitochondrial contaminant. Such sequences are excluded from the subsequent analysis. Second, sequence artifacts, such as vector and repetitive elements, are masked and/or removed from each sequence.

The remaining sequences are compared via BLAST (Altschul et. al, J. Mol. Biol., 215:40, 1990) to GenBank and EST databases for gene identification and are compared with each other via FastA (Pearson & Lipman, PNAS, 85:2444, 1988) to calculate the frequency of cDNA appearance in the normalized cDNA library. The sequences are also searched against the GenBank and GeneSeq nucleotide databases using the BLASTN program (BLASTN 1.3 MP: Altschul et al., J. Mol. Bio. 215:403, 1990). Fourth, the sequences are analyzed against a non-redundant protein (NRP) database with the BLASTX program (BLASTX 1.3 MP: Altschul et al., supra). This protein database is a combination of the Swiss-Prot, PIR, and NCBI GenPept protein databases. The BLASTX program is run using the default BLOSUM-62 substitution matrix with the filter parameter: "xnu+seg". The score cutoff utilized is 75. Assembly of overlapping clones into contigs is done using the program Sequencher (Gene Codes Corp.; Ann Arbor, Mich.). The assembled contigs are analyzed using the programs in the GCG package (Genetic Computer Group, University Research Park, 575 Science Drive, Madison, Wis. 53711) Suite Version 10.1.

Example 4

Detection of Novel DKKL-1 Isoforms in Human Cancer Cells and Tissues

DNA from human cancer tissues, human colon, normal human tissues and from other human cell lines are extracted following the procedure of Delli Bovi et al. (1986, Cancer Res. 46:6333-6338). The DNA is resuspended in a solution containing 0.05 M Tris HCl buffer, pH 7.8, and 0.1 mM EDTA, and the amount of DNA recovered is determined by microfluorometry using Hoechst 33258 dye. Cesarone, C. et al., Anal Biochem 100:188-197 (1979).

Polymerase chain reaction (PCR) is performed using Taq polymerase following the conditions recommended by the manufacturer (Perkin Elmer Cetus) with regard to buffer, Mg2+, and nucleotide concentrations. Thermocycling is performed in a DNA cycler by denaturation at 94° C. for 3 min. followed by either 35 or 50 cycles of 94° C. for 1.5 min., 50° C. for 2 min. and 72° C. for 3 min. The ability of the PCR to amplify the selected regions of the gene is tested by using a cloned polynucleotide(s) as a positive template(s). Optimal Mg2+, primer concentrations and requirements for the different cycling temperatures are determined with these templates. The master mix recommended by the manufacturer is used. To detect possible contamination of the master mix components, reactions without template are routinely tested.

Example 5

Expression of Cloned Polynucleotides in Host Cells

To study the protein products of the novel DKKL-1 isoforms, restriction fragments from isoform 2 or 3 cDNA are cloned into the expression vector pMT2 (Sambrook, et al., Molecular Cloning: A Laboratory Manual, Cold Spring Harbor Laboratory Press pp 16.17-16.22 (1989)) and transfected into COS cells grown in DMEM supplemented with 10% FCS. Transfections are performed employing calcium phosphate techniques (Sambrook, et al (1989) pp. 16.32-16.40, supra) and cell lysates are prepared forty-eight hours after transfection from both transfected and untransfected COS cells. Lysates are subjected to analysis by immunoblotting using anti-peptide antibody.

In immunoblotting experiments, preparation of cell lysates and electrophoresis are performed according to standard procedures. Protein concentration is determined using BioRad protein assay solutions. After semi-dry electrophoretic transfer to nitrocellulose, the membranes are blocked in 500 mM NaCl, 20 mM Tris, pH 7.5, 0.05% Tween-20 (TTBS) with 5% dry milk. After washing in TTBS and incubation with secondary antibodies (Amersham), enhanced chemiluminescence (ECL) protocols (Amersham) are performed as described by the manufacturer to facilitate detection.

Example 6

Generation of Antibodies Against Polypeptides

Polypeptides encoded by the novel isoforms are synthesized or isolated from bacterial or other (e.g., yeast, baculovirus) expression systems and conjugated to rabbit serum albumin (RSA) with m-maleimido benzoic acid N-hydroxysuccinimide ester (MBS) (Pierce, Rockford, Ill.). Immunization protocols with these peptides are performed according to standard methods. Initially, a pre-bleed of the rabbits is performed prior to immunization. The first immunization includes Freund's complete adjuvant and 500 μg conjugated peptide or 100 μg purified peptide. All subsequent immunizations, performed four weeks after the previous injection, include Freund's incomplete adjuvant with the same amount of protein. Bleeds are conducted seven to ten days after the immunizations.

For affinity purification of the antibodies, the corresponding polypeptide is conjugated to RSA with MBS, and coupled to CNBr-activated Sepharose (Pharmacia, Uppsala, Sweden). Antiserum is diluted 10-fold in 10 mM Tris-HCl, pH 7.5, and incubated overnight with the affinity matrix. After washing, bound antibodies are eluted from the resin with 100 mM glycine, pH 2.5.

Example 7

Generation of Monoclonal Antibodies Against a Novel DKKL-1 Isoform Polypeptide

A non-denaturing adjuvant (Ribi, R730, Corixa, Hamilton Mont.) is rehydrated to 4 ml in phosphate buffered saline. 100 μl of this rehydrated adjuvant is then diluted with 400 μl of Hank's Balanced Salt Solution and this is then gently mixed with the cell pellet used for immunization. Approximately 500 μg conjugated peptide or 100 μg purified peptide and Freund's complete are injected into Balb/c mice via foot-pad, once a week. After 6 weeks of weekly injection, a drop of blood is drawn from the tail of each immunized animal to test the titer of antibodies against polypeptides using FACS analysis. When the titer reaches at least 1:2000, the mice are sacrificed in a CO2 chamber followed by cervical dislocation. Lymph nodes are harvested for hybridoma preparation. Lymphocytes from mice with the highest titer are fused with the mouse myeloma line X63-Ag8.653 using 35% polyethylene glycol 4000. On day 10 following the fusion, the hybridoma supernatants are screened for the presence of specific monoclonal antibodies by fluorescence activated cell sorting (FACS). Conditioned medium from each hybridoma is incubated for 30 minutes with a combined aliquot of PC3, Colo-205, LnCap, or Panc-1 cells. After incubation, the cell samples are washed, resuspended in 0.1 ml diluent and incubated with 1 µg/ml of FITC conjugated F(ab')2 fragment of goat anti-mouse IgG for 30 min at 40C. The cells are washed, resuspended in 0.5 ml FACS diluent and analyzed using a FACScan cell analyzer (Becton Dickinson; San Jose, Calif.). Hybridoma clones are selected for further expansion, cloning, and characterization based on their binding to the surface of one or more of cell lines which express the polypeptide as assessed by FACS.

Example 8

ELISA Assay for Detecting DKKL-1 Isoform Antigens

To test blood samples for antibodies that bind specifically to recombinantly produced antigens encoded by the novel splice forms of DKKL-1, the following procedure is employed. After a recombinant protein is purified, the recombinant protein is diluted in PBS to a concentration of 5 µg/ml (500 ng/100 µl). One hundred (100) microliters of the diluted antigen solution is added to each well of a 96-well Immulon 1 plate (Dynatech Laboratories, Chantilly, Va.), and the plate is then incubated for 1 hour at room temperature, or overnight at 4° C., and washed 3 times with 0.05% Tween 20 in PBS. Blocking to reduce nonspecific binding of antibodies is accomplished by adding to each well 200 µl of a 1% solution of bovine serum albumin in PBS/Tween 20 and incubation for 1 hour. After aspiration of the blocking solution, 100 µl of the primary antibody solution (anticoagulated whole blood, plasma, or serum), diluted in the range of 1/16 to 1/2048 in blocking solution, is added and incubated for 1 hour at room temperature or overnight at 4° C. All DKKL-1 isoforms may be detected using the rabbit polyclonal antibody against DKKL-1 (379-3). DKKL-1-isoform 2 can be detected using A8.7 (isoform 2 specific antibody). DKKL-1 isoform 1 can be detected using anti-human Soggy-1 (isoform I specific antibody from R & D Systems). Bound antibody is detected using standard secondary antibodies conjugated to horseradish peroxidase (Organon Teknika, Durham, N.C.), diluted 1/500 or 1/1000 in PBS/Tween 20, 100 µl of o-phenylenediamine dihydrochloride (OPD, Sigma) solution is added to each well and incubated for 5-15 minutes. The OPD solution is prepared by dissolving a 5 mg OPD tablet in 50 ml 1% methanol in H2O and adding 50 µl 30% H2O2 immediately before use. The reaction is stopped by adding 25 l of 4M H2SO4. Absorbances are read at 490 nm in a microplate reader (Bio-Rad). More sensitive ELISA formats such as the one described by Zhang H et al., (Nature Medicine, A sensitive and high-throughput assay to detect low abundance proteins in serum. Mar. 12, 2006 (online publication)) can also be utilized.

Example 9

Generation of Transgenic Animals Expressing Polypeptides as a Means for Testing Therapeutics Novel DKKL-1 isoform nucleic acids are used to generate genetically modified non-human animals, or site specific gene modifications thereof, in cell lines, for the study of function or regulation of prostate tumor-related genes, or to create animal models of diseases, including prostate cancer. The term "transgenic" is intended to encompass genetically modified animals having an exogenous gene that is stably transmitted in the host cells where the gene may be altered in sequence to produce a modified protein, or having an exogenous LTR promoter operably linked to a reporter gene. Transgenic animals may be made through a nucleic acid construct randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

The modified cells or animals are useful in the study of gene function and regulation. Specific constructs of interest include, but are not limited to, antisense constructs to block gene expression, expression of dominant negative gene mutations, and over-expression of a gene. Expression of a gene or variants thereof in cells or tissues where it is not normally expressed or at abnormal times of development is provided. In addition, by providing expression of proteins derived from DKKL-1 polynucleotides in cells in which it is otherwise not normally produced, changes in cellular behavior can be induced.

DNA constructs for random integration need not include regions of homology to mediate recombination. Conveniently, markers for positive and negative selection are included. For various techniques for transfecting mammalian cells, see Keown et al., Methods in Enzymology 185:527-537 (1990).

For embryonic stem (ES) cells, an ES cell line is employed, or embryonic cells are obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells are transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting chimeric animals screened for cells bearing the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs are maintained as allogeneic or congenic grafts or transplants, or in in vitro culture. The transgenic animals may be any non-human mammal, such as laboratory animals, domestic animals, etc. The transgenic animals are used in functional studies, drug screening, etc., e.g. to determine the effect of a candidate drug on prostate cancer, to test potential therapeutics or treatment regimens, etc.

Example 10

RT-PCR Analysis of Primary Human Tumor Samples using Taqman Primers and Probes

RT-PCR analysis of primary tumor samples was divided into 4 major steps: 1) RNA purification from primary normal and tumor tissues; 2) Generation of first strand cDNA from the purified tissue RNA for Real Time Quantitative PCR; 3) Setup RT-PCR for gene expression using ABI PRISM 7900HT Sequence Detection System tailored for 384-well reactions; 4) Analyze RT-PCR data by statistical methods to identify genes differentially expressed (up-regulated) in cancer.

Using Qiagen RNeasy mini Kit CAT#74106, tissue samples typically yielded approximately 30 µg of RNA and typically resulted in a final concentration of approximately 200 ng/µl if 150 µl of elution buffer was used. After RNA was extracted, Ribogreen quantitation reagents from Molecular Probes were used to determine yield and concentration of RNA according to manufacture's protocol. The Integrity of extracted RNA was assessed on EtBr stained agarose gel to determine if the 28S and 18S band have equal intensity. Integrity of extracted RNA was also assessed using Agilent 2100 according to manufacture's protocol. The Agilent Bioanalyzer/"Lab-On-A-Chip" is a micro-fluidics system that generates an electropherogram of a RNA sample. By observing the ratio of the 18S and 28S bands and the smoothness of the baseline a determination of the level of RNA degradation can be made. Samples having a 28S:18S ratio below 1 were discarded.

RNA samples were also examined by RT-PCR to determine level of genomic DNA contamination during extraction. In general, RNA samples were assayed directly using validated Taqman primers and probes for DKKL-1 in the presence and absence of Reverse Transcriptase. 12.5 ng of RNA was used per reaction in quadruplicate in a 384 wells format in a volume of 5 ul per well. (2 ul of RNA+3 ul of RT+ or RT– master mix). The following thermocycle parameters were used (2-step PCR):

TABLE 1

Thermocycling Parameters

| | Step | | | |
|---|---|---|---|---|
| | Reverse Transcription | Amp. Gold Activation | PCR 40 CYCLES | |
| | HOLD | HOLD | Denature | Anneal/Extend |
| Temperature | 48 C. | 95 C. | 95 C. | 60 C. |
| Time | 30 min. | 10 min. | 15 sec. | 1 min |

RNA was arrayed for cDNA synthesis. In general, a minimum of 10 normals and 20 tumors were required for each tumor type. Four control samples were placed at the end of the panel: hFB, hrRNA, hgDNA and water (in that order). An additional NTC control (water) was placed in well A2. RNA samples were normalized to 100 ng/µl in Nuclease-free water. Eleven µg of RNA was used per panel in a total volume of 110 µl. After normalization was complete, the block was sealed using the heat sealer with easy peel foil @ 175° C. for 2 seconds. The block was stored at –80° C. until cDNA synthesis.

The reaction mixture set forth in Table 2 was prepared in advance of analysis:

TABLE 2

Reaction mixture

| Reagents | 1 RXN Volumes (µl) |
|---|---|
| 10X Taqman RT BUFFER | 1 |
| 25 mM Magnesium chloride | 2.2 |
| 10 mM deoxyNTPS mixture | 2 |
| 50 uM Random Hexamer | 0.5 |
| Rnase inhibitor | 0.2 |
| 50 u/ul MultiScribe Rev. Transcriptase | 0.25 |
| Water | 0.85 |

Arrayed RNA in a 96 well block (11 µg) was distributed to daughter plates using Hydra to create 1 ug of cDNA synthesis per 96 well plate. Each of these daughter plate was used to setup RT reaction using the thermocycle parameters set forth in Table 3:

TABLE 3

Thermocycle parameters

| | Step | | |
|---|---|---|---|
| | Incubation Hold | RT Hold | RT Inactivation Hold |
| Time | 10 min. | 30 min. | 5 min. |
| Temperature | 25 C. | 48 C. | 95 C. |

Upon completion of thermocyling, the plates were removed from cycler and using the Hydra pipet, 60 µl of 0.016M EDTA solution was added into every well of the cDNA plates.

Ninety-four (94) µl of Ambion water was mixed with 141 µl of FRT (Forward and Reverse primers and Target probe). Primers used were as follows: SGP1113 (forward sequence; GCCTCCAGAGCCTACTCCAA; (SEQ ID NO:7); reverse sequence; GGGCAGAGAATAAGCTGTCTATGC (SEQ ID NO:8); probe sequence AGCCGACTTTTCCTG; (SEQ ID NO:9)) was used to detect isoforms I and II, while SGP1129 (forward sequence GCCTCCAGAGCCTACTCCAA (SEQ ID NO:10); reverse sequence GGTACCAGGGCCTCCT-TCTC; (SEQ ID NO:11); and probe sequence TGAAAG-TACCCAGGATGG; (SEQ ID NO:12)) was used to detect isoform III.

The cocktail was stored at 4° C. until ready to run. (–20° C. if longer than 1 day). Master mix will be added to cocktails when ready to run cocktails.

Two µl of cDNA from the arrayed 96-well plates were added to the 3 µl of Taqman Master Mix to makeup a 5 µl QPCR reaction.

TABLE 4

QPCR reaction

| | 1 rxn volume | 470 RXNS | |
|---|---|---|---|
| TaqMan Master Mix | | | |
| TaqMan Universal Master Mix Lot# | 2.5 µl | 1175µ | |
| Forward Primer working stock | 0.1 µl | 7;47µ | |
| Reverse Primer working stock | 0.1 µl | 7;47µ | }141 µl |
| Probe working stock | 0.1 µl | 47µ | |
| Water | 0.2 µl | 94µ | |
| Final Volume | 3.0 µl | 1410µ | |

The expression level of a target gene in both normal and tumor samples was determined using Quantitative RT-PCR using the ABI PRISM 7900HT Sequence Detection System (Applied Biosystems, California). The method is based on the quantitation of the initial copy number of target template in comparison to that of a reference (normalizer) housekeeper gene (Pre-Developed TaqMan® Assay Reagents Gene Expression Quantification Protocol, Applied Biosystems, 2001). Accumulation of DNA product with each PCR cycle is related to amplicon efficiency and the initial template concentration. Therefore the amplification efficiency of both the target and the normalizer must be similar. The threshold cycle (CT), which is dependent on the starting template copy number and the DNA amplification efficiency, is a PCR cycle during which PCR product growth is exponential. Each assay is performed in quadruplicates; therefore, 4 CT values are obtained for the target gene in a given sample.

Simultaneously, the expression level of a group of housekeeper genes was also measured in the same fashion. The outlier within the 4 quadruplicates is detected and removed if the standard deviation of the remaining 3 triplicates is 30% or less compared to the standard deviation of the original 4 quadruplicates. The prevalence of the isoform tested for in each tumor type was also determined.

| Tumor Type | Incidence |
| --- | --- |
| Ovary | 26% |
| Lung | 24-49% |
| Liver | 53-55% |
| Breast | 30% |
| Lymphoma | 28% |

Figure 13:
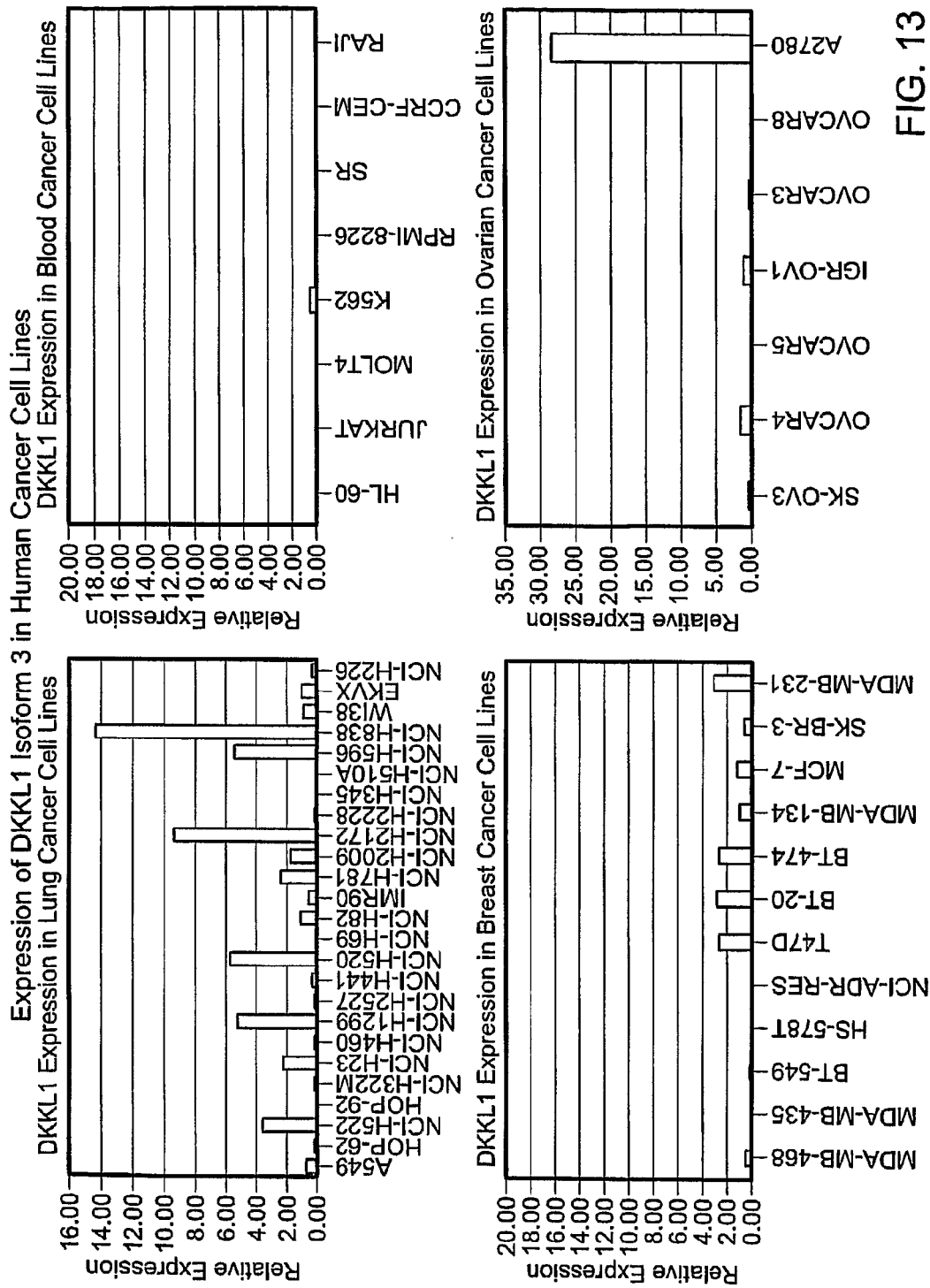
FIGS. 13 and 14 depict relative expression of DKKL-1 isoform 3 in human cancer cell lines.
Figure 14:
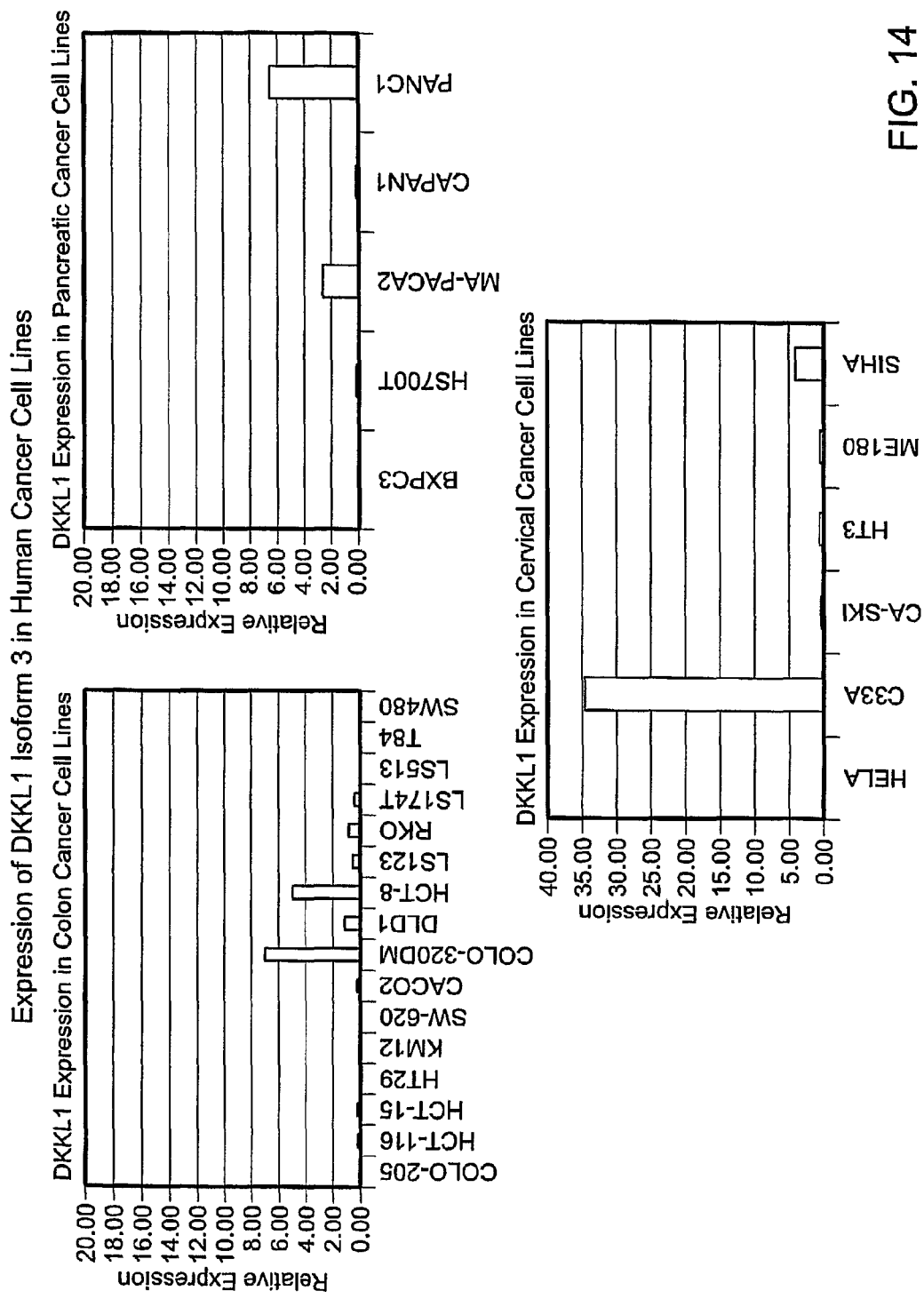

The highest incidence was 55% in liver and the HiFC value was 7.3. QPCR data on primary tumors (panel of minimum 10 normal & 20 tumor samples) indicated that DKKL-1-isoforms 1 and 2 were overexpressed in lung, ovary, lymphoid and liver cancer. QPCR data indicated that DKKL-1-isoform 3 was overexpressed in lung, breast and liver cancer (see FIGS. 5A-G). FIGS. 13 and 14 depict relative expression of DKKL-1 isoform 3 in human cancer cell lines.

Example 11

Isoform Specific Antibodies

Mice were immunized with DKKL-1 isoform 2 or DKKL-1 isoform 3 recombinant purified protein generated by a baculovirus expression system. Immunization was by intraperitoneal injection and was accomplished by three injections. Antigen was mixed with adjuvant and injected intraperitoneally.

On day 25 serum samples were collected by retro-orbital bleeding. No more than 200 μL of whole blood were collected at one time. Serum samples were used to determine antibody titers. Best responders were selected for spleenic fusion at completion of the immunization (14 weeks from the initial immunization).

Detailed Immunization Procedure:

Day 0: injection 100 μL injection volume/mouse. 50% Complete Freunds Adjuvant (volume/volume) with antigen diluted in PBS to 10 g/100 μL (per mouse)=100 μg/mL. The adjuvant and antigen mixture were emulsified thoroughly before injection.

Day 14, Day 28, and Day 42: 100 μL injection volume/mouse. 50% Incomplete Freunds Adjuvant (volume/volume) with antigen diluted in PBS to 5 μg/100 L (per mouse)=50 μg/mL. The adjuvant and antigen mixture were emulsified thoroughly before injection.

Day 56: Final boost 100 uL injection volume/mouse. No adjuvant, 5 μg antigen/mouse. Final boost was injected 50% IP and 50% intravenous.

Day 60: fusion harvest of spleens. At least 2 mice spleens were harvested to go into the fusion.

Procedure for the Electrofusion of Lymphocytes from Mice to Form Hybridomas:

Spleens were obtained from immunized mice. Cells were released from tissues using 15 ml glass tissue grinder. Cells were collected in 50 mL conical tubes with 15 ml of cold DMEM media. Cell suspensions were passed through a 70 μm cell strainer. Cell strainer was rinsed with enough DMEM to bring the volume up to 50 mL. Cells were centrifuged at 1200 rpm (500×g) for 8 minutes to form pellet.

Supernatant was discarded. Cells released from spleens contained red blood cells and need to be lysed. Spleen cell pellet was resuspended in 5 mL of WFI quality water. Cells was left in pure water for a very brief period of time <30 seconds. 45 mL DMEM was added onto cell suspension. Cell suspensions were passed through a 70 μm cell strainer and centrifuged at 1200 rpm (500×g) for 8 minutes to pellet cells. Cells were resuspended in DMEM and aliquoted for counting.

Cells were resuspended at $1 \times 10^8$ cells/mL in DMEM using pre-determined cell number. One hundred (100) μL of anti-CD90 thy 1.2 antibody conjugated micro-beads (Myltenyi, MACS 120-000-295) was added for every $1 \times 10^8$ cells. Beads and cells were mixed thoroughly and incubateed for 15 minutes at 4° C.

Shortly before needed in the fusion protocol, the fusion partner cells were collected. Cell suspensions from spinner flasks or T-flasks were collected and centrifuged at 1000 rpm for 8 minutes. Approximately 40 mL DMEM was used to resuspend the cells and a small aliquot was taken for counting.

During the anti-CD90 incubation step, MACS LS column and pre-filter was set up. Each column had a maximum capacity of $1.3 \times 108$ cells. The column and pre-filter were rinsed with about 8 mL DMEM.

Cells were diluted to about 5 mL. Five hundred (500) μL increments of cell suspension were added to the pre-filter and column. Once all cells were added the column was rinsed with approximately 9 mL of DMEM. All flow through was collected together in a sterile 50mL conical tube. The flow through volume was brought up to about 25 mL and cells were counted. Myeloma cells (fusion partner) were added to lymphocytes in a 1:1 ratio. Volume of myeloma suspension= (total # of lymphocytes)/[myeloma/mL].

The mixed cell suspension was centrifuged at 1200 rpm (500×g) for 8 minutes to pellet the cells. The supernatant was discarded and cells resuspended cells in 5 mL Pronase enzyme at 0.7 mg/mL. Cells were contacted with pronase enzyme for precisely 90 seconds. At this point 7 mL of sterile PBS was added to neutralize the enzyme and electro-cell fusion buffer was added to bring the volume up to approximately 30 mL.

Cells were pipetted through a 40 μm cell strainer. The strainer was rinsed with fusion buffer to bring volume up to 50 mL and the mixture was centrifuged at 1200 rpm (500×g) for 8 minutes to pellet cells. The supernatant was discarded and cells were re-suspended in 45 mL fusion buffer. Cells were counted and then resuspended at $2 \times 10^6$ total cells/mL in fusion buffer. Volume of fusion buffer=(total cell #)/($2 \times 10^6$ cell/mL). The fusion slide chamber was sterilized in alcohol for at least 15 minutes before use. The electro-cell fusion chamber was washed with 2 mL fusion buffer three times. Electrodes were attached to the dish and taped down. Electrofusion was performed 2 mL at a time. Fused cells were transferred to tube with pre-warmed fusion media. BTX ECM2001 settings: 50 volt AC pre-fusion hold for 50 seconds. Single pulse at 3000 volts for 30 μsec. Five second post fusion hold time.

Cells were allowed to recover in 37° C. incubator for 30 to 60 minutes and were centrifuged at 1000 rpm for 8 minutes. The supernatant was discarded and cells were resuspended in HA media and plated out at approximately 200 μL/well into 96 well plates. Plating concentration was less than 2×10⁶ cells/plate. Hybridoma cells were allowed to grow until confluent.

ELISA was performed to test hybridoma cell supernatants to determine which wells/clones were producing the desired antibody. Several 96 well plates were coated with 100 μl/well of DKKL-1 isoform 2 or isoform 3 purified protein diluted to 1-2 μg/mL in coating buffer. Plates were coated overnight at 4° C. or for 2 hours at 37° C. Coated plates were washed 3× with wash buffer and 250 μL/well of blocking buffer was added to all wells. Plates were incubated for 1 hour at room temperature on a plate shaker set to medium low. While the antigen-coated plates were blocking, the cell supernatants were diluted 1:1 (50 μL: 50 μL). Plates were washed after the blocking buffer incubation (wash 3×). Diluted hybridoma supernatants were added to the blocked plates and positive and negative controls in duplicate were added to the plates using a predetermined dilution. Plates were incubated for 1 hour at room temperature on a plate shaker set to medium low. After the incubation step, plates were washed 3× and 100 μl/well of the appropriate conjugate diluted (1:5000-1:20,000) in assay buffer was added to each well. Plates were incubated for 1 hour at room temperature on a plate shaker set to medium low. After the secondary antibody incubation, plates were washed 3× and 100 μl/well of substrates was added to each well. Plates were incubated for 15 to 45 minutes at room temperature, depending on rate of reaction, and 100 μL/well of the stop solution was added to each well when the Reference Standard had reached an optimum reactivity level. Alkaline Phosphatase assays were read before stopping to determine the reactivity. AP reactive plates were read at 405 nm-490 nm.

After clones were screened by ELISA from 96 well culture plates, those that were positive were subcloned into 1 cell or 5 cells per well concentration in another 96 well culture plate. Cells were allowed to grow until 70% confluent. ELISA was performed as described and subclones including A8.1 and A8.7 were expanded to 48 or 24 well tissue culture plates in Rich Media. Cells were allowed to grow until significant cell growth was obvious upon visual inspection. The normal period of healthy growth in 48 well culture was 2 to 4 days. At this point clones were expanded to T25 flasks in 10 mL Rich media. Cells were allowed to grow to near confluency, or if suspensory, until the media just started to develop an orange tint. Three vials of cells were frozen using standard cell freezing medium from T25 flask at this point by centrifuging contents of flask at 1000 rpm for 7 minutes. At this point hybridoma supernatant was collected and antigen binding was assessed by immunoprecipitation of condition medium of Rat1 stable cell lines expressing either DKKL-1 isoform 1, isoform 2 or isoform 3 to characterize isoform binding specificity.

Example 12

Immunoprecipitation of Isoforms Using Purified mAB

Rat1 stable cell lines expressing either DKKL-1 isoform 1, isoform 2 or isoform 3 were grown in T225 flask until 90% confluent. DKKL-1 isoform-containing culture media (condition media) was collected and could be stored at 4° C. for 2 weeks without any significant degradation.

Figure 10:
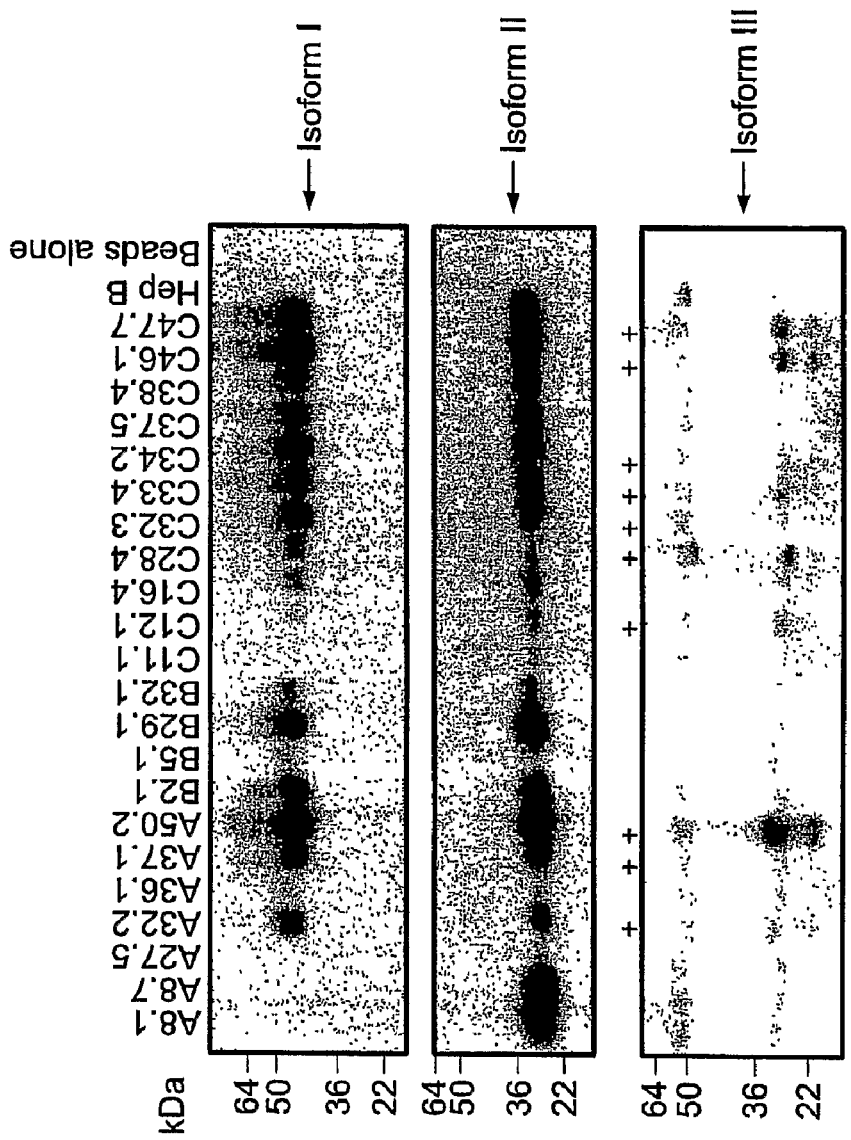
FIG. 10 depicts immunoprecipitation of DKKL-1 splice variants using purified mAbs.

One (1) ml of hybridoma supernatant such as A8.7 was incubated with 50l11 of Protein G slurry in an Eppendorf tube. Mixtures were incubated for 2 hours at 4° C. on a rocking platform or a rotator. Beads were spun down at 10000×g for 30 seconds at 4° C. Supernatants were removed completely and beads were washed 3-5 times with 500 μl of Wash buffer (0.1% NP40 of 1×PBS). Antibody bound protein G beads were incubated with 1 ml of condition media from Rat1 stable cell lines expressing DKKL-1 isoform 1, isoform 2 or isoform 3. Mixtures were incubated for 2 hours at 4° C. on a rocking platform or a rotator. Antigen bound beads were spun down at 10000×g for 30 seconds at 4° C. Supernatants were completely removed and beads were washed 3-5 times with 500 μl of Wash buffer. After the last wash, supernatant was aspirated and 50 μl of 1× Laemmli sample buffer was added to the bead pellet. Mixtures were vortexed and heated to 90-100° C. for 5 minutes. Supernatants were collected and loaded onto the gel. Western blot procedure was performed using anti-V5-HRP conjugated antibody to detect bounded DKKL-1 isoforms, which were V5 tagged at the C-terminus. Isoform specificity was determined for each antibody from the hybridoma supernatants. For example, as set forth in FIG. 10, clones A8.1 and A8.7 were able to immunoprecipitate DKKL-1 isoform 2 but not isoform 1 and isoform 3 from condition media, whereas clone A50.2 immunoprecipitated all 3 isoforms.

Example 13

Cell Proliferation

Figure 6A:
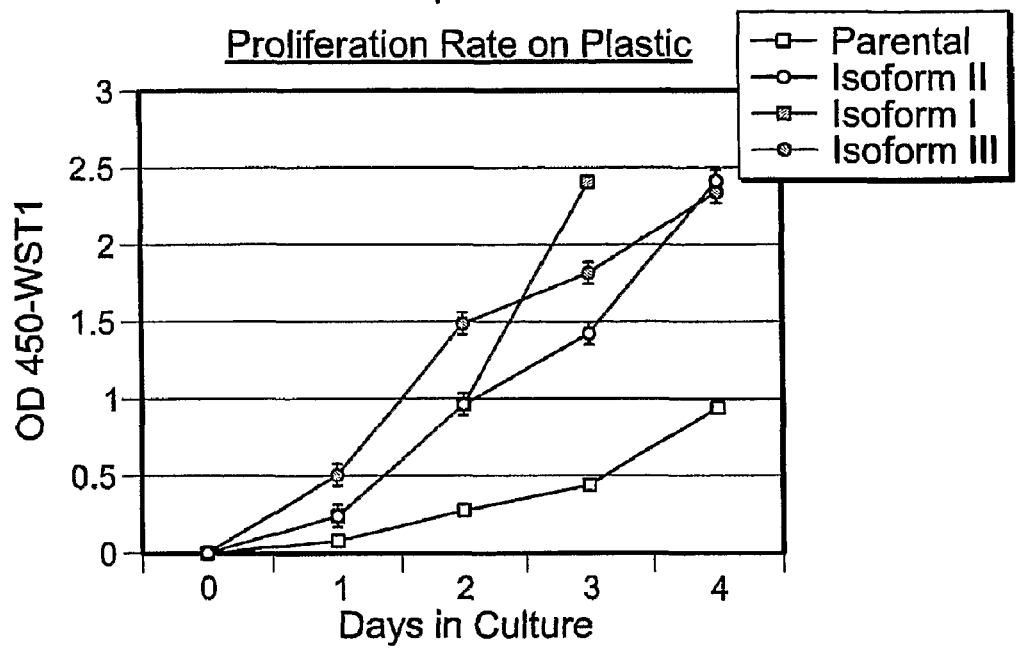
FIG. 6 depicts proliferation of stable cell lines expressing DKKL-1 splice variants.
Figure 6B:
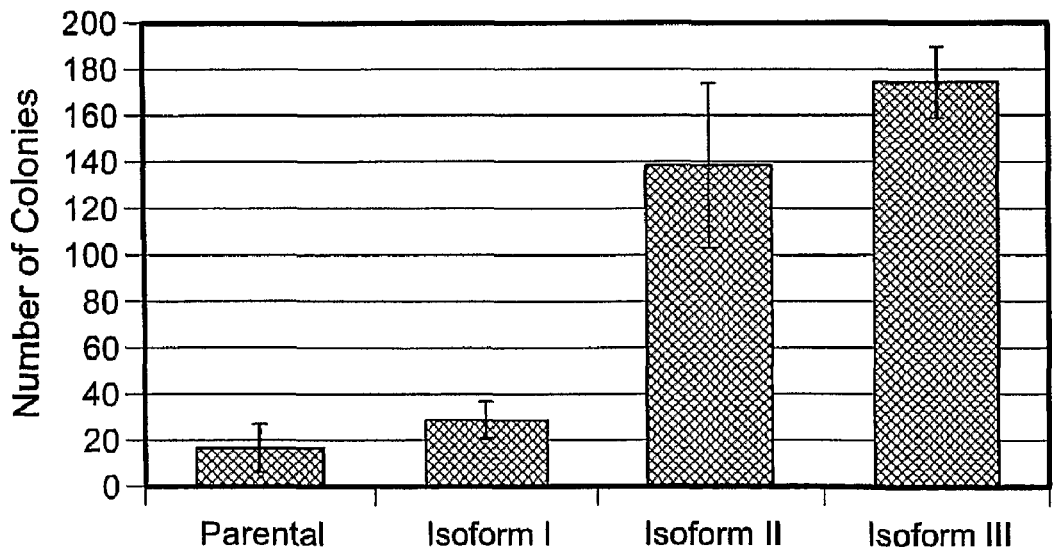

Rat1 cell lines each stably expressing DKKL-1 isoform 1, isoform 2, isoform 3 or pCMV vector alone were grown in DMEM with 10% FBS with 800 ug/ml of G418 selection. One thousand (1000) cells/100 μl of growth media of each of these stable cell lines were seeded into a 96-well plate of quadreplicate samples. Five identical 96-well plates were seeded at the same time for each of the time points (Day0-Day4). The Day0 plate was used for the first time point to measure relative proliferation rate among all stable cell lines. Ten (10) μl/well of WST-1 cell proliferation reagent (Roche Cat# 1644807) was added. Cells were incubated for 2 hrs at 37° C. After the incubation period, the plates were shaken thoroughly on a plate shaker for 1 minute. Absorbance at 420-480 nM was measured using a microplate photometric reader. Plates for Day1, Day2, Day3 and Day4 were measured accordingly using the same WST-1 reagents. Relative proliferation rates of each of these stable cell lines was plotted using average raw absorbance at 450 nM subtracting the background against time (Day0-Day4) as depicted in FIG. 6. Standard deviation was calculated across quadreplicate samples.

Example 14

Tumor Formation in SKID Mice

Rat1 stable cell lines expressing DKKL-1 isoform 1, isoform 2 or isoform 3 were grown to 70-80% confluency in a T150 flask. Cells were washed twice with 1×PBS and resuspended to 10⁷ cells/ml, 10⁶ cells/ml and 10⁵ cells/ml with PBS to three sterile 1.5 ml tubes per cell line. Female NOD.CB17-Prkdc<scid>/J mice, 3-5 weeks of age were obtained from JAX West's M-3 facility (U. C. Davis) and housed 4 per cage in an isolator unit at JAX West's West Sacramento facility.

Figure 7:
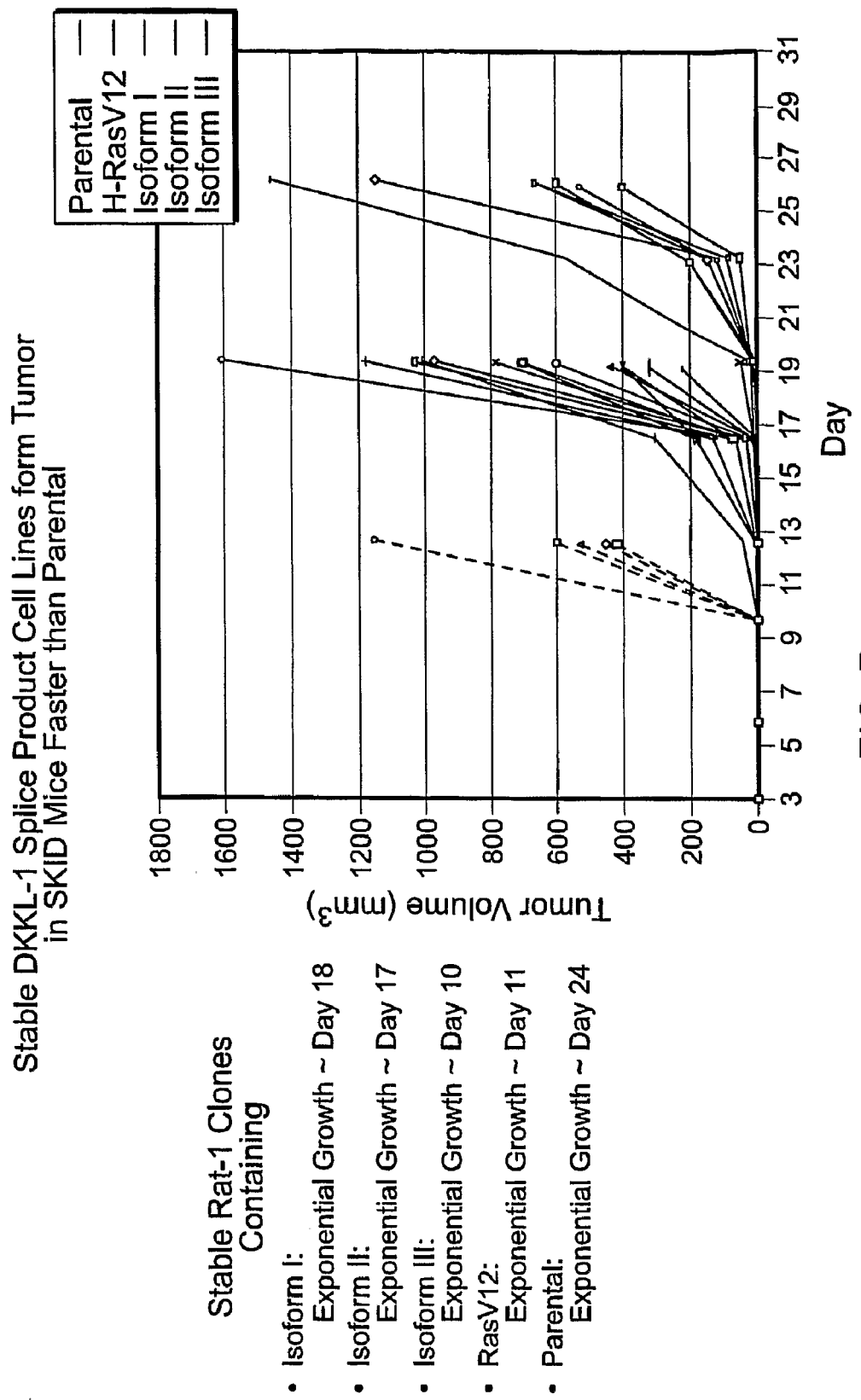
FIG. 7 depicts tumor formation of Rat1 cell lines containing stable DKKL-1 splice products in SKID mice.

Twelve mice were utilized per cell line, which included enough mice for injections of positive control cells (cells expressing the Harvey Ras mutation) and negative control cells (the parental cell line that was not transfected) at the same time. Mice were housed in the isolator unit at all times except when tumor cells were injected, which was performed in the procedure room. On day of injections, mice were moved to the procedure room and placed in the biosafety cabinet. Mice fur is shaved on the ventral thorax. Excess fur was removed using gauze soaked in 70% ethanol, which also serves to disinfect the skin. A 25 gauge needle was used to inject 0.1 ml cell suspension subcutaneously in the thoracic region (2 sites per mouse). After tumor cells were injected, mice were returned to the isolator unit. Animals were housed in the isolator units and observed daily for tumor development and the date at which a tumor appeared was recorded. Once a tumor began to form, tumor growth was measured twice per week using calipers. Mice were restrained using typical scruffing techniques and the tumors were measured in two directions, rostral-caudal and medial-lateral. Once tumors measured 1.5 cm in either direction, tumor tissues were harvested. Animals that did not develop tumors by 4 weeks after injection were euthanized. Measurements were recorded as width×length and volume was calculated using the conversion formula (length×width2)/2. Results are depicted in FIG. 7.

Example 15

β-Catenin Stabilization

Rat1 stable cell lines expressing DKKL-1 isoform 1, isoform 2, isoform 3 or pCMV vector alone were grown to 80% confluency and were harvested for cell fractionation procedures.

Cells were collected and washed with 1×PBS for 3 times. Cell pellets were lysed in 0.2-0.5 ml of Hypotonic lysis buffer for 30 minutes. Cells were then sheared by passing through a 26 5/8 G needle attached to a 1 ml syringe 15 times. Mixtures were spun down at 1500 rpm for 10 minutes to get rid of unbroken cells and nuclei. Once the spin was complete, supernatants (membrane & cytosolic fractions) were transferred to ultracentrifuge tubes and spun at 100,000 g (50,000 rpm)×30 min at 4° C. Once supernatant was finished spinning in the ultracentrifuge, supernatant, which is the cytosolic fraction, was transferred to new eppendorf tubes. The pellet was solubilized using 0.2-0.3 ml RIPA Buffer for 30 minutes on ice and spun down at 15000 rpm for 30 minutes. The supernatant represents the membrane fraction. The protein concentrations of both fractions were determined using the Bradford Assay. Ten (10) μg of protein lysates of the appropriate fractions were loaded on SDS-PAGE gel. Western blot were done using with α-catenin polyclonal antibody to determine the relative cytosolic/membrane levels of β-catenin. β-catenin localized to both the plasma membrane and cytosolic compartments of the cell. β-catenin becomes active when it accumulated in the cytosolic compartment through mechanism of blocking protein degradation machinery. By measuring the level of α-catenin in the cytosolic compartment, one can determine if β-catenin is activated by upstream signaling.

With cell lines that did not have high levels of cyctosolic β-catenin, such as isoform 1 or isoform 2, one could treat the cells with Wnt3a conditioned medium to induce cytosolic β-catenin. Wnt3a conditioned medium was harvested from LMTK stable cell lines expressing Wnt3a from ATCC. Cells were grown to 90% confluency in a T225 flask. Growth media of the cells were collected and were used as conditioned media. Rat1 cells expressing DKKL-1 isoform 1, isoform 2, or isoform 3 were grown in 6-well dishes. When they reached 80% confluency, 2 mls of Wnt3a conditioned medium was added onto the cells for 3 hours and cells were collected for cytosolic fractionation procedure. Cytosolic fractions were loaded on SDS-PAGE gel for western analysis using β-catenin polyclonal antibody.

Figure 8:
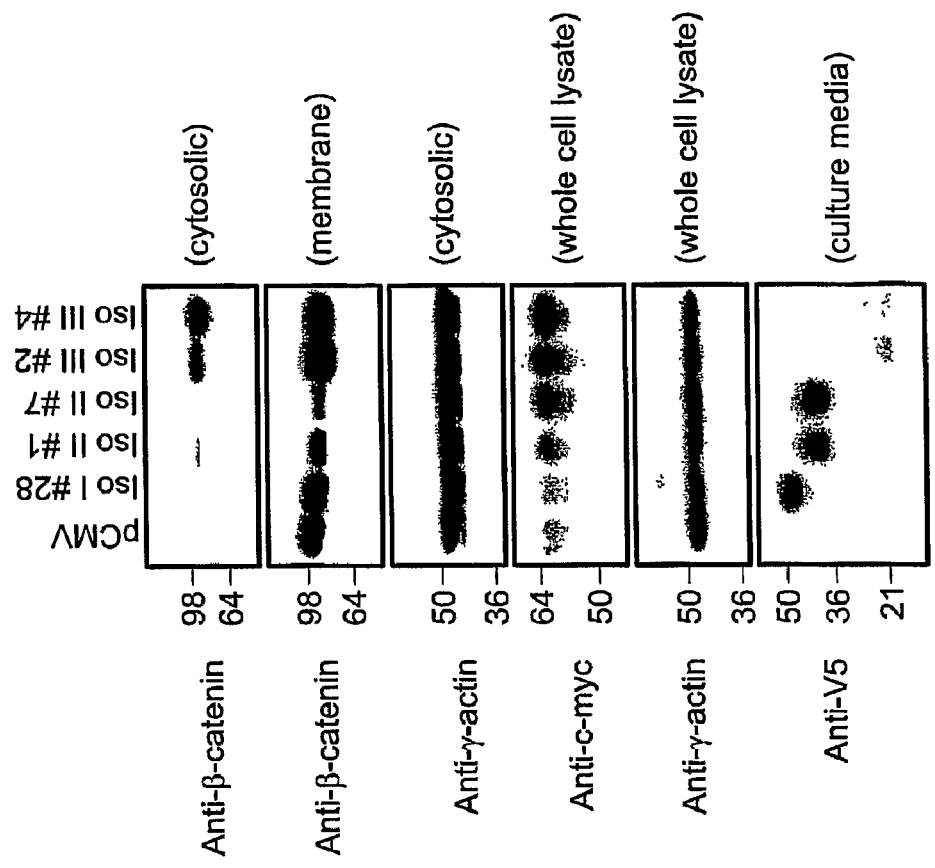
FIG. 8 depicts activation of β-catenin signaling in DKKL-1 splice product expressing stable cell lines
Figure 9:
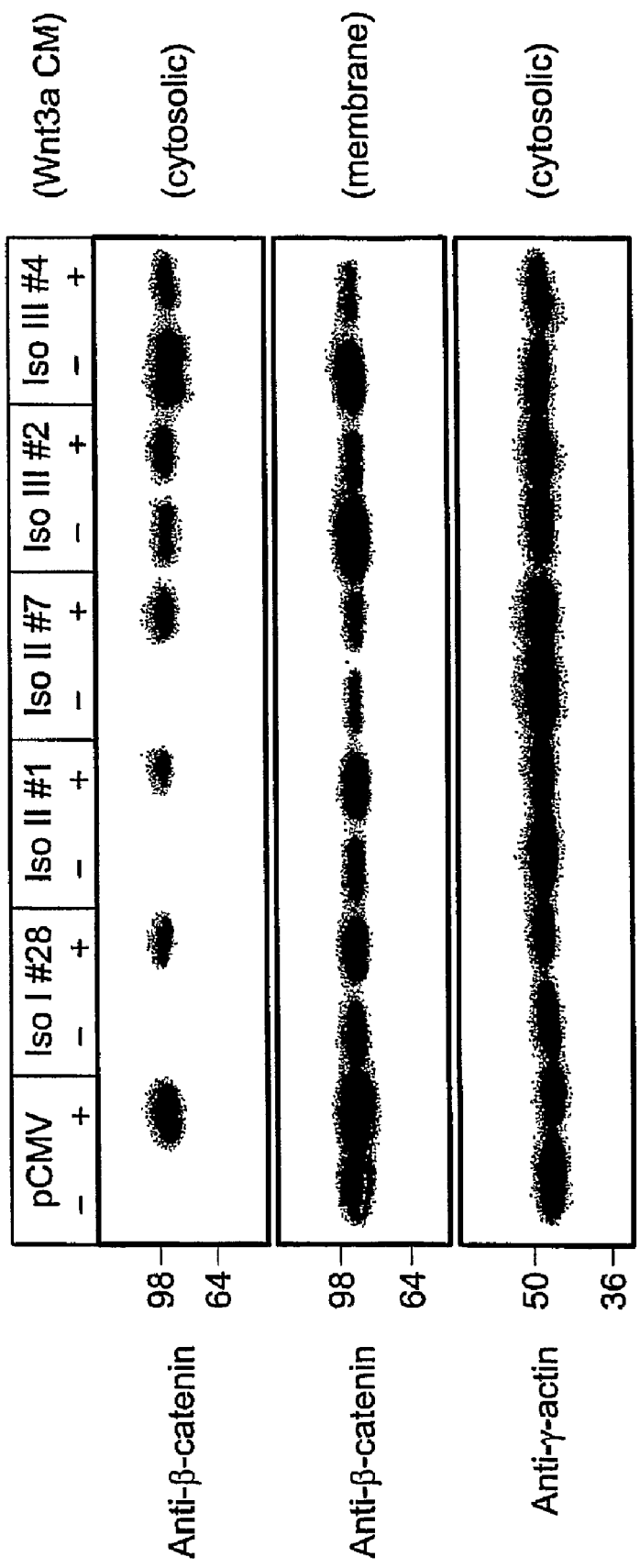
FIG. 9 depicts β-catenin stabilization in DKKL-1 splice product expressing stable cell lines.

Activation of β-catenin signaling is depicted in FIG. 8. β-catenin stabilization is depicted in FIG. 9.

Example 16

Soft Agar Colony Formation

Base agar was prepared using 1% agarose (DNA grade) solution in sterile water. A 1% agarose solution was heated in microwave oven until agarose was melted. The solution was cooled to 40° C. in waterbath. 2×DMEM+20% FBS was prepared and warmed at 40° C. in waterbath. Both media and agarose solution was incubated for at least 1 hour for temperature to equilibrate. Equal volumes of the two solutions were mixed to give 0.5% Agar+1×DMEM+10% FBS. Two (2) mls of mixture were added per well in 6-well dishes and allowed to set. The plates could be stored at 4° C. for up to one week. Top agar was prepared by melting 0.7% agarose in microwave oven and was cooled to 40° C. in waterbath. 2×DMEM+20% FCS was also warmed to 40° C. Rat1 stable cell lines expressing either DKKL-1 isoform 1, isoform 2 or isoform 3 and Rat1 stable cell lines expressing RasV12 or pCMV vector alone were trypsinized and counted. Sixty thousand (60,000) cells were diluted in 2.25 ml of 2×DMEM+20% FCS. 2.25 mls 0.7% Agar were added to the 60,000 cells and 1.5 ml to each triplicate well. Two (2) ml of DMEM-10% FBS was overlayed on top of the agar and was changed every three days until Day 14 when colonies were visible by eye. Agar plates were stained with 0.005% crystal violet at 37° C. for 2 hours and destained with 1×PBS 5 to 6 time until colonies are stained purple and agar color became faded. Colonies were counted by eye on a lightbox and an average of the counts was scored with standard deviation.

Example 17

Immunohistochemistry for DKKL-1 Isoforms in Cancer Cell Lines

NCI-H28, NCI-H522, NCI-H526, A549, NCI-H460 lung cancer cell lines, C33A cervical cancer cell line, PC3 prostate cancer cell line, HT-29, SW620 colon cancer cell lines and MDA-MB-435 breast cancer cell lines, or transfected 293T cells expressing DKKL-1 isoform 1, isoform 2 or isoform 3 were grown in T225 flasks to the density of approximately $2 \times 10^7$/ml for each cell pellet. Cell pellets were fixed in 10% NB Formalin for 12-24 hours and formalin was then replaced with 70% ethanol. Fixed cell pellets were processed on tissue processor and embedded in paraffin. A different fixation method was also employed by treating the cell pellet with 3 ml of OCT and snap frozen in dry ice. The frozen OCT embedded pellets were reembedded in a cryomold labeled appropriately and stored frozen.

Cell pellets and Tissue sections were deparaffinized and hydrated to water. Antigen retrieval was performed in the Decloaker (Biocare, Walnut Creek, Calif.) for 5 minutes using Reveal (Biocare) diluted 1:10 at 201b pressure. Immunohistochemistry procedures were performed on the DAKO Autostainer Plus (DAKO, Carpenteria, Calif.). Endogenous biotin was blocked using Avidin Biotin Blocking solutions (Vector Labs, Burlingame, Calif.) followed by endogenous peroxidase quenching with DAKO Peroxidase block (DAKO). Endogenous immunoglobulins were blocked using the antibody diluent (Ventana, Tucson, Ariz.) for 30 minutes followed by a 30-minute incubation in the primary antibodies. A mouse monoclonal anti-human DKKL-1-isoform 1 antibody (R & D systems), mouse monoclonal anti-DKKL-1 isoform 2 antibody (A8.7), a mouse monoclonal anti-DKKL-1 pan isoforms antibody (A49.3), a rabbit polyclonal anti-DKKL-1 pan isoforms antibody (379-3) and IgG Prebleed control (Chiron, Emeryville, Calif.) were used at 2.5 ug/ml. A biotinylated AffiniPure F(ab')2 fragment goat anti-rabbit or anti-mouse IgG F(ab')2 fragment specific secondary antibody (Jackson ImmunoResearch, West Grove, Calif.) at 2.5 μg/ml followed by Vectastain ABC Elite (Vector Labs) was used for detection. Chromogenic colorization was performed using Stable DAB (Invitrogen, Carlsbad, Calif.). Mayer's Hematoxylin was used as a counter stain and sections were dehydrated in graded alcohols, cleared in xylene and coverslipped using a synthetic mounting media With respect to DKKL-1 isoform 1, the positive control 293T+DKKL1-I transfectant cell pellet was positive when stained with anti-human Soggy-1 Mouse IgG1, as expected, whereas all of the other cell lines tested were negative. For DKKL-1 isoform 2, using monoclonal antibody A8.7, cell lines that were positive by Western blot for DKKL-1 isoform 2 were also immunoreactive by IHC. The two cell lines found to be negative by Western blot (PC3 and SW620) stained negative to rare by IHC as well. See Tables 5 & 6, below:

TABLE 5

| Specimens | DKKL1-IsoI Soggy-1 | Mouse IgG$_{1k}$ |
|---|---|---|
| P05-124p 293T cells only | 0 | — |
| P05-504p 293T + DKKL1 vector | 0 | — |
| P05-593p 293T + DKKL1-I | 3 + Cy | — |
| P05-1068p PC3 | 0 | — |
| P05-1060p A549 | 0 | — |
| P05-1062p MDA-435 | 0 | — |
| P05-1063p NCI-H460 | 0 | — |
| P05-1061p C33A-CMCC | 0 | — |
| P05-1066P C33A-SAGRES | 0 | — |
| P05-1064P NCI-HT29 | 0 | — |
| P05-1069p SW620 | 0 | — |
| P05-1260p NCI-H526 | 0 | — |
| P05-1273p NCI-H522 | 0 | — |
| P05-1274p NCI-H28 | 0 | — |

TABLE 6

| Specimens | DKKL1-ISO II_A8.7 | MOUSE IGG$_{2B}$ |
|---|---|---|
| P05-124p 293T cells only | 0 | — |
| P05-504p 293T + vector | 0 | — |
| P05-506p 293T + DKKL1-II | 3+, Cy (M), scattered | — |
| P05-1061p C33A-CMCC | 3+, Cy (M), scattered | — |
| P05-1066P C33A-SAGRES | 3-4+, Cy, scattered | — |
| P05-1062P MDA-435 | 2+, Cy, ~100%+ | — |
| P05-1064p NCI-HT29 | 3+, Cy, 75-80%+ | — |
| P05-1060p A549 | 2+, Cy, ~100% | — |
| P05-1063p NCI-H460 | 1-3+, Cy, 90% | — |
| P05-1260p NCI-H526 | 2-3+, Cy, 90% | — |
| P05-1273p NCI-H522 | 2-3+, Cy, ~100% | — |
| P05-1274p NCI-H28 | 2-3+, Cy diffuse | — |
| P05-1068p PC3 | <1%+ | — |
| P05-1069p SW620 | <1%+ | — |

Staining intensity is set forth as 4>3>2>1>0 with 0="no staining" or "–". The percentage set forth represents the percentage of cells/visual field that stained at intensity from 1-4. "Scattered" represents <50%. (M)=membrane staining; Cy=cytoplasmic staining.

Example 18 siRNA Effects on Proliferation and Protein Levels

C33A cervical cancer cell line, A2780 ovarian cancer cell line and NCI-H522 cancer cell lines express DKKL-1 both at the protein and mRNA level. OVCAR8 ovarian cancer cell line does not express DKKL-1 (both protein and mRNA-CT:>35).

Cells (C33A cervical cancer cell line, A2780 ovarian cancer cell line, NCI-H522 cancer cell line, OVCAR8 ovarian cancer cell line and Rat1 cell line) were seeded at 10000 cells/well in a 48 well-plate in 0.5 ml of medium the day before transfection. Plates were incubated at 37° C. O/N. The next day the medium was removed and 0.5 ml of complete medium was added. In an Eppendorf tube, 100 μl of OptiMem was added. Diluted siRNA (20 μM stock) at 100 nM and diluted lipid (0.5 mM stock) at 3.75 μM were mixed together to form the complex and added to the cells dropwise. The cells with the siRNA were incubated from 4 h to overnight at 37° C. and replaced with complete media. Cells were harvested cells at 24-72 hours to monitor RNA/protein levels. Proliferation was measured using Promega Cell titre Glow assay at 0, 24, 48 and 72 hrs. siRNA used were:Si379-2: AAAGAG-GAGAACCAGGAGCAC SEQ ID NO:13; Si379-8: GGTG-GCCTTCTGGATCATTAA SEQ ID NO:14; and Si379-10: GACCCACAAGGACGTCCTAGA SEQ ID NO:15. Eg5 siRNA: AACTGAAGACCTGAAGACAAT (SEQ ID NO:16) was used as positive control for proliferation and Eg5S (scrambled sequenced): AATAACAGAAGTCCA-GAAGTC (SEQ ID NO:17) was used as negative control.

Figure 11:
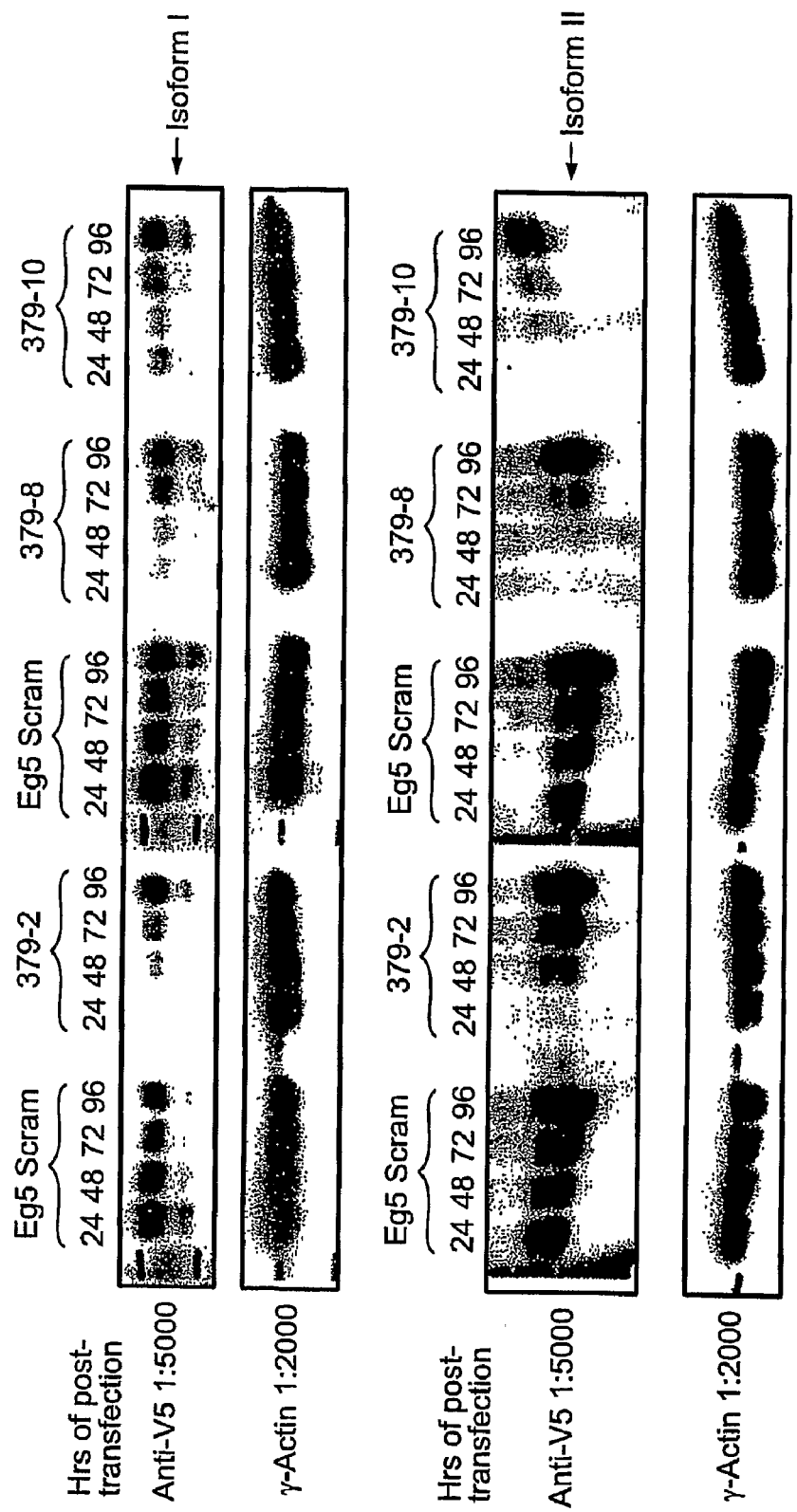
FIG. 11 depicts protein knock down of DKKL-1 splice variants with siRNA in Rat1 stable cell lines.
Figure 12:
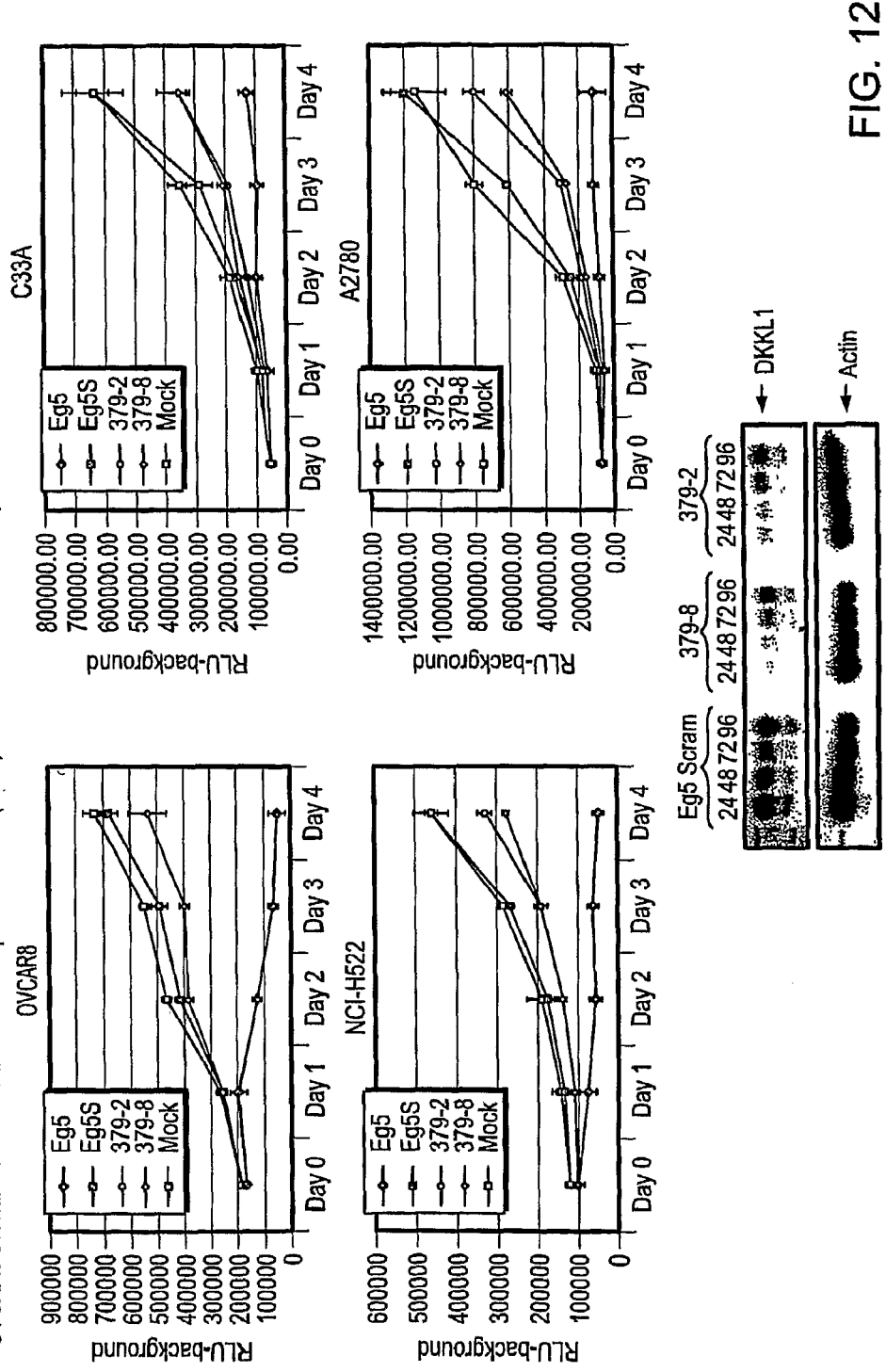
FIG. 12 depicts antiporliferative effects of siRNA on the C33A cervical cancer cell line, the A2780 ovarian cancer cell line and the NCI-H522 cancer cell line.

FIG. 11 depicts knockdown of DKKL-1 splice variant protein in Rat1 cells. FIG. 12 depicts antiporliferative effects of siRNA on the C33A cervical cancer cell line, the A2780 ovarian cancer cell line and the NCI-H522 cancer cell line Example 19

Sequences

DKKL-1-isoform 1: nucleotide sequence
(SEQ ID NO: 1)
atgggagaagcctccccacctgccccgcaaggcggcatctgctggtcct gctgctgctcctctctaccctggtgatccctccactgcagctcctatcc atgatgctgacgcccaagagagctccttgggtctcacaggcctccagagc ctactccaaggcttcagccgacttttcctgaaaggtaacctgcttcggggg catagacagcttattctctgcccccatggacttccggggcctccctggga actaccacaaagaggagaaccaggagcaccagctggggaacaacaccctc tccagccacctccagatcgacaagatgaccgacaacaagacaggagaggt gctgatctccgagaatgtggtggcatccattcaaccagcggaggggagct tcgagggtgatttgaaggtacccaggatggaggagaaggaggccctggta cccatccagaaggccacggacagcttccacacagaactccatccccgggt ggccttctggatcattaagctgccacggcggaggtccaccaggatgccc tggagggcggccactggctcagcgagaagcgacaccgcctgcaggccatc cgggatggactccgcaaggggacccacaaggacgtcctagaagagggggac cgagagctcctcccactccaggctgtccccccgaaagacccacttactgt

```
acatcctcaggccctctcggcagctgtag
```

DKKL-1-isoform 1: protein sequence (SEQ ID NO: 2)
```
MGEASPPAPARRHLLVLLLLLSTLVIPSTAAPIHDADAQESSLGLTGLQS

LLQGFSRLFLKGNLLRGIDSLFSAPMDFRGLPGNYHKEENQEHQLGNNTL

SSHLQIDKMTDNKTGEVLISENVVASIQPAEGSFEGDLKVPRMEEKEALV

PIQKATDSFHTELHPRVAFWIIKLPRRRSHQDALEGGHWLSEKRHRLQAI

RDGLRKGTHKDVLEEGTESSSHSRLSPRKTHLLYILRPSRQL
```

DKKL-1-isoform 2: nucleotide sequence (SEQ ID NO: 3)
```
atgggagaagcctccccacctgccccgcaaggcggcatctgctggtcct gctgctgctcctctctaccctggtgatcccctccgctgcagctcctatcc atgatgctgacgcccaagagagctccttgggtctcacaggcctccagagc ctactccaaggcttcagccgacttttcctgaaaggtaacctgcttcgggg catagacagcttattctctgcccccatggacttccggggcctccctggga actaccacaaagaggagaaccaggagcaccagctggggaacaacaccctc tccagccacctccagatcgacaaggtacccaggatggaggagaaggaggc cctggtacccatccagaaggccacggacagcttccacacagaactccatc cccgggtggccttctggatcattaagctgccacggcggaggtcccaccag gatgccctgagggcggccactggctcagcgagaagcgacaccgcctgca ggccatccgggatggactccgcaaggggacccacaaggacgtcctagaag aggagaccgagagctcctcccactccaggctgtcccccgaaagacccac ttactgtacatcctcaggccctctcggcagctgtag
```

DKKL-1-isoform 2: protein sequence (SEQ ID NO: 4)
```
MGEASPPAPARRHLLVLLLLLSTLVIPSAAAPIHDADAQESSLGLTGLQS

LLQGFSRLFLKGNLLRGIDSLFSAPMDFRGLPGNYHKEENQEHQLGNNTL

SSHLQIDKVPRMEEKEALVPIQKATDSFHTELHPRVAFWIIKLPRRSHQ

DALEGGHWLSEKRHRLQAIRDGLRKGTHKDVLEEETESSSHSRLSPRKTH

LLYILRPSRQL
```

DKKL-1-isoform 3: nucleotide sequence (SEQ ID NO: 5)
```
atgggagaagcctccccacctgccccgcaaggcggcatctgctggtcct gctgctgctcctctctaccctggtgatcccctccactgcagctcctatcc atgatgctgacgcccaagagagctccttgggtctcacaggcctccagagc ctactccaaggcttcagccgacttttcctgaaagtacccaggatggagga gaaggaggccctggtacccatccagaaggccacggacagcttccacacag aactccatccccgggtggccttctggatcattaagctgccacggcggagg tcccaccaggatgccctggagggcagccactggctcagcgagaagcgaca ccgcctgcaggccatccgggatggactccgcaaggggacccacaaggacg tcctaaaagaggggaccgagagctcctcccactccaggctgtcccccga aagacccacttactgtacatcctcaggccctctcggcagctgtag
```

DKKL-1-isoform 3: protein sequence (SEQ ID NO: 6)
```
MGEASPPAPARRHLLVLLLLLSTLVIPSTAAPIHDADAQESSLGLTGLQS

LLQGFSRLFLKVPRMEEKEALVPIQKATDSFHTELHPRVAFWIIKLPRRR

SHQDALEGSHWLSEKRHRLQAIRDGLRKGTHKDVLKEGTESSSHSRLSPR

KTHLLYILRPSRQL
```

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. A method for detecting one or more cancer cells expressing a Dickkopf-like 1 (DKKL-1) splice product in a sample, the method comprising contacting the sample with an antibody that specifically binds the DKKL-1 splice product, does not specifically bind to wild-type DKKL-1, wherein the antibody is labeled, the label is a radioisotope selected from the group consisting of: $^{18}$F, $^{43}$K, $^{52}$Fe, $^{57}$Co, $^{67}$Cu, $^{67}$Ga, $^{77}$Br, $^{87M}$Sr, $^{86}$Y, $^{90}$Y, $^{99}$MTc, $^{111}$In, $^{123}$I, $^{125}$I, $^{127}$Cs, $^{129}$Cs, $^{131}$I, $^{132}$I, $^{197}$Hg, $^{203}$Pb, $^{206}$Bi and detecting the label in the sample.

2. The method of claim 1 wherein the antibody is a monoclonal antibody.

3. The method of claim 1, wherein the antibody specifically binds to SEQ ID NO. 4.

4. The method of claim 3, wherein the cancer cell is selected from the group consisting of lung, ovary, lymphoid and liver cancer.

5. The method of claim 4, wherein the lung cancer cell is mesothelioma or non-small cell lung cancer.

6. The method of claim 1, wherein the antibody specifically binds to SEQ ID NO. 6.

7. The method of claim 6, wherein the cancer cell is selected from the group consisting of lung, breast or liver cancer.

8. The method of claim 7, wherein the lung cancer cell is mesothelioma or non-small cell lung cancer.

9. The method of claim 7, wherein the breast cancer cell is selected from the group consisting of ductal adenocarcinoma, lobular adenocarcinoma and metastatic adenocarcinoma.

* * * * *

SEQUENCE LISTING

```
<160> NUMBER OF SEQ ID NOS: 44

<210> SEQ ID NO 1
<211> LENGTH: 729
<212> TYPE: DNA
<213> ORGANISM: Homo sapiens

<400> SEQUENCE: 1
atgggagaag cctccccacc tgccccgca aggcggcatc tgctggtcct  gctgctgctc       60
ctctctaccc tggtgatccc ctccactgca gctcctatcc atgatgctga cgcccaagag      120
agctccttgg gtctcacagg cctccagagc ctactccaag gcttcagccg acttttcctg      180
aaaggtaacc tgcttcgggg catagacagc ttattctctg ccccatgga cttccggggc       240 ctccctggga actaccacaa agaggagaac caggagcacc agctggggaa caacaccctc      300
tccagccacc tccagatcga caagatgacc gacaacaaga caggagaggt gctgatctcc      360
gagaatgtgg tggcatccat tcaaccagcg aggggagct cgagggtga tttgaaggta       420 cccaggatgg aggaaggag ggccctggta cccatccaga aggccacgga cagcttccac      480
```

-continued

```
acagaactcc atccccgggt ggccttctgg atcattaagc tgccacggcg gaggtcccac    540
caggatgccc tggagggcgg ccactggctc agcgagaagc gacaccgcct gcaggccatc    600
cgggatggac tccgcaaggg gacccacaag gacgtcctag aagagggac  cgagagctcc    660 tcccactcca ggctgtcccc ccgaaagacc cacttactgt acatcctcag gccctctcgg    720
cagctgtag                                                            729
```

<210> SEQ ID NO 2
<211> LENGTH: 242
<212> TYPE: PRT
<213> ORGANISM: Homo sapiens

<400> SEQUENCE: 2

```
Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Thr Ala Ala Pro
            20                  25                  30

Ile His Asp Ala Asp Ala Gln Glu Ser Ser Leu Gly Leu Thr Gly Leu
        35                  40                  45

Gln Ser Leu Leu Gln Gly Phe Ser Arg Leu Phe Leu Lys Gly Asn Leu
    50                  55                  60

Leu Arg Gly Ile Asp Ser Leu Phe Ser Ala Pro Met Asp Phe Arg Gly
65                  70                  75                  80

Leu Pro Gly Asn Tyr His Lys Glu Glu Asn Gln Glu His Gln Leu Gly
                85                  90                  95

Asn Asn Thr Leu Ser Ser His Leu Gln Ile Asp Lys Met Thr Asp Asn
            100                 105                 110

Lys Thr Gly Glu Val Leu Ile Ser Glu Asn Val Val Ala Ser Ile Gln
        115                 120                 125

Pro Ala Glu Gly Ser Phe Glu Gly Asp Leu Lys Val Pro Arg Met Glu
    130                 135                 140

Glu Lys Glu Ala Leu Val Pro Ile Gln Lys Ala Thr Asp Ser Phe His
145                 150                 155                 160

Thr Glu Leu His Pro Arg Val Ala Phe Trp Ile Ile Lys Leu Pro Arg
                165                 170                 175

Arg Arg Ser His Gln Asp Ala Leu Glu Gly Gly His Trp Leu Ser Glu
            180                 185                 190

Lys Arg His Arg Leu Gln Ala Ile Arg Asp Gly Leu Arg Lys Gly Thr
        195                 200                 205

His Lys Asp Val Leu Glu Glu Gly Thr Glu Ser Ser His Ser Arg
        210                 215                 220

Leu Ser Pro Arg Lys Thr His Leu Leu Tyr Ile Leu Arg Pro Ser Arg
225                 230                 235                 240

Gln Leu
```

<210> SEQ ID NO 3
<211> LENGTH: 636
<212> TYPE: DNA
<213> ORGANISM: Homo sapiens

<400> SEQUENCE: 3

```
atgggagaag cctccccacc tgccccgca  aggcggcatc tgctggtcct gctgctgctc     60
ctctctaccc tggtgatccc ctccgctgca gctcctatcc atgatgctga cgcccaagag    120
agctccttgg gtctcacagg cctccagagc ctactccaag gcttcagccg acttttcctg    180
```

-continued

```
aaaggtaacc tgcttcgggg catagacagc ttattctctg ccccatgga cttccggggc      240 ctccctggga actaccacaa agaggagaac caggagcacc agctgggaa caacaccctc       300 tccagccacc tccagatcga caaggtaccc aggatggagg agaaggaggc cctggtaccc      360
atccagaagg ccacggacag cttccacaca gaactccatc cccgggtggc cttctggatc      420
attaagctgc cacggcggag gtcccaccag gatgccctgg agggcggcca ctggctcagc      480
gagaagcgac accgcctgca ggccatccgg gatggactcc gcaaggggac ccacaaggac      540
gtcctagaag aggagaccga gagctcctcc cactccaggc tgtccccccg aaagacccac      600
ttactgtaca tcctcaggcc ctctcggcag ctgtag                                636
```

<210> SEQ ID NO 4
<211> LENGTH: 211
<212> TYPE: PRT
<213> ORGANISM: Homo sapiens

<400> SEQUENCE: 4

```
Met Gly Glu Ala Ser Pro Pro Ala Pro Arg Arg His Leu Leu Val
1               5                   10                  15

Leu Leu Leu Leu Ser Thr Leu Val Ile Pro Ser Ala Ala Ala Pro
            20                  25                  30

Ile His Asp Ala Asp Ala Gln Glu Ser Ser Leu Gly Leu Thr Gly Leu
            35                  40                  45

Gln Ser Leu Leu Gln Gly Phe Ser Arg Leu Phe Leu Lys Gly Asn Leu
    50                  55                  60

Leu Arg Gly Ile Asp Ser Leu Phe Ser Ala Pro Met Asp Phe Arg Gly
65                  70                  75                  80

Leu Pro Gly Asn Tyr His Lys Glu Glu Asn Gln Glu His Gln Leu Gly
                85                  90                  95

Asn Asn Thr Leu Ser Ser His Leu Gln Ile Asp Lys Val Pro Arg Met
            100                 105                 110

Glu Glu Lys Glu Ala Leu Val Pro Ile Gln Lys Ala Thr Asp Ser Phe
        115                 120                 125

His Thr Glu Leu His Pro Arg Val Ala Phe Trp Ile Ile Lys Leu Pro
    130                 135                 140

Arg Arg Arg Ser His Gln Asp Ala Leu Glu Gly Gly His Trp Leu Ser
145                 150                 155                 160

Glu Lys Arg His Arg Leu Gln Ala Ile Arg Asp Gly Leu Arg Lys Gly
                165                 170                 175

Thr His Lys Asp Val Leu Glu Glu Thr Glu Ser Ser Ser His Ser
            180                 185                 190

Arg Leu Ser Pro Arg Lys Thr His Leu Leu Tyr Ile Leu Arg Pro Ser
        195                 200                 205

Arg Gln Leu
    210
```

<210> SEQ ID NO 5
<211> LENGTH: 495
<212> TYPE: DNA
<213> ORGANISM: Homo sapiens

<400> SEQUENCE: 5

```
atgggagaag cctccccacc tgccccgca aggcggcatc tgctggtcct gctgctgctc      60
ctctctaccc tggtgatccc ctccactgca gctcctatcc atgatgctga cgcccaagag      120
agctccttgg gtctcacagg cctccagagc ctactccaag gcttcagccg acttttcctg      180
```

-continued

```
aaagtaccca ggatggagga gaaggaggcc ctggtaccca tccagaaggc cacggacagc    240
ttccacacag aactccatcc ccgggtggcc ttctggatca ttaagctgcc acggcggagg    300
tcccaccagg atgccctgga gggcagccac tggctcagcg agaagcgaca ccgcctgcag    360
gccatccggg atggactccg caaggggacc cacaaggacg tcctaaaaga ggggaccgag    420
agctcctccc actccaggct gtccccccga aagacccact tactgtacat cctcaggccc    480
tctcggcagc tgtag                                                     495
```

<210> SEQ ID NO 6
<211> LENGTH: 164
<212> TYPE: PRT
<213> ORGANISM: Homo sapiens

<400> SEQUENCE: 6

Met Gly Glu Ala Ser Pro Pro Ala Pro Ala Arg Arg His Leu Leu Val
1               5                   10                  15

Leu Leu Leu Leu Ser Thr Leu Val Ile Pro Ser Thr Ala Ala Pro
            20                  25                  30

Ile His Asp Ala Asp Ala Gln Glu Ser Ser Leu Gly Leu Thr Gly Leu
        35                  40                  45

Gln Ser Leu Leu Gln Gly Phe Ser Arg Leu Phe Leu Lys Val Pro Arg
    50                  55                  60

Met Glu Glu Lys Glu Ala Leu Val Pro Ile Gln Lys Ala Thr Asp Ser
65                  70                  75                  80

Phe His Thr Glu Leu His Pro Arg Val Ala Phe Trp Ile Ile Lys Leu
                85                  90                  95

Pro Arg Arg Arg Ser His Gln Asp Ala Leu Glu Gly Ser His Trp Leu
            100                 105                 110

Ser Glu Lys Arg His Arg Leu Gln Ala Ile Arg Asp Gly Leu Arg Lys
        115                 120                 125

Gly Thr His Lys Asp Val Leu Lys Glu Gly Thr Glu Ser Ser Ser His
    130                 135                 140

Ser Arg Leu Ser Pro Arg Lys Thr His Leu Leu Tyr Ile Leu Arg Pro
145                 150                 155                 160

Ser Arg Gln Leu

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7

```
gcctccagag cctactccaa                                                 20
```

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8

```
gggcagagaa taagctgtct atgc                                            24
```

<210> SEQ ID NO 9
<211> LENGTH: 15
<212> TYPE: DNA

```
<213> ORGANISM: Artificial Sequence
<220> FEATURE:
<223> OTHER INFORMATION: Probe sequence

<400> SEQUENCE: 9 agccgactttt tcctg                                                        15

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gcctccagag cctactccaa                                                    20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ggtaccaggg cctccttctc                                                    20

<210> SEQ ID NO 12
<211> LENGTH: 18
<212> TYPE: DNA
<213> ORGANISM: Artificial Sequence
<220> FEATURE:
<223> OTHER INFORMATION: Probe sequence

<400> SEQUENCE: 12
tgaaagtacc caggatgg                                                      18

<210> SEQ ID NO 13
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 13
aaagaggaga accaggagca c                                                  21

<210> SEQ ID NO 14
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 14
ggtggccttc tggatcatta a                                                  21

<210> SEQ ID NO 15
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 15
gacccacaag gacgtcctag a                                                  21
```

<210> SEQ ID NO 16
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 16
aactgaagac ctgaagacaa t                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 17
aataacagaa gtccagaagt c                                              21

<210> SEQ ID NO 18
<211> LENGTH: 853
<212> TYPE: DNA
<213> ORGANISM: Homo sapiens

<400> SEQUENCE: 18
gggcgggact ccgaaacgag ggccgcaatc agagaacacc gccaggactt ccaggacttg     60
gtctcccagg actgaggtca actgacgggg gcgtggtctg actgtgtggg cgtggccagg    120
gaatgaactc acggctctgg cttaaggggt gtggtgaacg aaggatgggg cgtggctctg    180
tcaccaaggg cgtggtcatg gagtagaggc ccgggctcct gggtgaggcc ggcaagtttg    240
gagcgtggtc agacaatagg ggcgtggcta cggctcgcgg agcgcaacca acgctctaga    300
ccagacctgg gctcgagacc ataactgttt ggctttaaca gtacgtgggc ggccggaatc    360
cgggagtccg gtgacccggg ctgtggtcta gcataaaggc ggagcccaga agaaggggcg    420
gggtatggga gaaggtgagg attgagatct ggtggtgaac gtgggcgaaa gtgaggaaaa    480
gaccattgga tgaggccggg tgctgtggct tacgcctgca atcccaacac tttgggaggc    540
ccaggtgggc ggatcgcttg agatcaggag ttcgagacca gcctgggcaa tatgtcgaaa    600
ccctgtctct acaaaaaata caaaaattag ccgggcgtgg aggcgcgcgc ctgtggtccc    660
agctacttcg gggggctgag gtgggagaat cacctgagcc ggggaggtc gaggctgcag    720 tgagccgtga ttgtgccact gtactccagc ctggactaca gagtctcggt ctcaaaaaaa    780 aaaaaaaaa agcatatgag acagaaccca gaagagccag acctgggaga agacggggcc    840
tggcaaggtg gag                                                      853

<210> SEQ ID NO 19
<211> LENGTH: 819
<212> TYPE: DNA
<213> ORGANISM: Homo sapiens

<400> SEQUENCE: 19
atgggagaag cctccccacc tgcccccgca aggcggcatc tgctggtcct gctgctgctc     60
ctctctaccc tggtgatccc ctccgctgca gctcctatcc atgatgctga cgcccaagag    120
agctccttgg gtctcacagg cctccagagc ctactccaag gcttcagccg acttttcctg    180
aaaggtaacc tgcttcgggg catagacagc ttattctctg cccccatgga cttccgggc    240 ctccctggga actaccacaa agaggagaac caggagcacc agctgggaa caacaccctc    300

| | |
|---|---:|
| tccagccacc tccagatcga caagaggacc gacaacaaga caggagaggt gctgatctcc | 360 |
| gagaatgtgg tggcatccat tcaaccagcg gaggggagct tcgagggtga tttgaaggta | 420 |
| cccaggatgg aggagaagga ggccctggta cccatccaga aggccacgga cagcttccac | 480 |
| acagaactcc atcccggt ggccttctgg atcattaagc tgccacggcg gaggtcccac | 540 |
| caggatgccc tggagggcgg ccatggctca gcgagaagcg caccgcctg caggccatcc | 600 |
| gggatggact ccgcaagggg acccacaagg acgtcctaga agaggggacc gagagctcct | 660 |
| cccactccag gctgtccccc cgaaagacc cacttactgt acatcctcag gccctctcgg | 720 |
| cagctgtagg ggtggggacc ggggagcacc tgcctgtagc ccccatcaga ccctgcccca | 780 |
| agcaccatat ggaaataaag ttctttctta catctaaca | 819 |

<210> SEQ ID NO 20
<211> LENGTH: 733
<212> TYPE: DNA
<213> ORGANISM: Homo sapiens

<400> SEQUENCE: 20

| | |
|---|---:|
| caccatggga gaagcctccc cacctgcccc cgcaaggcgg catctgctgg tcctgctgct | 60 |
| gctcctctct accctggtga tcccctccgc tgcagctcct atccatgatg ctgacgccca | 120 |
| agagagctcc ttgggtctca caggcctcca gagcctactc caaggcttca gccgactttt | 180 |
| cctgaaaggt aacctgcttc ggggcataga cagcttattc tctgccccca tggacttccg | 240 |
| gggcctccct gggaactacc acaaagagga gaaccaggag caccagctgg ggaacaacac | 300 |
| cctctccagc cacctccaga tcgacaagat gaccgacaac aagacaggag aggtgctgat | 360 |
| ctccgagaat gtggtggcat ccattcaacc agcggagggg agcttcgagg gtgatttgaa | 420 |
| ggtacccagg atggaggaga aggaggccct ggtacccatc cagaaggcca cggacagctt | 480 |
| ccacacagaa ctccatcccc gggtggcctt ctggatcatt aagctgccac ggcggaggtc | 540 |
| ccaccaggat gccctggagg gcggccatgg ctcagcgaga agcgacaccg cctgcaggcc | 600 |
| atccgggatg gactccgcaa ggggacccac aaggacgtcc tagaagaggg gaccgagagc | 660 |
| tcctcccact ccaggctgtc cccccgaaa gacccactta ctgtacatcc tcaggccctc | 720 |
| tcggcagctg tag | 733 |

<210> SEQ ID NO 21
<211> LENGTH: 733
<212> TYPE: DNA
<213> ORGANISM: Homo sapiens

<400> SEQUENCE: 21

| | |
|---|---:|
| caccatggga gaagcctccc cacctgcccc cgcaaggcgg catctgctgg tcctgctgct | 60 |
| gctcctctct accctggtga tcccctccgc tgcagctcct atccatgatg ctgacgccca | 120 |
| agagagctcc ttgggtctca caggcctcca gagcctactc caaggcttca gccgactttt | 180 |
| cctgaaaggt aacctgcttc ggggcataga cagcttattc tctgccccca tggacttccg | 240 |
| gggcctccct gggaactacc acaaagagga gaaccaggag caccagctgg ggaacaacac | 300 |
| cctctccagc cacctccaga tcgacaagat gaccgacaac aagacaggag aggtgctgat | 360 |
| ctccgagaat gtggtggcat ccattcaacc agcggagggg agcttcgagg gtgatttgaa | 420 |
| ggtacccagg atggaggaga aggaggccct ggtacccatc cagaaggcca cggacagctt | 480 |
| ccacacagaa ctccatcccc gggtggcctt ctggatcatt aagctgccac ggcggaggtc | 540 |
| ccaccaggat gccctggagg gcggccatgg ctcagcgaga agcgacaccg cctgcaggcc | 600 |

| atccgggatg gactccgcaa ggggacccac aaggacgtcc tagaagaggg gaccgagagc | 660 |
| tcctcccact ccaggctgtc cccccgaaa gacccactta ctgtacatcc tcaggccctc | 720 |
| tcggcagctg tag | 733 |

<210> SEQ ID NO 22
<211> LENGTH: 733
<212> TYPE: DNA
<213> ORGANISM: Homo sapiens

<400> SEQUENCE: 22

| caccatggga gaagcctccc cacctgcccc cgcaaggcgg catctgctgg tcctgctgct | 60 |
| gctcctctct accctggtga tcccctccgc tgcagctcct atccatgatg ctgacgccca | 120 |
| agagagctcc ttgggtctca caggcctcca gagcctactc caaggcttca gccgactttt | 180 |
| cctgaaaggt aacctgcttc ggggcataga cagcttattc tctgccccca tggacttccg | 240 |
| gggcctccct gggaactacc acaaagagga gaaccaggag caccagctgg ggaacaacac | 300 |
| cctctccagc cacctccaga tcgacaagat gaccgacaac aagacaggag aggtgctgat | 360 |
| ctccgagaat gtggtggcat ccattcaacc agcggagggg agcttcgagg gtgatttgaa | 420 |
| ggtacccagg atggaggaga aggaggccct ggtacccatc cagaaggcca cggacagctt | 480 |
| ccacacagaa ctccatcccc gggtggcctt ctggatcatt aagctgccac ggcggaggtc | 540 |
| ccaccaggat gccctggagg cggccatgg ctcagcgaga agcgacaccg cctgcaggcc | 600 |
| atccgggatg gactccgcaa ggggacccac aaggacgtcc tagaagaggg gaccgagagc | 660 |
| tcctcccact ccaggctgtc cccccgaaa gacccactta ctgtacatcc tcaggccctc | 720 |
| tcggcagctg tag | 733 |

<210> SEQ ID NO 23
<211> LENGTH: 733
<212> TYPE: DNA
<213> ORGANISM: Homo sapiens

<400> SEQUENCE: 23

| caccatggga gaagcctccc cacctgcccc cgcaaggcgg catctgctgg tcctgctgct | 60 |
| gctcctctct accctggtga tcccctccgc tgcagctcct atccatgatg ctgacgccca | 120 |
| agagagctcc ttgggtctca caggcctcca gagcctactc caaggcttca gccgactttt | 180 |
| cctgaaaggt aacctgcttc ggggcataga cagcttattc tctgccccca tggacttccg | 240 |
| gggcctccct gggaactacc acaaagagga gaaccaggag caccagctgg ggaacaacac | 300 |
| cctctccagc cacctccaga tcgacaagat gaccgacaac aagacaggag aggtgctgat | 360 |
| ctccgagaat gtggtggcat ccattcaacc agcggagggg agcttcgagg gtgatttgaa | 420 |
| ggtacccagg atggaggaga aggaggccct ggtacccatc cagaaggcca cggacagctt | 480 |
| ccacacagaa ctccatcccc gggtggcctt ctggatcatt aagctgccac ggcggaggtc | 540 |
| ccaccaggat gccctggagg cagccatgg ctcagcgaga agcgacaccg cctgcaggcc | 600 |
| atccgggatg gactccgcaa ggggacccac aaggacgtcc tagaagaggg gaccgagagc | 660 |
| tcctcccact ccaggctgtc cccccgaaa gacccactta ctgtacatcc tcaggccctc | 720 |
| tcggcagctg tag | 733 |

<210> SEQ ID NO 24
<211> LENGTH: 733
<212> TYPE: DNA
<213> ORGANISM: Homo sapiens -continued

```
<400> SEQUENCE: 24
caccatggga gaagcctccc cacctgcccc cgcaaggcgg catctgctgg tcctgctgct    60
gctcctctct accctggtga tccctccgc tgcagctcct atccatgatg ctgacgccca    120
agagagctcc ttgggtctca caggcctcca gagcctactc caaggcttca gccgactttt    180
cctgaaaggt aacctgcttc ggggcataga cagcttattc tctgccccca tggacttccg    240
gggcctccct gggaactacc acaaagagga gaaccaggag caccagctgg ggaacaacac    300
cctctccagc cacctccaga tcgacaagat gaccgacaac aagacaggag aggtgctgat    360
ctccgagaat gtggtggcat ccattcaacc agcggagggg agcttcgagg gtgatttgaa    420
ggtacccagg atggaggaga aggaggccct ggtacccatc cagaaggcca cggacagctt    480
ccacacagaa ctccatcccc gggtggcctt ctggatcatt aagctgccac ggcggaggtc    540
ccaccaggat gccctggagg cggccatgg ctcagcgaga agcgacaccg cctgcaggcc    600
atccgggatg gactccgcaa gggacccac aaggacgtcc tagaagaggg gaccgagagc    660
tcctcccact ccaggctgtc cccccgaaa gacccactta ctgtacatcc tcaggccctc    720
tcggcagctg tag                                                      733

<210> SEQ ID NO 25
<211> LENGTH: 640
<212> TYPE: DNA
<213> ORGANISM: Homo sapiens

<400> SEQUENCE: 25
caccatggga gaagcctccc cacctgcccc cgcaaggcgg catctgctgg tcctgctgct    60
gctcctctct accctggtga tccctccgc tgcagctcct atccatgatg ctgacgccca    120
agagagctcc ttgggtctca caggcctcca gagcctactc caaggcttca gccgactttt    180
cctgaaaggt aacctgcttc ggggcataga cagcttattc tctgccccca tggacttccg    240
gggcctccct gggaactacc acaaagagga gaaccaggag caccagctgg ggaacaacac    300
cctctccagc cacctccaga tcgacaaggt acccaggatg gaggagaagg aggccctggt    360
acccatccag aaggccacgg acagcttcca cacagaactc catccccggg tggccttctg    420
gatcattaag ctgccacggc ggaggtccca ccaggatgcc ctggagggcg gccatggctc    480
agcgagaagc gacaccgcct gcaggccatc cgggatggac tccgcaaggg acccacaag    540 gacgtcctag aagggggac cgagagctcc tcccactcca ggctgtcccc cccgaaagac    600
ccacttactg tacatcctca ggccctctcg gcagctgtag                         640

<210> SEQ ID NO 26
<211> LENGTH: 640
<212> TYPE: DNA
<213> ORGANISM: Homo sapiens

<400> SEQUENCE: 26
caccatggga gaagcctccc cacctgcccc cgcaaggcgg catctgctgg tcctgctgct    60
gctcctctct accctggtga tccctccgc tgcagctcct atccatgatg ctgacgccca    120
agagagctcc ttgggtctca caggcctcca gagcctactc caaggcttca gccgactttt    180
cctgaaaggt aacctgcttc ggggcataga cagcttattc tctgccccca tggacttccg    240
gggcctccct gggaactacc acaaagagga gaaccaggag caccagctgg ggaacaacac    300
cctctccagc cacctccaga tcgacaaggt acccaggatg gaggagaagg aggccctggt    360
acccatccag aaggccacgg acagcttcca cacagaactc catccccggg tggccttctg    420
```

| | |
|---|---:|
| gatcattaag ctgccacggc ggaggtccca ccaggatgcc ctggagggcg gccatggctc | 480 |
| agcgagaagc gacaccgcct gcaggccatc cgggatggac tccgcaaggg gacccacaag | 540 |
| gacgtcctag aagaggggac cgagagctcc tcccactcca ggctgtcccc ccgaaagac | 600 |
| ccacttactg tacatcctca ggccctctcg gcagctgtag | 640 |

<210> SEQ ID NO 27
<211> LENGTH: 499
<212> TYPE: DNA
<213> ORGANISM: Homo sapiens

<400> SEQUENCE: 27

| | |
|---|---:|
| caccatggga gaagcctccc cacctgcccc cgcaaggcgg catctgctgg tcctgctgct | 60 |
| gctcctctct accctggtga tcccctccgc tgcagctcct atccatgatg ctgacgccca | 120 |
| agagagctcc ttgggtctca caggcctcca gagcctactc caaggcttca gccgactttt | 180 |
| cctgaaagta cccaggatgg aggagaagga ggccctggta cccatccaga aggccacgga | 240 |
| cagcttccac acagaactcc atccccgggt ggccttctgg atcattaagc tgccacggcg | 300 |
| gaggtcccac caggatgccc tgagggcag ccatggctca gcgagaagcg acaccgcctg | 360 |
| caggccatcc gggatggact ccgcaagggg acccacaagg acgtcctaga agaggggacc | 420 |
| gagagctcct cccactccag gctgtccccc ccgaaagacc cacttactgt acatcctcag | 480 |
| gccctctcgg cagctgtag | 499 |

<210> SEQ ID NO 28
<211> LENGTH: 499
<212> TYPE: DNA
<213> ORGANISM: Homo sapiens

<400> SEQUENCE: 28

| | |
|---|---:|
| caccatggga gaagcctccc cacctgcccc cgcaaggcgg catctgctgg tcctgctgct | 60 |
| gctcctctct accctggtga tcccctccgc tgcagctcct atccatgatg ctgacgccca | 120 |
| agagagctcc ttgggtctca caggcctcca gagcctactc caaggcttca gccgactttt | 180 |
| cctgaaagta cccaggatgg aggagaagga ggccctggta cccatccaga aggccacgga | 240 |
| cagcttccac acagaactcc atccccgggt ggccttctgg atcattaagc tgccacggcg | 300 |
| gaggtcccac caggatgccc tgagggcag ccatggctca gcgagaagcg acaccgcctg | 360 |
| caggccatcc gggatggact ccgcaagggg acccacaagg acgtcctaga agaggggacc | 420 |
| gagagctcct cccactccag gctgtccccc ccgaaagacc cacttactgt acatcctcag | 480 |
| gccctctcgg cagctgtag | 499 |

<210> SEQ ID NO 29
<211> LENGTH: 499
<212> TYPE: DNA
<213> ORGANISM: Homo sapiens

<400> SEQUENCE: 29

| | |
|---|---:|
| caccatggga gaagcctccc cacctgcccc cgcaaggcgg catctgctgg tcctgctgct | 60 |
| gctcctctct accctggtga tcccctccgc tgcagctcct atccatgatg ctgacgccca | 120 |
| agagagctcc ttgggtctca caggcctcca gagcctactc caaggcttca gccgactttt | 180 |
| cctgaaagta cccaggatgg aggagaagga ggccctggta cccatccaga aggccacgga | 240 |
| cagcttccac acagaactcc atccccgggt ggccttctgg atcattaagc tgccacggcg | 300 |
| gaggtcccac caggatgccc tgagggcag ccatggctca gcgagaagcg acaccgcctg | 360 |

```
caggccatcc gggatggact ccgcaagggg acccacaagg acgtcctaga agaggggacc      420
gagagctcct cccactccag gctgtccccc ccgaaagacc cacttactgt acatcctcag      480
gccctctcgg cagctgtag                                                  499

<210> SEQ ID NO 30
<211> LENGTH: 499
<212> TYPE: DNA
<213> ORGANISM: Homo sapiens

<400> SEQUENCE: 30
caccatggga gaagcctccc cacctgcccc cgcaaggcgg catctgctgg tcctgctgct       60
gctcctctct accctggtga tcccctccgc tgcagctcct atccatgatg ctgacgccca      120
agagagctcc ttgggtctca caggcctcca gagcctactc caaggcttca gccgactttt      180
cctgaaagta cccaggatgg aggagaagga ggccctggta cccatccaga aggccacgga      240
cagcttccac acagaactcc atccccgggt ggccttctgg atcattaagc tgccacggcg      300
gaggtcccac caggatgccc tggagggcag ccatggctca gcgagaagcg acaccgcctg      360
caggccatcc gggatggact ccgcaagggg acccacaagg acgtcctaga agaggggacc      420
gagagctcct cccactccag gctgtccccc ccgaaagacc cacttactgt acatcctcag      480
gccctctcgg cagctgtag                                                  499

<210> SEQ ID NO 31
<211> LENGTH: 499
<212> TYPE: DNA
<213> ORGANISM: Homo sapiens

<400> SEQUENCE: 31
caccatggga gaagcctccc cacctgcccc cgcaaggcgg catctgctgg tcctgctgct       60
gctcctctct accctggtga tcccctccgc tgcagctcct atccatgatg ctgacgccca      120
agagagctcc ttgggtctca caggcctcca gagcctactc caaggcttca gccgactttt      180
cctgaaagta cccaggatgg aggagaagga ggccctggta cccatccaga aggccacgga      240
cagcttccac acagaactcc atccccgggt ggccttctgg atcattaagc tgccacggcg      300
gaggtcccac caggatgccc tggagggcag ccatggctca gcgagaagcg acaccgcctg      360
caggccatcc gggatggact ccgcaagggg acccacaagg acgtcctaga agaggggacc      420
gagagctcct cccactccag gctgtccccc ccgaaagacc cacttactgt acatcctcag      480
gccctctcgg cagctgtag                                                  499

<210> SEQ ID NO 32
<211> LENGTH: 242
<212> TYPE: PRT
<213> ORGANISM: Homo sapiens

<400> SEQUENCE: 32

Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Ala Ala Pro
            20                  25                  30

Ile His Asp Ala Asp Ala Gln Glu Ser Ser Leu Gly Leu Thr Gly Leu
        35                  40                  45

Gln Ser Leu Leu Gln Gly Phe Ser Arg Leu Phe Leu Lys Gly Asn Leu
    50                  55                  60

Leu Arg Gly Ile Asp Ser Leu Phe Ser Ala Pro Met Asp Phe Arg Gly
65                  70                  75                  80
```

```
Leu Pro Gly Asn Tyr His Lys Glu Glu Asn Gln Glu His Gln Leu Gly
                85                  90                  95

Asn Asn Thr Leu Ser Ser His Leu Gln Ile Asp Lys Arg Thr Asp Asn
            100                 105                 110

Lys Thr Gly Glu Val Leu Ile Ser Glu Asn Val Val Ala Ser Ile Gln
            115                 120                 125

Pro Ala Glu Gly Ser Phe Glu Gly Asp Leu Lys Val Pro Arg Met Glu
            130                 135                 140

Glu Lys Glu Ala Leu Val Pro Ile Gln Lys Ala Thr Asp Ser Phe His
145                 150                 155                 160

Thr Glu Leu His Pro Arg Val Ala Phe Trp Ile Ile Lys Leu Pro Arg
                165                 170                 175

Arg Arg Ser His Gln Asp Ala Leu Glu Gly Ser His Trp Leu Ser Glu
            180                 185                 190

Lys Arg His Arg Leu Gln Ala Ile Arg Asp Gly Leu Arg Lys Gly Thr
            195                 200                 205

His Lys Asp Val Leu Glu Gly Thr Glu Ser Ser His Ser Arg
            210                 215                 220

Leu Ser Pro Arg Lys Thr His Leu Leu Tyr Ile Leu Arg Pro Ser Arg
225                 230                 235                 240

Gln Leu

<210> SEQ ID NO 33
<211> LENGTH: 242
<212> TYPE: PRT
<213> ORGANISM: Homo sapiens

<400> SEQUENCE: 33

Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Ala Ala Ala Pro
            20                  25                  30

Ile His Asp Ala Asp Ala Gln Glu Ser Ser Leu Gly Leu Thr Gly Leu
            35                  40                  45

Gln Ser Leu Leu Gln Gly Phe Ser Arg Leu Phe Leu Lys Gly Asn Leu
50                  55                  60

Leu Arg Gly Ile Asp Ser Leu Phe Ser Ala Pro Met Asp Phe Arg Gly
65                  70                  75                  80

Leu Pro Gly Asn Tyr His Lys Glu Glu Asn Gln Glu His Gln Leu Gly
                85                  90                  95

Asn Asn Thr Leu Ser Ser His Leu Gln Ile Asp Lys Met Thr Asp Asn
            100                 105                 110

Lys Thr Gly Glu Val Leu Ile Ser Glu Asn Val Val Ala Ser Ile Gln
            115                 120                 125

Pro Ala Glu Gly Ser Phe Glu Gly Asp Leu Lys Val Pro Arg Met Glu
            130                 135                 140

Glu Lys Glu Ala Leu Val Pro Ile Gln Lys Ala Thr Asp Ser Phe His
145                 150                 155                 160

Thr Glu Leu His Pro Arg Val Ala Phe Trp Ile Ile Lys Leu Pro Arg
                165                 170                 175

Arg Arg Ser His Gln Asp Ala Leu Glu Gly Ser His Trp Leu Ser Glu
            180                 185                 190

Lys Arg His Arg Leu Gln Ala Ile Arg Asp Gly Leu Arg Lys Gly Thr
            195                 200                 205
```

His Lys Asp Val Leu Glu Glu Gly Thr Glu Ser Ser His Ser Arg
        210                 215                 220

Leu Ser Pro Arg Lys Thr His Leu Leu Tyr Ile Leu Arg Pro Ser Arg
225                 230                 235                 240

Gln Leu

<210> SEQ ID NO 34
<211> LENGTH: 242
<212> TYPE: PRT
<213> ORGANISM: Homo sapiens

<400> SEQUENCE: 34

Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Thr Ala Ala Pro
                20                  25                  30

Ile His Asp Ala Asp Ala Gln Glu Ser Ser Leu Gly Leu Thr Gly Leu
            35                  40                  45

Gln Ser Leu Leu Gln Gly Phe Ser Arg Leu Phe Leu Lys Gly Asn Leu
        50                  55                  60

Leu Arg Gly Ile Asp Ser Leu Phe Ser Ala Pro Met Asp Phe Arg Gly
65                  70                  75                  80

Leu Pro Gly Asn Tyr His Lys Glu Glu Asn Gln Glu His Gln Leu Gly
                85                  90                  95

Asn Asn Thr Leu Ser Ser His Leu Gln Ile Asp Lys Met Thr Asp Asn
            100                 105                 110

Lys Thr Gly Glu Val Leu Ile Ser Glu Asn Val Val Ala Ser Ile Gln
        115                 120                 125

Pro Ala Glu Gly Ser Phe Glu Gly Asp Leu Lys Val Pro Arg Met Glu
    130                 135                 140

Glu Lys Glu Ala Leu Val Pro Ile Gln Lys Ala Thr Asp Ser Phe His
145                 150                 155                 160

Thr Glu Leu His Pro Arg Val Ala Phe Trp Ile Ile Lys Leu Pro Arg
                165                 170                 175

Arg Arg Ser His Gln Asp Ala Leu Glu Gly Ser His Trp Leu Ser Glu
            180                 185                 190

Lys Arg His Arg Leu Gln Ala Ile Arg Asp Gly Leu Arg Lys Gly Thr
        195                 200                 205

His Lys Asp Val Leu Glu Glu Gly Thr Glu Ser Ser His Ser Arg
    210                 215                 220

Leu Ser Pro Arg Lys Thr His Leu Leu Tyr Ile Leu Arg Pro Ser Arg
225                 230                 235                 240

Gln Leu

<210> SEQ ID NO 35
<211> LENGTH: 242
<212> TYPE: PRT
<213> ORGANISM: Homo sapiens

<400> SEQUENCE: 35

Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Thr Ala Ala Pro
                20                  25                  30

Ile His Asp Ala Asp Ala Gln Glu Ser Ser Leu Gly Leu Thr Gly Leu
            35                  40                  45

```
Gln Ser Leu Leu Gln Gly Phe Ser Arg Leu Phe Leu Lys Gly Asn Leu
        50                  55                  60

Leu Arg Gly Ile Asp Ser Leu Phe Ser Ala Pro Met Asp Phe Arg Gly
 65                  70                  75                  80

Leu Pro Gly Asn Tyr His Lys Glu Glu Asn Gln Glu His Gln Leu Gly
                    85                  90                  95

Asn Asn Thr Leu Ser Ser His Leu Gln Ile Asp Lys Met Thr Asp Asn
                100                 105                 110

Lys Thr Gly Glu Val Leu Ile Ser Glu Asn Val Val Ala Ser Ile Gln
            115                 120                 125

Pro Ala Glu Gly Ser Phe Glu Gly Asp Leu Lys Val Pro Arg Met Glu
        130                 135                 140

Glu Lys Glu Ala Leu Val Pro Ile Gln Lys Ala Thr Asp Ser Phe His
145                 150                 155                 160

Thr Glu Leu His Pro Arg Val Ala Phe Trp Ile Ile Lys Leu Pro Arg
                165                 170                 175

Arg Arg Ser His Gln Asp Ala Leu Glu Gly Ser His Trp Leu Ser Glu
                180                 185                 190

Lys Arg His Arg Leu Gln Ala Ile Arg Asp Gly Leu Arg Lys Gly Thr
            195                 200                 205

His Lys Asp Val Leu Glu Gly Thr Glu Ser Ser Ser His Ser Arg
        210                 215                 220

Leu Ser Pro Arg Lys Thr His Leu Leu Tyr Ile Leu Arg Pro Ser Arg
225                 230                 235                 240

Gln Leu

<210> SEQ ID NO 36
<211> LENGTH: 242
<212> TYPE: PRT
<213> ORGANISM: Homo sapiens

<400> SEQUENCE: 36

Met Gly Glu Ala Ser Pro Pro Ala Pro Ala Arg Arg His Leu Leu Val
 1               5                  10                  15

Leu Leu Leu Leu Leu Ser Thr Leu Val Ile Pro Ser Thr Ala Ala Pro
                20                  25                  30

Ile His Asp Ala Asp Ala Gln Glu Ser Ser Leu Gly Leu Thr Gly Leu
            35                  40                  45

Gln Ser Leu Leu Gln Gly Phe Ser Arg Leu Phe Leu Lys Gly Asn Leu
        50                  55                  60

Leu Arg Gly Ile Asp Ser Leu Phe Ser Ala Pro Met Asp Phe Arg Gly
 65                  70                  75                  80

Leu Pro Gly Asn Tyr His Lys Glu Glu Asn Gln Glu His Gln Leu Gly
                    85                  90                  95

Asn Asn Thr Leu Ser Ser His Leu Gln Ile Asp Lys Met Thr Asp Asn
                100                 105                 110

Lys Thr Gly Glu Val Leu Ile Ser Glu Asn Val Val Ala Ser Ile Gln
            115                 120                 125

Pro Ala Glu Gly Ser Phe Glu Gly Asp Leu Lys Val Pro Arg Met Glu
        130                 135                 140

Glu Lys Glu Ala Leu Val Pro Ile Gln Lys Ala Thr Asp Ser Phe His
145                 150                 155                 160

Thr Glu Leu His Pro Arg Val Ala Phe Trp Ile Ile Lys Leu Pro Arg
                165                 170                 175

Arg Arg Ser His Gln Asp Ala Leu Glu Gly Ser His Trp Leu Ser Glu
```

Lys Arg His Arg Leu Gln Ala Ile Arg Asp Gly Leu Arg Lys Gly Thr
195 200 205

His Lys Asp Val Leu Glu Glu Gly Thr Glu Ser Ser Ser His Ser Arg
210 215 220

Leu Ser Pro Arg Lys Thr His Leu Leu Tyr Ile Leu Arg Pro Ser Arg
225 230 235 240

Gln Leu

<210> SEQ ID NO 37
<211> LENGTH: 242
<212> TYPE: PRT
<213> ORGANISM: Homo sapiens

<400> SEQUENCE: 37

Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Thr Ala Ala Pro
                20                  25                  30

Ile His Asp Ala Asp Ala Gln Glu Ser Ser Leu Gly Leu Thr Gly Leu
            35                  40                  45

Gln Ser Leu Leu Gln Gly Phe Ser Arg Leu Phe Leu Lys Gly Asn Leu
        50                  55                  60

Leu Arg Gly Ile Asp Ser Leu Phe Ser Ala Pro Met Asp Phe Arg Gly
65                  70                  75                  80

Leu Pro Gly Asn Tyr His Lys Glu Glu Asn Gln Glu His Gln Leu Gly
                85                  90                  95

Asn Asn Thr Leu Ser Ser His Leu Gln Ile Asp Lys Met Thr Asp Asn
                100                 105                 110

Lys Thr Gly Glu Val Leu Ile Ser Glu Asn Val Val Ala Ser Ile Gln
            115                 120                 125

Pro Ala Glu Gly Ser Phe Glu Gly Asp Leu Lys Val Pro Arg Met Glu
        130                 135                 140

Glu Lys Glu Ala Leu Val Pro Ile Gln Lys Ala Thr Asp Ser Phe His
145                 150                 155                 160

Thr Glu Leu His Pro Arg Val Ala Phe Trp Ile Ile Lys Leu Pro Arg
                165                 170                 175

Arg Arg Ser His Gln Asp Ala Leu Glu Gly Gly His Trp Leu Ser Glu
                180                 185                 190

Lys Arg His Arg Leu Gln Ala Ile Arg Asp Gly Leu Arg Lys Gly Thr
            195                 200                 205

His Lys Asp Val Leu Glu Glu Gly Thr Glu Ser Ser Ser His Ser Arg
        210                 215                 220

Leu Ser Pro Arg Lys Thr His Leu Leu Tyr Ile Leu Arg Pro Ser Arg
225                 230                 235                 240

Gln Leu

<210> SEQ ID NO 38
<211> LENGTH: 211
<212> TYPE: PRT
<213> ORGANISM: Homo sapiens

<400> SEQUENCE: 38

Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Ala Ala Ala Pro

```
            20                  25                  30
Ile His Asp Ala Asp Ala Gln Glu Ser Ser Leu Gly Leu Thr Gly Leu
         35                  40                  45
Gln Ser Leu Leu Gln Gly Phe Ser Arg Leu Phe Leu Lys Gly Asn Leu
     50                  55                  60
Leu Arg Gly Ile Asp Ser Leu Phe Ser Ala Pro Met Asp Phe Arg Gly
 65                  70                  75                  80
Leu Pro Gly Asn Tyr His Lys Glu Glu Asn Gln Glu His Gln Leu Gly
                 85                  90                  95
Asn Asn Thr Leu Ser Ser His Leu Gln Ile Asp Lys Val Pro Arg Met
             100                 105                 110
Glu Glu Lys Glu Ala Leu Val Pro Ile Gln Lys Ala Thr Asp Ser Phe
         115                 120                 125
His Thr Glu Leu His Pro Arg Val Ala Phe Trp Ile Ile Lys Leu Pro
     130                 135                 140
Arg Arg Arg Ser His Gln Asp Ala Leu Glu Gly Gly His Trp Leu Ser
145                 150                 155                 160
Glu Lys Arg His Arg Leu Gln Ala Ile Arg Asp Gly Leu Arg Lys Gly
                 165                 170                 175
Thr His Lys Asp Val Leu Glu Glu Gly Thr Glu Ser Ser Ser His Ser
             180                 185                 190
Arg Leu Ser Pro Arg Lys Thr His Leu Leu Tyr Ile Leu Arg Pro Ser
         195                 200                 205
Arg Gln Leu
         210

<210> SEQ ID NO 39
<211> LENGTH: 211
<212> TYPE: PRT
<213> ORGANISM: Homo sapiens

<400> SEQUENCE: 39

Met Gly Glu Ala Ser Pro Pro Ala Pro Ala Arg Arg His Leu Leu Val
 1               5                  10                  15
Leu Leu Leu Leu Leu Ser Thr Leu Val Ile Pro Ser Ala Ala Ala Pro
             20                  25                  30
Ile His Asp Ala Asp Ala Gln Glu Ser Ser Leu Gly Leu Thr Gly Leu
         35                  40                  45
Gln Ser Leu Leu Gln Gly Phe Ser Arg Leu Phe Leu Lys Gly Asn Leu
     50                  55                  60
Leu Arg Gly Ile Asp Ser Leu Phe Ser Ala Pro Met Asp Phe Arg Gly
 65                  70                  75                  80
Leu Pro Gly Asn Tyr His Lys Glu Glu Asn Gln Glu His Gln Leu Gly
                 85                  90                  95
Asn Asn Thr Leu Ser Ser His Leu Gln Ile Asp Lys Val Pro Arg Met
             100                 105                 110
Glu Glu Lys Glu Ala Leu Val Pro Ile Gln Lys Ala Thr Asp Ser Phe
         115                 120                 125
His Thr Glu Leu His Pro Arg Val Ala Phe Trp Ile Ile Lys Leu Pro
     130                 135                 140
Arg Arg Arg Ser His Gln Asp Ala Leu Glu Gly Gly His Trp Leu Ser
145                 150                 155                 160
Glu Lys Arg His Arg Leu Gln Ala Ile Arg Asp Gly Leu Arg Lys Gly
                 165                 170                 175
Thr His Lys Asp Val Leu Glu Glu Glu Thr Glu Ser Ser Ser His Ser
```

```
                    180                 185                 190
Arg Leu Ser Pro Arg Lys Thr His Leu Leu Tyr Ile Leu Arg Pro Ser
            195                 200                 205

Arg Gln Leu
        210

<210> SEQ ID NO 40
<211> LENGTH: 164
<212> TYPE: PRT
<213> ORGANISM: Homo sapiens

<400> SEQUENCE: 40

Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Ala Ala Ala Pro
            20                  25                  30

Ile His Asp Ala Asp Ala Gln Glu Ser Ser Leu Gly Leu Thr Gly Leu
        35                  40                  45

Gln Ser Leu Leu Gln Gly Phe Ser Arg Leu Phe Leu Lys Val Pro Arg
    50                  55                  60

Met Glu Glu Lys Glu Ala Leu Val Pro Ile Gln Lys Ala Thr Asp Ser
65                  70                  75                  80

Phe His Thr Glu Leu His Pro Arg Val Ala Phe Trp Ile Ile Lys Leu
                85                  90                  95

Pro Arg Arg Arg Ser His Gln Asp Ala Leu Glu Gly Ser His Trp Leu
            100                 105                 110

Ser Glu Lys Arg His Arg Leu Gln Ala Ile Arg Asp Gly Leu Arg Lys
        115                 120                 125

Gly Thr His Lys Asp Val Leu Lys Glu Gly Thr Glu Ser Ser Ser His
    130                 135                 140

Ser Arg Leu Ser Pro Arg Lys Thr His Leu Leu Tyr Ile Leu Arg Pro
145                 150                 155                 160

Ser Arg Gln Leu

<210> SEQ ID NO 41
<211> LENGTH: 164
<212> TYPE: PRT
<213> ORGANISM: Homo sapiens

<400> SEQUENCE: 41

Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Ala Ala Ala Pro
            20                  25                  30

Ile His Asp Ala Asp Ala Gln Glu Ser Ser Leu Gly Leu Thr Gly Leu
        35                  40                  45

Gln Ser Leu Leu Gln Gly Phe Ser Arg Leu Phe Leu Lys Val Pro Arg
    50                  55                  60

Met Glu Glu Lys Glu Ala Leu Val Pro Ile Gln Lys Ala Thr Asp Ser
65                  70                  75                  80

Phe His Thr Glu Leu His Pro Arg Val Ala Phe Trp Ile Ile Lys Leu
                85                  90                  95

Pro Arg Arg Arg Ser His Gln Asp Ala Leu Glu Gly Ser His Trp Leu
            100                 105                 110

Ser Glu Lys Arg His Arg Leu Gln Ala Ile Arg Asp Gly Leu Arg Lys
        115                 120                 125
```

```
Gly Thr His Lys Asp Val Leu Glu Glu Gly Thr Glu Ser Ser Ser His
        130                 135                 140

Ser Arg Leu Ser Pro Arg Lys Thr His Leu Leu Tyr Ile Leu Arg Pro
145                 150                 155                 160

Ser Arg Gln Leu

<210> SEQ ID NO 42
<211> LENGTH: 164
<212> TYPE: PRT
<213> ORGANISM: Homo sapiens

<400> SEQUENCE: 42

Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Ala Ala Ala Pro
                20                  25                  30

Ile His Asp Ala Asp Ala Gln Glu Ser Ser Leu Gly Leu Thr Gly Leu
            35                  40                  45

Gln Ser Leu Leu Gln Gly Phe Ser Arg Leu Phe Leu Lys Val Pro Arg
        50                  55                  60

Met Glu Glu Lys Glu Ala Leu Val Pro Ile Gln Lys Ala Thr Asp Ser
65                  70                  75                  80

Phe His Thr Glu Leu His Pro Arg Val Ala Phe Trp Ile Ile Lys Leu
                85                  90                  95

Pro Arg Arg Arg Ser His Gln Asp Ala Leu Glu Gly Ser His Trp Leu
            100                 105                 110

Ser Glu Lys Arg His Arg Leu Gln Ala Ile Arg Asp Gly Leu Arg Lys
        115                 120                 125

Gly Thr His Lys Asp Val Leu Glu Glu Gly Thr Glu Ser Ser Ser His
        130                 135                 140

Ser Arg Leu Ser Pro Arg Lys Thr His Leu Leu Tyr Ile Leu Arg Pro
145                 150                 155                 160

Ser Arg Gln Leu

<210> SEQ ID NO 43
<211> LENGTH: 164
<212> TYPE: PRT
<213> ORGANISM: Homo sapiens

<400> SEQUENCE: 43

Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Ala Ala Ala Pro
                20                  25                  30

Ile His Asp Ala Asp Ala Gln Glu Ser Ser Leu Gly Leu Thr Gly Leu
            35                  40                  45

Gln Ser Leu Leu Gln Gly Phe Ser Arg Leu Phe Leu Lys Val Pro Arg
        50                  55                  60

Met Glu Glu Lys Glu Ala Leu Val Pro Ile Gln Lys Ala Thr Asp Ser
65                  70                  75                  80

Phe His Thr Glu Leu His Pro Arg Val Ala Phe Trp Ile Ile Lys Leu
                85                  90                  95

Pro Arg Arg Arg Ser His Gln Asp Ala Leu Glu Gly Ser His Trp Leu
            100                 105                 110

Ser Glu Lys Arg His Arg Leu Gln Ala Ile Arg Asp Gly Leu Arg Lys
        115                 120                 125
```

-continued

```
Gly Thr His Lys Asp Val Leu Lys Glu Gly Thr Glu Ser Ser Ser His
        130                 135                 140

Ser Arg Leu Ser Pro Arg Lys Thr His Leu Leu Tyr Ile Leu Arg Pro
145                 150                 155                 160

Ser Arg Gln Leu

<210> SEQ ID NO 44
<211> LENGTH: 164
<212> TYPE: PRT
<213> ORGANISM: Homo sapiens

<400> SEQUENCE: 44

Met Gly Glu Ala Ser Pro Pro Ala Pro Ala Arg Arg His Leu Leu Val
1               5                   10                  15

Leu Leu Leu Leu Leu Ser Thr Leu Val Ile Pro Ser Ala Ala Ala Pro
                20                  25                  30

Ile His Asp Ala Asp Ala Gln Glu Ser Ser Leu Gly Leu Thr Gly Leu
            35                  40                  45

Gln Ser Leu Leu Gln Gly Phe Ser Arg Leu Phe Leu Lys Val Pro Arg
    50                  55                  60

Met Glu Glu Lys Glu Ala Leu Val Pro Ile Gln Lys Ala Thr Asp Ser
65                  70                  75                  80

Phe His Thr Glu Leu His Pro Arg Val Ala Phe Trp Ile Ile Lys Leu
                85                  90                  95

Pro Arg Arg Arg Ser His Gln Asp Ala Leu Glu Gly Ser His Trp Leu
                100                 105                 110

Ser Glu Lys Arg His Arg Leu Gln Ala Ile Arg Asp Gly Leu Arg Lys
            115                 120                 125

Gly Thr His Lys Asp Val Leu Lys Glu Gly Thr Glu Ser Ser Ser His
        130                 135                 140

Ser Arg Leu Ser Pro Arg Lys Thr His Leu Leu Tyr Ile Leu Arg Pro
145                 150                 155                 160

Ser Arg Gln Leu
```